United States Patent [19]

Iwaoka et al.

[11] Patent Number: 5,834,499
[45] Date of Patent: Nov. 10, 1998

[54] 5-HT₃ RECEPTOR AGONIST, NOVEL THIAZOLE DERIVATIVE AND INTERMEDIATE THEREOF

[75] Inventors: Kiyoshi Iwaoka; Hideki Anan; Naoki Imanishi; Kenichi Kazuta; Hiroyuki Koshio; Takeshi Suzuki; Hirotsune Itahana; Hiroyuki Ito; Keiji Miyata; Mitsuaki Ohta, all of Ibaraki, Japan

[73] Assignee: Yamanouchi Pharmaceutical Co., Ltd., Tokyo, Japan

[21] Appl. No.: 700,428

[22] PCT Filed: Mar. 9, 1995

[86] PCT No.: PCT/JP95/00385

§ 371 Date: Aug. 26, 1996

§ 102(e) Date: Aug. 26, 1996

[87] PCT Pub. No.: WO95/24399

PCT Pub. Date: Sep. 14, 1995

[30] Foreign Application Priority Data

Mar. 11, 1994 [JP] Japan .................................. 6-067822

[51] Int. Cl.⁶ ...................... A61K 31/425; C07D 417/04
[52] U.S. Cl. .......................... 514/366; 548/150; 548/151; 546/198; 546/199; 546/133; 546/138; 546/112; 514/305; 514/299; 514/321; 514/322
[58] Field of Search ..................... 548/150, 151; 514/366; 546/198, 112, 133, 138

[56] References Cited

U.S. PATENT DOCUMENTS 4,952,587 8/1990 Baker et al. .............................. 514/305
5,424,431 6/1995 Ohta et al. ............................... 546/114

FOREIGN PATENT DOCUMENTS

| | | |
|---|---|---|
| 230334 | 7/1987 | European Pat. Off. . |
| 307141 | 3/1989 | European Pat. Off. . |
| 513387 | 11/1992 | European Pat. Off. . |
| 0666263 | 8/1995 | European Pat. Off. . |
| 5222015 | 8/1993 | Japan . |
| 5-345772 | 12/1993 | Japan . |
| 7-070136 | 3/1995 | Japan . |
| 95 24406 | 9/1995 | WIPO . |

OTHER PUBLICATIONS

Il Farmaco, vol. 50, No. 2, Feb. 1995, pp. 77–82, Perrone R. et al.: "Conformationally Restricted Thiazole Derivatives as Novel . . . Ligands".

Primary Examiner—Johann Richter
Assistant Examiner—Laura Cross Lutz
Attorney, Agent, or Firm—Burgess, Ryan & Wayne

[57] ABSTRACT

A 5-HT₃ receptor against containing a thiazole derivative as the effective ingredient is provided and is represented by the Formula (I):

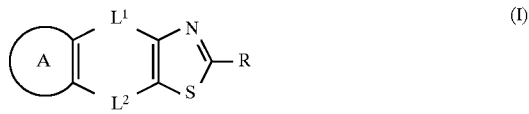

wherein the A ring is substituted or unsubstituted and represents a benzene or a heterocyclic ring with one or two heteroatoms;

one of $L_1$ or $L_2$ represents a single bond and the other is non-existent or represents an alkylene or alkenylene group;

R represents:

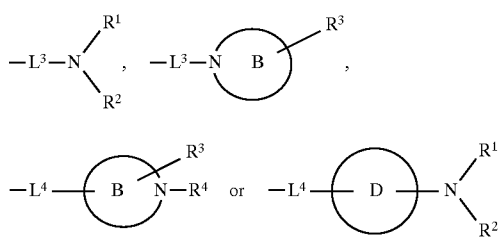

6 Claims, No Drawings

5-HT₃ RECEPTOR AGONIST, NOVEL THIAZOLE DERIVATIVE AND INTERMEDIATE THEREOF

This application is a 371 of PCT/JP95/00385 filed Mar. 9, 1995 published as WO95/24399 Sep. 14, 1995.

1. Technical Field

The present invention relates to a 5-HT₃ receptor agonist which comprises a thiazole derivative as an effective ingredient; and a novel thiazole derivative and a pharmaceutically acceptable salt thereof as well as an intermediate thereof.

2. Background Art

The compound of the present invention act as an effective and selective agonist for the neuronal serotonin (5-HT) receptor located in the primary afferent nerve of the enteric nervous system or central nervous system. This type of receptor is now considered as a 5-HT₃ receptor. The compound of the present invention exerts its function by releasing acetylcholine from the efferent nerve ending in the digestive tracts. It is known that stimulation of the acetylcholine receptor in the digestive tracts accelerates motility of the gastrointestinal tracts and improves functional reduction of the gastrointestinal tracts (Goodman and Gilman's, The Pharmacological Basis of Therapeutics 8th edition, p. 125, (1990), Pergamon Press). It is also known that the 5-HT₃ receptor is present in the presynaptic area of the central nervous system and inhibits nervous activities by its stimulation [J. Neurosci., 11, 1881 (1991)].

In consequence, it is considered that a 5-HT₃ receptor agonist is useful especially against gastrointestinal disorders.

Though no compound having a selective agonistic activity on the 5-HT₃ receptor had been found, the inventors of the present invention reported that thiazole derivatives disclosed in WO 92/07849 possess a selective 5-HT₃ receptor agonistic activity.

The compound having selective agonistic activities for the 5-HT₃ receptor has not been found so far; however, the present inventors have reported that a thiazole derivative as disclosed in WO 92/07849 has selective agonistic activities for the 5-HT₃ receptor.

The unexamined published Japanese patent application JP-A-62-252780 discloses a compound represented by the following formula:

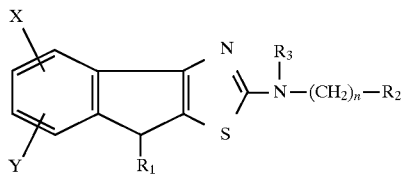

(refer to the above published application concerning the detailed definition). However, the compound disclosed in the above published application is substituted at the 2-position of indenothiazole by a substituent through a nitrogen atom, so that it is structurally different from the compound of the present invention. Moreover, in the published application, only antiulcer effects of the compound are disclosed and there is no disclosure about the selective agonistic activities for a 5-HT₃ receptor.

The unexamined published Japanese patent application JP-A-5-51318 (WO 92/09586 pamphlet) describes, as an effective ingredient in the use claim, the compound represented by the following formula:

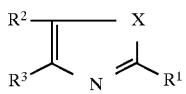

(refer to the above published application concerning the detailed definition) and EP 0307141 describes, as an effective ingredient in the use claim, the compound represented by the following formula:

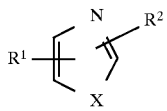

(refer to the above document concerning the detailed definition), respectively. The compound (I), which will be described later, which is an effective ingredient for the pharmaceutical composition of the present invention, embraces the compounds described comprehensively in these documents. In these documents, however, there is only a description about the application of the compound for the preparation of an agent for suppressing active oxygen produced by neutrophils, that is, the preparation of a cholinergic neurosis drug and they do not include any description or suggestion that the compound has selective agonistic activities for 5-HT₃ receptor.

DISCLOSURE OF THE INVENTION

The present inventors have proceeded with a further research on the agonistic activities for a 5-HT₃ receptor under the technical circumstances as described above. The present inventors focused on an index for the 5-HT₃ receptor agonistic activities, which is independent from the von Bezold-Jarisch reflex known as the index of 5-HT₃ receptor agonistic activities [A. S. Paintal et al., Physiol. Rev., 53, 159(1973)], i.e., on the contractile effects of 5-HT on the isolated colon from a guinea pig through a 5-HT₃ receptor, and the present inventors have proceeded with a synthetic study. As a result, it has been found that a thiazole derivative represented by the following formula (I) has excellent 5-HT₃ receptor agonistic activities, leading to the completion of the present invention.

That is, the present invention therefore provides a 5-HT₃ receptor agonist which comprises a thiazole derivative represented by the formula (I) or a pharmaceutically acceptable salt thereof, and a pharmaceutically acceptable carrier; use of a thiazole derivative represented by the following formula (I) or a pharmaceutically acceptable salt thereof for the preparation of a medicament which is useful for the therapeutic treatment of a patient suffering from a disease in which clinical symptoms are expressed depending on 5-HT₃ receptor dysergia, or a therapeutic method for treating a disease in which clinical symptoms are expressed depending on 5-HT₃ receptor dysergy, said method comprising administering to a patient a necessary effective amount of a thiazole derivative represented by the following formula (I) or pharmaceutically acceptable salt thereof.

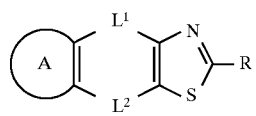

(I)

wherein each symbol represents the following meaning:

Ring A: the following ring which may be substituted by one or more substituents selected from the group consisting of a halogen atom, a lower alkyl group and a lower alkoxyl group:
1) a benzene ring, or
2) a 5-membered or 6-membered unsaturated heterocyclic ring having one or two hetero atoms selected from the group consisting of a nitrogen atom, an oxygen atom and a sulfur atom, $L_1$ and $L_2$: one of them represents a single bond, and the other one, represents an alkylene group having 1 to 4 carbon atoms or an alkenylene group having 2 to 5 carbon atoms, R: a group represented by one of the following formulae:

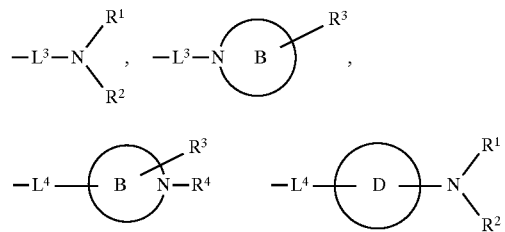

$L^3$: a lower alkylene group, $L^4$: a single bond or a lower alkylene group, $R^1$ and $R^2$: the same or different and individually a hydrogen atom, a lower alkyl group or an amino-protecting group, $R^3$: a hydrogen atom, a lower alkyl group, an oxo group or a protected or unprotected amino group, $R^4$: a hydrogen atom, a lower alkyl group, an aralkyl group or an amino-protecting group, Ring B: the following monocyclic or bicyclic ring which may contain an oxygen atom:
1) a nitrogen-containing saturated heterocyclic ring having 4 to 16 ring-forming atoms, or
2) a nitrogen-containing heterocyclic ring having one unsaturated bond and 4 to 16 ring-forming atoms, and Ring D: a saturated carbon ring having 4 to 8 ring-forming atoms, with the proviso that a nitrogen atom in the group R can become a quaternary ammonium salt accompanied by a substituent.

The compound (I) or its pharmaceutically acceptable salt, which is an effective ingredient of the pharmaceutical composition of the present invention, is characterized by its chemical structure in which, through a specific carbon chain or without it, a specific amine-based group or ring binds to the 2-position of either of a specific tricyclic condensed thiazole or a thiazole at the 4- or 5-position of which a benzene ring or a specific unsaturated heterocyclic group which is possibly substituted further has been substituted. It is also pharmacologically characterized by excellent 5-HT$_3$ receptor agonistic activities measured by using the contractile effects on the isolated colon from a guinea pig via a 5-HT$_3$ receptor as an index, independent from Von Bezold-Jarisch reflex.

The present invention also provides a specific compound represented by the following formula (II):

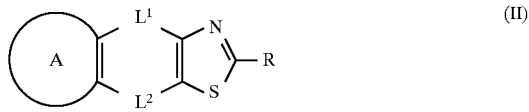

wherein each symbol represents the following meaning:

Ring A: the following ring which may be substituted by one or more substituents selected from the group consisting of a halogen atom, a lower alkyl group and a lower alkoxyl group,:
1) a benzene ring, or
2) a 5-membered or 6-membered unsaturated heterocyclic ring having one or two hetero atoms selected from the group consisting of a nitrogen atom, an oxygen atom and a sulfur atom, $L_1$ and $L_2$: one of them represents a single bond, and the other one an alkylene group having 1 to 4 carbon atoms or an alkenylene group having 2 to 5 carbon atoms, R: a group represented by one of the following formulas:

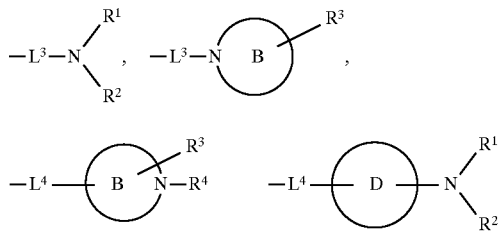

$L^3$: a lower alkylene group, $L^4$: a single bond or a lower alkylene group, $R^1$ and $R^2$: the same or different and individually a hydrogen atom, a lower alkyl group or an amino-protecting group, $R^3$: a hydrogen atom, a lower alkyl group, an oxo group or a protected or unprotected amino group, $R^4$: a hydrogen atom, a lower alkyl group, an aralkyl group or an amino-protecting group, Ring B: the following monocyclic or bicyclic ring which may contain an oxygen atom:
1) a nitrogen-containing saturated heterocyclic ring having 4 to 16 ring-forming atoms, or
2) a nitrogen-containing heterocyclic ring having one unsaturated bond and 4 to 16 ring-forming atoms, and Ring D: a saturated carbon ring having 4 to 8 ring-forming atoms, with the proviso that, when Ring A is a benzene ring or a pyridine ring, one of $L^1$ and $L^2$ represents a single bond and the other one represents an alkylene group having 1 to 4 carbon atoms or an alkenylene group having 2 to 5 carbon atoms, and that a nitrogen atom in the group R can be a quaternary ammonium salt accompanied by a substituent, or a pharmaceutically acceptable salt thereof.

The compound represented by the formula (II) or a pharmaceutically acceptable salt thereof is not disclosed specifically in the above-described JP-A-5-51318 so that it can be said that the compound is recognized as a novel compound which cannot be developed naturally based on the specifically-disclosed technique.

That is, the invention compound (II) has a characteristic in the chemical structure in which a specific amine-based group or ring binds to, through or not through a specific carbon chain, the 2-position of either a specific tricyclic condensed thiazole or a thiazole which has been substituted at the 4- or 5-position by a specific unsaturated heterocyclic ring other than a pyridine ring, said specific unsaturated heterocyclic ring is possibly substituted further.

The present invention further embraces an intermediate particularly useful for the preparation of the compound (I), (II) or a pharmaceutically acceptable salt thereof and relates to a thioamide derivative selected from the group consisting of (1-benzyl-3-pyrrolidine)carbothioamide, (1-benzyl-2 pyrrolidine)thioacetamide, 1-azabicyclo[2.2.1]-heptane-4-carbothioamide, 1-methyl-2-pyrrolidinone-4-carbothioamide and 1-azabicyclo[3.3.0]octane-3-carbothioamide or a salt thereof.

The present invention will hereinafter be described in detail.

In the definition for the formula of the present specification, the term "lower" as used herein means linear or branched carbon chain having 1 to 6 carbon atoms unless otherwise indicated.

Accordingly, the specific examples of the "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Of these groups, $C_1$–$C_4$ alkyl, particularly, $C_1$–$C_3$ alkyl groups are preferred.

Specific examples of "the lower alkylene group" represented by $L^3$ or $L^4$ include linear or branched $C_1$–$C_6$ alkylene groups, for example, methylene, ethylene, methylmethylene, trimethylene, 1-methylethylene, 2-methylethylene, tetramethylene, 1-methyltrimethylene, 2-methyltrimethylene, 3-methyltrimethylene, 1-ethylethylene, 2-ethylethylene, 1,2-dimethylethylene, propylmethylene, pentamethylene, 1-methyltetramethylene, 2-methyltetramethylene, 3-methyltetramethylene, 4-methyltetramethylene, 1-ethyltrimethylene, 2-ethyltrimethylene, 3-ethyltrimethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene and 4,4-dimethyltetramethylene. Of these groups, linear or branched $C_1$–$C_4$ alkylene, particularly linear or branched $C_1$–$C_3$ alkylene groups are preferred.

Specific examples of "the alkylene group having 1 to 4 carbon atoms" which is represented by one of $L^1$ and $L^2$ include those having 1 to 4 carbon atoms among the above-exemplified "lower alkylene groups". Of these, those having 1 to 3 carbon atoms, particularly 1 to 2 carbon atoms are preferred.

Examples of the "alkenylene group having 2 to 5 carbon atom" which is represented by one of $L^1$ and $L^2$ include linear or branched alkenylene groups such as vinylene, propenylene, 2-propenylene, 1-methylvinylene, 2-methylvinylene, 1-butenylene, 2-butenylene, 3-butenylene, 1,3-butadienylene, 1-methylpropenylene, 2-methylpropenylene, 3-methylpropenylene, 1-methyl-2-propenylene, 2-methyl-2-propenylene, 3-methyl-2-propenylene, 1-ethylvinylene, 2-ethylvinylene, 1-propylvinylene, 2-propylvinylene, 1-isopropylvinylene and 2-isopropylvinylene. Of these groups, a ring-constituting alkenylene chain composed of a $C_2$–$C_4$ alkenylene group, particularly, a ring-constituting alkenylene chain composed of a $C_2$ alkenylene group is preferred.

Examples of the "lower alkoxyl group" include linear or branched alkoxyl group having 1 to 6 carbon atoms, for example, methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, hexyloxy, isohexyloxy, 1-methylpentyloxy, 2-methylpentyloxy, 3-methylpentyloxy, 1,1-dimethylbutoxy, 1,2-dimethylbutoxy, 2,2-dimethylbutoxy, 1,3-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

Of these groups, methoxy, ethoxy, propoxy and isopropoxy groups are particularly preferred, with a methoxy group being more preferred.

"The aralkyl group" means the group in which any hydrogen atom of the above-described "lower aralkyl group" has been substituted by an aryl group, for example, phenyl or naphthyl. Specific examples include benzyl, phenethyl, 1-phenylethyl, 3-phenylpropyl, 2-phenylpropyl, 1-phenylpropyl, 1-methyl-2-phenylethyl, 4-phenylbutyl, 3-phenylbutyl, 2-phenylbutyl, 1-phenylbutyl, 2-methyl-3-phenylpropyl, 5-phenylpentyl, 4-phenylpentyl, 3-phenylpentyl, 2-phenylpentyl, 1-phenylpentyl, 3-methyl-4-phenylbutyl, 6-phenylhexyl, 5-phenylhexyl, 4-phenylhexyl, 3-phenylhexyl, 2-phenylhexyl, 1-phenylhexyl, 4-methyl-5-phenylpentyl, 1-naphthylmethyl, 2-naphthylmethyl, 2-(1-naphthyl)ethyl, 2-(2-naphthyl)ethyl, 1-(1-naphthyl)ethyl, 1-(2-naphthyl) ethyl, 3-(1-naphthyl)propyl, 3-(2-naphthyl)propyl, 2-(1-naphthyl)propyl, 2-(2-naphthyl)propyl, 1-(1-naphthyl) propyl, 1-(2-naphthyl)propyl, 1-methyl-2-(1-naphthyl)ethyl, 1-methyl-2-(2-naphthyl)ethyl, 4-(1-naphthyl)butyl, 4-(2-naphthyl)butyl, 3-(1-naphthyl)butyl, 3-(2-naphthyl)butyl, 2-(1-naphthyl)butyl, 2-(2-naphthyl)butyl, 1-(1-naphthyl) butyl, 1-(2-naphthyl)butyl, 2-methyl-3-(1-naphthyl)propyl, 2-methyl-3-(2-naphthyl)propyl, 5-(1-naphthyl)pentyl, 5-(2-naphthyl)pentyl, 4-(1-naphthyl)pentyl, 4-(2-naphthyl) pentyl, 3-methyl-4-(1-naphthyl)butyl, 3-methyl-4-(2-naphthyl)butyl, 6-(1-naphthyl)hexyl, 6-(2-naphthyl)hexyl, 5-(1-naphthyl)hexyl, 5-(2-naphthyl)hexyl, 4-methyl-5-(1-naphthyl)pentyl, 4-methyl-5-(2-naphthyl)pentyl, diphenylmethyl (benzhydryl) and trityl.

Examples of "the amino-protecting group" represented by $R^1$, $R^2$ or $R^4$ or the amino-protecting group in the "protected or unprotected amino group" represented by $R^3$ include aralkyloxycarbonyl groups, for example, benzyloxycarbonyl, p-methoxybenzyloxycarbonyl, p-methylbenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, 3,5-dimethoxybenzyloxycarbonyl and 3,4,5-trimethoxybenzyloxycarbonyl; lower alkoxycarbonyl groups, for example, ethoxycarbonyl, tert-butoxycarbonyl and tert-amyloxycarbonyl; aryloxycarbonyl groups, for example, phenoxycarbonyl; other urethane-type protecting groups, for example, p-biphenylisopropyloxycarbonyl and diisopropylmethyloxycarbonyl; acyl-based protecting groups, for example, acyl groups (e.g., $C_1$–$C_6$ alkanoyl groups such as formyl, acetyl, propionyl, butyryl, isobutyryl, valeryl, isovaleryl, pivaloyl and hexanoyl), trifluoroacetyl, phthalyl, tosyl, o-nitrophenylsulfinyl, p-methoxy-o-nitrophenylsulfonyl, benzoyl and chloroacetyl; and phthalimide group formed by a protecting group together with a nitrogen atom of the amino group.

Examples of "the halogen atom" include fluorine, chlorine, bromine and iodine atoms.

Specific examples of "the 5-membered or 6-membered unsaturated heterocyclic group having one or two hetero atoms selected from the group consisting of a nitrogen atom, an oxygen and a sulfur atom" which is a cyclic portion represented by Ring A include nitrogen-containing unsaturated heterocyclic rings, for example, pyrrole, pyrazole, imidazole, pyridine, pyrimidine, pyrazine and pyridazine; oxygen-containing unsaturated heterocyclic rings, for example, furan, 1,2-dioxole, 1,3-dioxole, pyran, 1,2-dioxine, 1,3-dioxine and 1,4-dioxine; sulfur-containing unsaturated heterocyclic ring, for example, thiophene, 1,2-dithiole, 1,3-dithiole, thiopyran, 1,2-dithiin, 1,3-dithiin and 1,4-dithin; unsaturated heterocyclic ring having two different hetero atoms, for example, oxazole, isoxazole, thiazole, isothiazole, 1,2-oxathiole, 1,3-oxathiole, 1,2-oxadine, 1,3-oxadine, 1,4-oxadine, 1,2-thiazine, 1,3-thiazine, 1,4-thiazine, 1,2-thioxathiin and 1,4-oxathiin; and the above-exemplified rings of structural isomerism which have indicated hydrogen at a different position. Incidentally, rings which are different in the position of the hetero atom will hereinafter be omitted from the description when they have an expression only different in the binding position of the hetero atom or they only differ in the position of indicator hydrogen. It is, however, to be noted that these rings are included in the following rings.

Of the above-exemplified heterocyclic ring portion of Ring A, pyridine, furan, thiophene and thiazole rings are preferred.

Examples of the "nitrogen-containing saturated heterocyclic having 4 to 16 ring-forming atoms, which may contain an oxygen atom and is monocyclic or bicyclic" represented by Ring B include nitrogen-containing saturated heterocyclic rings each of which has one or more than one, preferably one to three nitrogen atoms, may be condensed, may form a cross-linkage and is a monocyclic or bicyclic ring, for example, azetidine, diazetidine, pyrrolidine, pyrazolidine, imidazolidine, tetrahydrotriazole, piperidine, piperazine, hexahydrotriazine, hexahydroazepine, hexahydrodiazepine, azocine, octahydroindole, octahydroisoindole, octahydrobenzopyrazole, decahydroquinoline, decahydroisoquinoline, decahydrophthalazine, decahydroquinoxaline, decahydrocinnoline, pyrrolididine (1-azabicyclo[3.3.0]octane), quinucridine (1-azabicyclo[2.2.2]octane), 1-azabicyclo-[2.2.1]heptane, 7-azabicyclo[2.2.1]heptane, 1-azabicyclo-[3.2.1]octane, 8-azabicyclo[3.2.1]octane, 6-azabicyclo-[3.2.1]octane, 2-azabicyclo[2.2.2]octane, 1-azabicyclo-[3.2.2]nonane, 1-azabicyclo[3.3.1]nonane, 9-azabicyclo-[3.3.1]nonane, 1-azabicyclo[4.2.1]nonane, 1-azabicyclo-[4.3.1]decane, 10-azabicyclo[4.3.1]decane, 1-azabicyclo-[4.4.0]decane and 3,9-diazabicyclo[3.3.1]nonane; and nitrogen-containing saturated heterocyclic rings each of which contains as a hetero atom nitrogen and oxygen atoms, may be condensed, may form cross-linkage and is a monocyclic or bicyclic ring, for example, oxazolidine, isoxazolidine, morpholine, hexahydrooxazepine, octahydrobenzoxazole, octahydrobenzisoxazole, 1-aza-3-oxabicyclo[2.2.2]octane and 9-aza-3-oxabicyclo[3.3.1]nonane.

Of these groups, preferred examples of the nitrogen-containing saturated heterocyclic ring represented by Ring B include pyrrolidine, piperidine, piperazine, morpholine, pyrrolididine, quinucridine, 1-azabicyclo[2.2.1]heptane and 8-azabicyclo[3.2.1]octane, with pyrrolidine, pyrrolididine and 1-azabicyclo[2.2.1]heptane being most preferred.

Examples of the "nitrogen-containing heterocyclic group having one unsaturated bond and 4 to 16 ring-forming atoms, which may contain an oxygen atom, is monocyclic or bicyclic and contain one unsaturated bond" include nitrogen-containing heterocyclic rings which contain one unsaturated bond, is a monocyclic or bicyclic ring and have 4 to 16 ring-forming atoms", for example, azetine, diazetine, pyrroline, pyrazoline, imidazoline, dihydrotriazoline, tetrahydropyridine, tetrahydropyrazine, tetrahydrotriazine, tetrahydroazepine, tetrahydrodiazepine, hexahydroazocine, hexahydroindole, hexahydroisoindole, hexahydrobenzimidazole, hexahydrobenzopyrazole, octahydroquinoline, octahydroisoquinoline, octahydrophthalazine, octahydroquinoxaline, octahydroquinazoline and octahydrosinnoline; and nitrogen-containing heterocyclic groups each of which contains nitrogen and oxygen atoms, have one saturated bond, is a monocyclic or bicyclic ring and have 4 to 16 ring-forming atoms, for example, oxazoline, isoxazoline, dihydrooxadine, hexahydrobenzoxazoline and hexahydrobenzisoxazoline. The above exemplified rings contain those of structural isomerism which are different in the position of the double bond.

Of these, a tetrahydropyridine ring is given as a preferred example.

Examples of the "saturated carbon ring having 4 to 8 ring-forming atoms" represented by Ring D include cyclobutane, cyclopentane, cyclohexane, cycloheptane and cyclooctane. Of these groups, a cyclohexane ring is preferred.

Compounds (I) or (II) according to the present invention or an intermediate thereof form a corresponding acid addition salt. The present invention embraces pharmaceutically acceptable salts of the compounds (I) and (II) and salts of a thioamide compound, which is the intermediate. Examples of such a salt include acid addition salts of a mineral acid, for example, hydrochloric acid, hydrobromic acid, hydroiodic acid, sulfuric acid, nitric acid or phosphoric acid; and acid addition salts of an organic acid, for example, formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid or glutamic acid.

These compounds can be in the form of a quaternary ammonium salt. Specific examples of the quaternary ammonium salt include salts obtained by reacting with a lower alkyl halide, lower alkyl trifurate, lower alkyl tosylate or benzyl halide, with salts of methyl iodide and benzyl chloride being preferred.

In the compound according to the present invention, a carbon atom of Ring B or Ring D sometimes binds to $L^4$ and there exists an optical isomer when the compound contains an asymmetric carbon atom, depending on the kind of the lower alkylene chain. The compound of the present invention has various isomers, for example, a tautomer which is based on the existence of an oxo group or a stereoisomer of endo-exo isomerism which is based on the cross-linking ring. The present invention embrace these isomers which have been isolated, and also their mixtures.

The compound of the present invention may be isolated in the form of various solvates, for example, hydrate or ethanol solvate or sometimes isolated as a substance of various polymorphism forms. The present invention embrace all of these substances.

Among the compounds(I) which is an effective ingredient of the pharmaceutical composition of the present invention, particularly preferred compounds are those specified as the compound (II) and recognized as novel compounds.

Of the compounds (II) according to the present invention, examples of the particularly preferred compound include:

(1) a compound represented by the following formula (IIa):

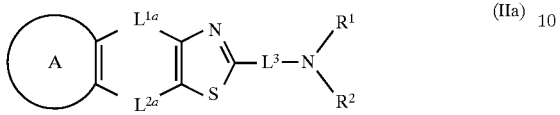

wherein Ring A, L³, R¹ and R² have the meanings as defined above, and one of $L^{1a}$ and $L^{2a}$ represents a single bond and the other one represents an alkylene group having 1 to 4 carbon atoms or an alkenylene group having 2 to 5 carbon atoms, (2) a compound represented by the following formula (IIb):

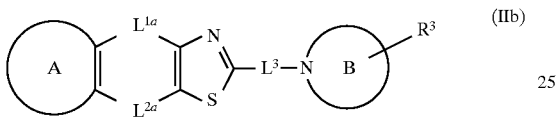

wherein Ring A, $L^{1a}$, $L^{2a}$, $L^3$, Ring B and $R^3$ have the same meanings as defined above, (3) a compound represented by the following formula (IIc):

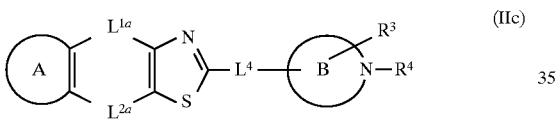

wherein Ring A, $L^{1a}$, $L^{2a}$, $L^4$, Ring B, $R^3$ and $R^4$ have the same meanings as defined above, (4) a compound represented by the following formula (IId):

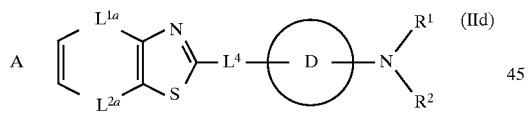

wherein Ring A, $L^{1a}$, $L^{2a}$, $L^4$, Ring D, $R^1$ and $R^2$ have the same meanings as defined above, and (5) a compound represented by the following formula (IIe):

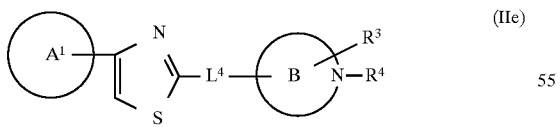

wherein $L^4$, Ring B, $R^3$ and $R^4$ have the same meanings as defined above, Ring $A^1$ represents a 5-membered or 6-membered unsaturated heterocyclic ring having one or two hetero atoms selected from the group consisting of a nitrogen atom, an oxygen atom and a sulfur atom and which may be substituted by one or more substituents selected from the group consisting of a halogen atom, a lower alkyl group and a lower alkoxyl group, with the proviso that a pyridine ring is excluded; and pharmaceutically acceptable salts thereof. More preferred examples include:

(6) a compound represented by the following formula (IIIa):

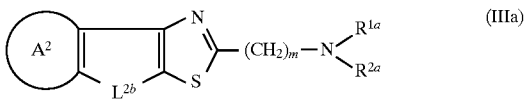

wherein symbols represent the following meanings:

Ring $A^2$: a benzene ring which may be substituted by one or more substituent selected from the group consisting of a halogen atom, a lower alkyl group and a lower alkoxyl group, $L^{2b}$: an alkylene group having 1 to 4 carbon atoms, m: an integer of 1 to 6, $R^{1a}$ and $R^{2a}$: the same or different and individually represent a hydrogen atom or a lower alkyl group, with the proviso that $R^{1a}$ and $R^{2a}$ may be combined together with an adjacent nitrogen atom to form a phthalimide group, (7) a compound represented by the following formula (IIIb):

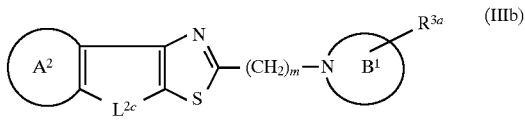

wherein Ring $A^2$ and m have the same meanings as defined above and the other symbols have the following meanings:

$L^{2c}$: an alkylene having 1 to 4 carbon atoms or a vinylene group, $R^{3a}$: a hydrogen atom, an oxo group, or an amino group which may be protected by an acyl group, and Ring $B^1$: a nitrogen-containing saturated heterocyclic ring which may contain an oxygen atom, is monocyclic or bicyclic and have 4 to 8 ring-forming atoms, (8) a compound represented by the following formula (IIIc):

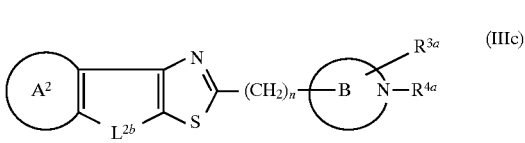

wherein Ring $A^2$, $L^{2b}$, $L^{3a}$ and Ring B have the same meanings as defined above and the other symbols have the following meanings:

$R^{4a}$: represents a hydrogen atom or a lower alkyl, aralkyl, lower alkoxycarbonyl, aralkyloxycarbonyl, aryloxycarbonyl or acyl group, and n: 0 or an integer of 1 to 6, (9) a compound represented by the following formula (IIId):

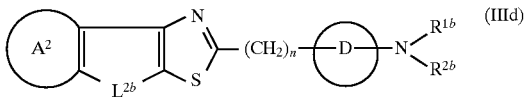

wherein Ring $A^2$, $L^{2b}$, n and Ring D have the same meanings as defined above and $R^{1b}$ and $R^{2b}$ are the same or different and individually represent a hydrogen atom or a lower alkyl group, and

(10) a compound represented by the following formula (IIIe):

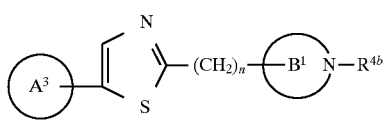

wherein n and Ring $B^1$ have the same meanings as defined above and the other symbols have the following meanings:

Ring $A^3$: a 5-membered or 6-membered unsaturated heterocyclic ring having one or two hetero atoms selected from the group consisting of a nitrogen atom, an oxygen atom and a sulfur atom, with the proviso that a pyridine ring is excluded, and $R^{4b}$: a hydrogen atom, a lower alkyl group or an aralkyl group;

and pharmaceutically acceptable salts thereof. Compounds represented by the formula (IIIc) in which Ring B represents a 1-azabicyclo[3.3.0]octane ring (pyrrolididine ring), 1-azabicyclo[2.2.1]heptane ring or pyrrolidine ring and pharmaceutically acceptable salts thereof are more preferred.

Examples of the most preferred compounds include:
(1) 2-(3-Pyrrolidinyl)-8H-indeno[1,2-d]thiazole,
(2) (3R*,5S*)-3-(8H-indeno[1,2-d]thiazole-2-yl)-1-azabicyclo[3.3.0]octane,
(3) 2-(3-pyrrolidinylmethyl)-8H-indeno[1,2-d]thiazole,
(4) 4-(8H-indeno[1,2-d]thiazol-2-yl)-1-azabicyclo[2.2.1]heptane,
(5) (S)-2-(3-pyrrolidinyl)-8H-indeno[1,2-d]thiazole,
(6) (3R,5S)-3-(8H-indeno[1,2-d]thiazole-2-yl)-1-azabicyclo[3.3.0]octane,
(7) (3S,5R)-3-(8H-indeno[1,2-d]thiazole-2-yl)-1-azabicyclo[3.3.0]octane,
(8) 2-(1-methyl-3-pyrrolidinyl)-8H-indeno[1,2-d]thiazole, and
(9) 5-[(8H-indeno[1,2-d]thiazol-2-yl)methyl]-1-azabicyclo[3.3.0]octane, and pharmaceutically acceptable salts thereof.

The intermediates useful in the present invention are thioamide derivatives selected from the group consisting of (1-benzyl-3-pyrrolidine)carbothioamide, (1-benzyl-2 pyrrolidine)thioacetamide, 1-azabicyclo[2.2.1]heptane-4-carbothioamide, 1-methyl-2-pyrrolidinone-4-carbothioamide and 1-azabicyclo[3.3.0]octane-3-carbothioamide and salts thereof. Particularly useful intermediates are thioamide derivatives having a 1-azabicyclo[3.3.0]octane ring or a pyrrolidine ring, and salts thereof.

(Preparation Process)

The compounds (I) and (II) according to the present invention and pharmaceutically acceptable salts thereof can be prepared by making use of their characteristics based on their basic skeleton or the kind of the substituent and by applying various synthetic methods. Upon preparation, it is sometimes effective as the preparation technique to have substituted the amino group or the like of the invention compound by a proper protecting group as needed, in other words, a functional group which is easily convertible to an amino group or the like. Examples of such a protecting group include the above-described amino protecting groups and those described in the 2nd edition of "*Protecting groups in Organic Synthesis*" by Greene and Wuts. They can be used appropriately according to reaction conditions. Furthermore, it is also possible to use functional groups, other than those protecting groups, such as a nitro group which can be converted easily to an amino group or the like.

The following are representative preparation process of the compound of the present invention.

First Preparation Process (ring-closing reaction)

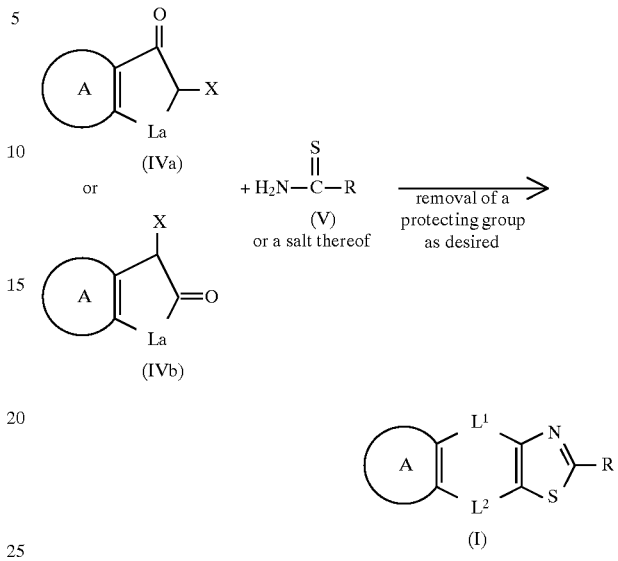

wherein Ring A, $L^1$, $L^2$ and R have the same meanings as defined above, La represents an alkylene group having 1 to 4 carbon atoms or an alkenylene group having 2 to 5 carbon atoms and X represents a halogen atom.

The compound (I) according to the present invention can be prepared by reacting an α-halogenoketone compound represented by the formula (IVa) or (IVb) with a thioamide compound represented by the formula (V) or a salt thereof to cause ring closure, and then by removing the protecting group as desired.

Here, examples of the halogen atom represented by X include iodine, bromine and chlorine.

It is advantageous to react the compound (IVa) or (IVb) with (V) in amounts corresponding to the reaction, or to react them by adding one of them in an excessive molar amount in an organic solvent inert to the reaction, for example an alcoholic solvent such as isopropanol, methanol or ethanol, or an aqueous alcoholic solvent, at a temperature from room temperature to under heating, preferably while heating under reflux.

The protecting group is removed in a conventional manner, though it may be different depending on the kind of the protecting group. For the removal of an acyl-type protecting group, for example, $C_1$–$C_6$ alkanoyl or benzoyl group, the hydrolysis in the presence of an acid or alkali is suited. For the removal of a substituted or unsubstituted benzyloxycarbonyl group, on the other hand, catalytic reduction is suited but, acid treatment with hydrobromic acid/acetic acid, hydrobromic acid/trifluoroacetic acid or hydrofluoric acid is employed depending on the case. For the removal of a urethane type protecting group such as ethoxycarbonyl or tert-butoxycarbonyl, acid treatment with hydrobromic acid/acetic acid, trifluoroacetic acid, hydrochloric acid, hydrochloric acid/acetic acid or hydrochloric acid/dioxane is advantageous. For the removal of a phthaloyl group, treatment with methylamine or hydrazine is suited. An alkyl group or aralkyl group can be removed by dealkylation reaction in a conventional manner.

Incidentally, the starting compound (V) can be prepared in the general technique from a corresponding amide. Alternatively, as shown below by the reaction scheme, it can also be prepared by acting a reaction agent such as O,O-dialkyl dithiophosphate or hydrogen sulfide on a corresponding nitrile (VI) as a starting material at room temperature or under heating. When the dithiophosphate ester is acted, it is advantageous to carry out reaction in an organic solvent inert to the reaction, such as ethyl acetate, under acidic conditions, for example, hydrochloric-acid-added conditions. When hydrogen sulfide is acted, it is advantageous to conduct reaction in an organic solvent such as methanol or ethanol in the presence of ammonia, sodium or potassium alcoholate.

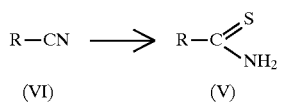

The corresponding nitrile compound (VI) which is the starting compound of the above reaction can be prepared as shown in the reaction scheme which will be described below. For example, when a corresponding halide or sulfonate (VII) is used as a starting material, the nitrile compound can be prepared by acting a cyano-introducing agent such as sodium cyanide on the starting material in an organic solvent inert to the reaction such as dimethyl sulfoxide. When a corresponding oxo compound (VIIIa) is used as a starting material, on the other hand, the compound is treated with Horner-Emmons reagent such as O,O-dialkyl cyanomethylphosphonate in an organic solvent inert to the reaction, such as dioxane, preferably in the presence of a base such as sodium hydride to convert the compound to a cyano methylene derivative (IX), followed by reduction treatment such as catalytic hydrogenation using palladium-carbon or the like as a catalyst in an organic solvent such as alcohol. Alternatively, the nitrile compound (VI) can also be prepared by treating an oxo compound (VIIIb), which is employed a starting material, with a base such as potassium tert-butoxide in the presence of a cyano-introducing agent such as p-toluenesulfonylmethylisocyanide and, preferably in the presence of an alcohol such as ethanol, in an organic solvent inert to the reaction, such as dimethoxyethane. It is also possible to prepare a nitrogen-containing heterocyclic nitrile compound (VI) by employing as a starting material a secondary amine (X), such as 2-pyrrolidine methanol, having a hydroxyalkyl group; reacting α,β-unsaturated nitrile such as acrylonitrile with the secondary amine in an organic solvent inert to the reaction such as ethanol to obtain a cyanoethylamine derivative (XI); acting an organic sulfonic acid halide such as mesyl chloride on the resulting cyanoethylamine derivative in an organic solvent inert to the reaction such as toluene in the presence of a base such as triethylamine to convert the hydroxyl group into a reaction active group; and treating with a base such as potassium tert-butoxide to cause ring closure. The nitrile compound can also be prepared from the corresponding carboxylic acid derivative (XII) such as carboxylic acid amide in accordance with a generally employed method.

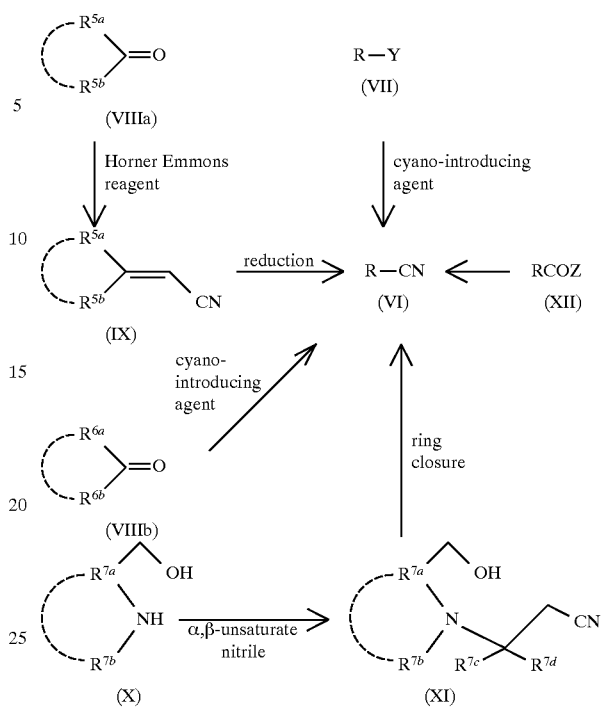

wherein R has the same meaning as described above and other symbols have the following meanings:

Y: a halogen atom or an organic sulfonic acid residue, $R^{5a}$ and $R^{5b}$: the same group as R which is represented by:

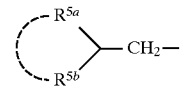

$R^{6a}$ and $R^{6b}$: the same group as R represented by:

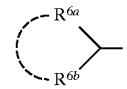

$R^{7a}$, $R^{7b}$, $R^{7c}$ and $R^{7d}$: the same group as R represented by:

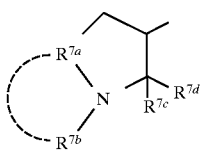

Z: a hydroxyl group or a carboxylic acid derivative residue.

The starting compounds (IVa) and (IVb) used in the above first preparation process contain a novel compound and it can be prepared by acting a halogenating agent such as bromine, chlorine gas, copper (II) bromide and perhalide on a corresponding ketone compound in an organic solvent such as ether or acetic acid.

Secondary Preparation Process (alkylation)

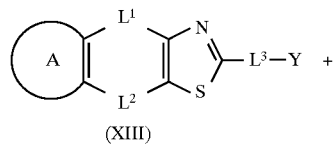

(XIII)

(XIVa)

or

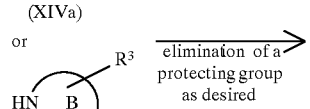

(XIVb)

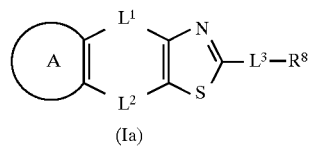

(Ia)

wherein Ring A, $L^1$, $L^2$, $L^3$, $R^1$, $R^2$, Ring B and $R^3$ have the same meanings as described above, Y represents a halogen atom or an organic sulfonic acid residue and $R^8$ is a group represented by the following formula:

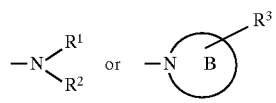

in which $R^1$, $R^2$, Ring B and $R^3$ have the same meanings above.

Among the compounds according to the present invention, the heterocyclic alkylthiazole derivative which is represented by the formula (Ia) and contains a C—N bond can be prepared by reacting a halide or sulfonate represented by the formula (XIII) with an amine represented by the formula (XIVa) or (XIVb), followed by the removal of a protecting group as desired.

Examples of the halogen atom include the above-exemplified ones and examples of the organic sulfonic acid residue include alkylsulfonyloxy groups such as methanesulfonyloxy and ethansulfonyloxy, and arylsulfonyloxy groups such as benzenesulfonyloxy and toluenesulfonyloxy (particularly, p-toluenesulfonyloxy).

The reaction between the compound (XIII) and the compound (XIVa) or (XIVb) is conducted in amounts corresponding to the reaction or with one of them in an excessive molar amount. It is advantageous to conduct reaction at a temperature under cooling to room temperature, at a temperature from room temperature to under heating or while heating under reflux, depending on the starting compound, in a solvent inert to the reaction such as dimethylformamide, dimethyl sulfoxide, ethyl ether, tetrahydrofuran, dioxane, acetone, methyl ethyl ketone, methanol, ethanol, methylene chloride, dichloroethane or chloroform, optionally in the presence of a base such as pyridine, picoline, dimethylaniline, N-methylmorpholine, trimethylamine, triethylamine, sodium hydroxide, potassium carbonate, sodium carbonate, sodium bicarbonate, sodium hydride or potassium hydroxide. The protecting group is removed in a manner similar to the above first preparation process.

Third Preparation Process (reduction of lactam or amide)

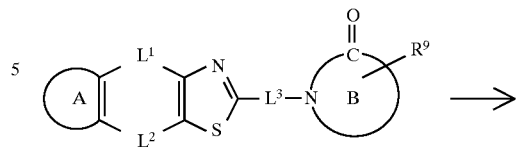

(Ib)

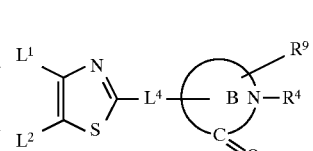

(Ic)

or

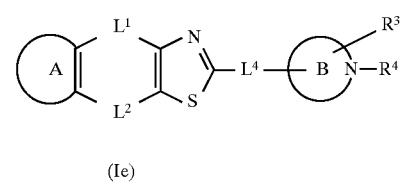

(Id)

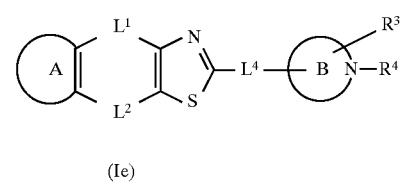

(Ie)

or

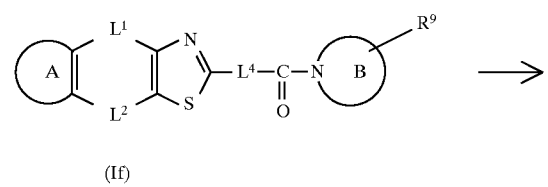

(If)

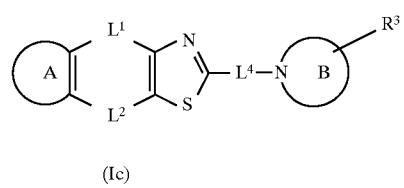

(Ic)

wherein Ring A, $L^1$, $L^2$, $L^3$, $L^4$, Ring B and $R^4$ have the same meanings as described above, $R^9$ represents a hydrogen atom or an amino group which may be protected, $L^4$ represents a $C_{1-5}$ alkylene or $C_{2-5}$ alkenylene group with the proviso that the formula:

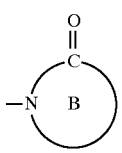

represents a nitrogen-containing saturated heterocyclic group having a lactam structure.

Among the compounds according to the present invention, the heterocyclic alkylthiazole derivative of the formula (Ic) or (Ie) can also be prepared by reducing a corresponding lactam (Ib), (Id) or (If).

Upon reaction, it is desired to use a hydrogenated compound of boron or aluminum, a borane complex such as diborane or borane-teterahydrofuran complex, or a reduction reagent, for example, lithium aluminum hydride, sodium bis(2-methoxyethoxy)aluminum hydride or diisobutylaluminum hydride in an amount corresponding to the reaction or in an excessive amount and to conduct reaction at a temperature from low temperature to under heating, preferably under heating and reflux in a solvent inert to the reaction such as tetrahydrofuran, ethyl ether, dioxane, 1,2-dimethoxyethane, benzene or toluene. Alternatively, a corresponding lactam can be reduced by using sodium borohydride as a reduction reagent subsequent to the treatment with triethyloxonium tetrafluoroborate or phosphorus oxychloride.

Other Preparation Processes

Among the compounds according to the present invention, the compound in which at least one of $R^1$ and $R^2$ or $R^4$ represents an acyl-type protecting group, or $R^3$ represents an amino group protected with a protecting group can be prepared by N-acylation (amidation) of a corresponding amine or its salt and a corresponding carboxylic acid or its activated derivative in a manner known in the art.

Among the compounds according to the present invention, the compound in which at least one of $R^1$ and $R^2$ or $R^4$ represents a lower alkyl or aralkyl group can be prepared by using a corresponding primary or secondary amine derivative as a starting material and conducting N-alkylating reaction, reductive alkylating reaction with a carbonyl compound or reductive reaction after N-acylation. The N-alkylating reaction can be conducted using a corresponding primary or secondary amine derivative and an alkyl halide or alkyl sulfonate under the conditions similar to those of the second preparation process. The reductive alkylating reaction with a carbonyl compound can be effected by treating a corresponding primary or secondary amine derivative with the carbonyl compound such as acetone and a suitable reducing agent such as sodium triacetoxyborohydride or sodium cyanoborohydride in an organic solvent inert to the reaction, such as methylene chloride, preferably in the presence of an acid catalyst such as acetic acid; or by conducting reductive treatment such as catalytic hydrogenation using palladium-carbon as a catalyst. It is also possible to conduct general reductive methylation reaction using formalin and formic acid. Reductive reaction after N-acylation, on the other hand, can be conducted by N-acylating a corresponding amine and a carboxylic acid or its active derivative in a manner known in the art, followed by reduction under the conditions similar to those of the third preparation process.

A compound in which the nitrogen atom in R forms a quaternary ammonium can be prepared by reacting a corresponding tertiary amine with an alkyl halide or the like in a manner known in the art.

Among the compounds of the present invention, the compound wherein R represents —$L^3$—$NR^1R^2$ or

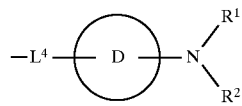

can be prepared by reducing a nitro group of a corresponding nitro-substituted thiazole derivative in a manner known in the art and then, converting the substituent on the nitrogen atom as desired.

Among the compounds according to the present invention, the compound wherein Ring B represents a 1,2,3,5-tetrahydropyridine ring can be prepared by reacting an alkylating agent such as benzyl halide with a corresponding pyridine compound in a manner known in the art to obtain its pyridinium salt, reducing the salt with a suitable reducing agent such as sodium borohydride and converting the substituent on the nitrogen atom as desired.

Among the compounds according to the present invention, a saturated heterocyclic compound can be obtained by reducing a starting material, that is, a corresponding nitrogen-containing heterocyclic compound having one unsaturated bond in Ring B.

The compounds (I) of the present invention thus prepared are each isolated as a free compound, its salt, hydrate or solvate, etc., followed by purification. Pharmaceutically acceptable salts of the invention compound (I) can also be prepared by subjecting them to the general salt-forming reaction.

Isolation and purification may be carried out by employing general chemical procedures such as extraction, fractional crystallization, recrystallization and various types of fractional chromatography.

Various isomers can be isolated in a manner known in the art, making use of the physicochemical difference between isomers. For example, a racemic compound can be lead to a stereochemically pure isomer by a general racemic resolution [e.g., a method of carrying out optical resolution by converting the isomer into a diastereomeric salt with a generally employed optically active acid (tartaric acid or the like)]. A mixture of diastereomers can be separated in a manner known in the art, for example, fractional crystallization or chromatography.

An optically active compound can also be prepared by employing a suitable starting compound which is optically active.

Industrial Applicability

The compound of the present invention shows excellent 5-$HT_3$ receptor agonistic activity, especially, in terms of the contractile effects in the isolated guinea pig colon. The followings describe such activities together with their measuring methods.

1) 5-$HT_3$ receptor agonistic activity

Distal colons were excised from male Hartley guinea pigs (500 to 800 g) to prepare strips of about 20 mm.

Each strip was longitudinally suspended in an organ bath, and contractile response was isometrically measured.

5-HT caused a dose-dependent contraction within its concentration range of 0.1 to 30 $\mu$M and showed the maximal response at 10 to 30 $\mu$M (the action of 5-HT is mediated via the 5-$HT_3$ receptor: *J. Pharmacol. Exp. Ther.*, 259, 15–21, 1991).

Activity of each compound is expressed by relative value in comparison with the activity of 5-HT in each specimen.

The max. response is indicated as percentage of the maximal response by each compound when the maximal contraction by 5-HT is defined as 100%.

The relative potency is shown by relative $EC_{50}$ value for each compound based on the standard value (1) of that of 5-HT.

$$\left(\text{Relative Potency} = \frac{EC_{50} \text{ of 5-HT}}{EC_{50} \text{ of the compound}}\right)$$

| | Max. response | Relative potency |
|---|---|---|
| Compound of Ex. 9 | 75 | ½ |
| Compound of Ex. 46 | 52 | ½ |
| Compound of Ex. 52 | 77 | 22 |
| Compound of Ex. 59 | 45 | ⅓ |
| Compound of Ex. 66 | 57 | 144 |
| Compound of Ex. 70 | 23 | 4 |
| Compound of Ex. 71 | 51 | 2 |

(1) The compounds according to the present invention showed contractile effects on the isolated colon from a guinea pig at 300 μm or lower in a concentration depending manner.

The compounds of the present invention include those showing the effects of 70% or more of the maximum reaction of 5-HT and also those exhibiting contractile effects at a dose of ½ to ¹⁄₁₀₀ or smaller in comparison with 5-HT.

(2) The contractile effects of the invention compound on the isolated colon excised from a guinea pig were competed with those of 0.3 μm of the compound disclosed in Example 44 in the unexamined published Japanese patent application 3-223278 which is a selective 5-HT$_3$ receptor antagonist.

According to the above results, it was confirmed that the contractile effects of the invention compound on the colon were exhibited through 5-HT$_3$ receptor effects.

These results indicate that the invention compound is a potent 5-HT$_3$ receptor agonist.

2) Facilitation of defecation in rat

In the male Wistar rat (200–300 g), facilitating effects on defecation by stimulation of 5-HT$_3$ receptor [Miyata et al., J. Pharmacol. Exp. Ther., 261, 297 (1992)] were studied. The compound (10 mg/kg) was subcutaneously administered to the rat and the number of feces excreted for four hours after the administration was counted.

The compound obtained in Example 52 exhibited facilitating effect on defecation.

In this connection, the present invention also includes certain compounds which have 5-HT$_3$ receptor antagonistic activity, and such compounds should be regarded as another embodiment of the present invention. These compounds seem to be applicable to the medicinal use disclosed by the present inventors in relation to tetrahydrobenzimidazole derivatives, for example, in the unexamined published Japanese patent application No. 3-223278, such as inhibition or emesis caused by carcinostatic agents such as cisplatin and the like or radiation exposure, and prevention and treatment of migraine headache, complex headache, trigeminal neuralgia, anxiety symptoms, gastroin-testinal motility disorder, peptic ulcer, irritable bowel syndrome and the like.

The compound (I) according to the present invention or a salt, solvate or hydrate thereof acts specifically to a neuronic 5-HT$_3$ receptor of the intestinal nerve so that it is useful for the treatment of digestive tract disorders, more specifically, senile constipation, atonic constipation, rectal constipation, acute and chronic gastritis, gastric and duodenal ulcer, gastric neurosis, gastroptosis, reflux esophagitis, pseudoileus, non-ulcer dyspepsia, abdominal indefinite complaint, gastrointestinal dyskinesia caused by the diseases such as diabetes and the like, gastrointestinal function insufficiency after anesthesia and operation, gastric retention, dyspepsia and meteorism. It can also be used for the therapeutic treatment for the diseases caused by pancreatic insufficiency such as fat absorption insufficiency.

In addition, the compound according to the present invention is useful for the treatment of the symptoms such as mental disorder (for example, schizophrenia and depression), anxiety, disturbance of memory, dementia and extrapyramidal disorders.

Furthermore, the compound according to the present invention is usable for the treatment of dysuria accompanying urinary obstruction, ureterolith or prostatic hypertrophy.

A pharmaceutical composition comprising the compound of the present invention as an effective ingredient is formulated into tablets, powders, fine granules, granules, capsules, pills, liquid preparations, injections, suppositories, ointment or plasters by adding one or more generally used pharmaceutically acceptable additives such as carrier and excipient. It is administered orally or parenterally.

Clinical dose of the invention compound is appropriately determined in consideration of the symptoms, body weight, age, sex and the like of the patient to be applied. It is generally administered orally in an amount of 0.1–100 mg/day per adult once or in several portions. Since the dose may vary depending on various conditions, there are cases where sufficient effects can be obtained in a dose smaller than the above range.

As a solid composition of the invention compound for the oral administration, tablets, powders, granules and the like can be used. For preparation of such a solid composition, one or more active substances are mixed with at least one inert diluent, for example, lactose, mannitol, dextrose, hydroxypropylcellulose, microcrystalline cellulose, starch, polyvinylpyrrolidone and magnesium metasilicate aluminate. In the composition, additives other than the above inert diluent, for example, a lubricant such as magnesium stearate, a disintegrator such as cellulose calcium glycolate, a stabilizer such as lactose, a solubilizing agent or a solubilization aid such as glutamic acid or aspartic acid in a manner known in the art. A tablet or pill may be coated at need with a film of a gastric or enteric substance such as sucrose, gelatin, hydroxypropylcellulose, hydroxypropylmethylcellulose phthalate.

The liquid composition for the oral administration contain a pharmaceutically acceptable emulsifying agent, solution, suspending agent, syrup, elixir or the like and also a generally employed inert diluent such as purified water and ethanol. The composition may contain, in addition to the inert diluent, an auxiliary agent such as a solubilizing agent, a solubilization aid, a wetting agent, and a suspending agent, a sweetener, a flavoring agent, aroma and an antiseptic agent.

The injection for parenteral administration contains sterile aqueous or nonaqueous solution, a suspending agent or an emulsifying agent. Examples of the diluent for the aqueous solution or suspending agent include distilled water for injection and physiological saline. Examples of the diluent for the non-aqueous solution or suspending agent include polypropylene glycol, polyethylene glycol, vegetable oils such as olive oil, alcohols such as ethanol, and "Polysolvate 80" (trade name). The composition may further contain an isotonicity agent, antiseptic agent, wetting agent, emulsifying agent, dispersing agent, stabilizer (for example, lactose) and/or solubilizing agent or solubilization aid. They are sterilized by, for example, filtration through a bacteria-retaining filter, incorporation of a sterilizer or irradiation. Alternatively, a sterile solid composition which has been prepared in advance is used after dissolving it in sterile water or a sterile injection solvent.

Best Mode for Carrying Out the Invention

Hereinafter, the present invention is described in more detail by way of Formulation Example and Examples.

However, this invention should not be construed as being limited to these Examples.

Some of the starting compounds of the present invention are novel substances. The preparation of the starting compounds are shown as Reference Examples.

Formulation Example (tablet)

| Composition | 20 mg tablet |
|---|---|
| Invention compound | 20 mg |
| Lactose | 75 |
| Corn starch | 16 |
| Hydroxypropylcellulose | 4.5 |
| Carboxymethylcellulose calcium | 8.8 |
| Magnesium stearate | 0.7 |
| Total | 120 mg |
| 20 mg tablet | |

Using a fluidized granulation and coating apparatus, 100 g of the invention compound, 375 g of lactose and 80 g of corn starch were uniformly mixed. Then, granulation was carried out with spraying 225 g of a 10% hydroxypropylcellulose solution. After drying, the resulting granules were passed through a 20-mesh sieve, followed by the addition of 19 g of carboxymethylcellulose calcium and 3.5 g of magnesium stearate. After mixing, the resulting mixture was tabletted into a 120-mg tablet using a rotary tabletting machine with a 7 mm×8.4 R punch.

REFERENCE EXAMPLE 1

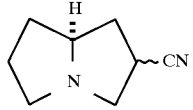

In 13 ml of ethanol, 4.71 g of (S)-2-pyrrolidinemethanol was dissolved, followed by the addition of 4.6 ml of acrylonitrile. The resulting mixture was heated under reflux for 2 hours. After the solvent was evaporated, the residue was dissolved in 70 ml of toluene, followed by the addition of 13 ml of triethylamine under ice-cooling. To the resulting mixture, 4.3 ml of methanesulfonyl chloride was added dropwise, followed by stirring at 0° C. for 10 minutes and then at room temperature for 30 minutes. After the addition of 15.7 g of potassium tert-butoxide, the mixture was stirred at room temperature for 16 hours. Water was added to the reaction mixture, and the toluene layer was separated and dried over anhydrous sodium sulfate. The solvent was evaporated and the resulting residue was subjected to silica gel column chromatography, whereby 5.22 g of (5S)-1-azabicyclo[3.3.0]octane-3-carbonitrile was obtained as a diastereomer mixture from the fraction eluted with chloroform-methanol-29% aqueous ammonia (100:10:1).

Mass spectrum (m/z): 136 (M$^+$)

Compounds of Reference Examples 2–4 were obtained by the same manner as described in Reference Example 1.

REFERENCE EXAMPLE 2

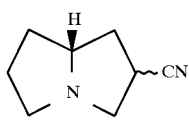

(5R)-1-Azabicyclo[3.3.0]octane-3-carbonitrile
Starting compound
(R)-2-Pyrrolidinemethanol
Mass spectrum (m/z): 136 (M$^+$)

REFERENCE EXAMPLE 3

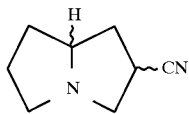

1-Azabicyclo[3.3.0]octane-3-carbonitrile
Starting compound
(RS)-2-Pyrrolidinemethanol
Mass spectrum (m/z): 136 (M$^+$)

REFERENCE EXAMPLE 4

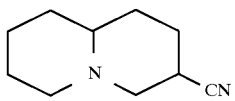

1-Azabicyclo[4.4.0]decane-3-carbonitrile
Starting compound
2-(2-Hydroxyethyl)piperidine
Mass spectrum (m/z): 164 (M$^+$)

REFERENCE EXAMPLE 5

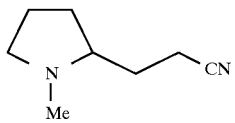

Under stirring, a solution of 2 g of 2-(2-chloroethyl)-1-methylpyrrolidine hydrochloride in 10 ml of dimethyl sulfoxide was added to a solution of 1.06 g of sodium cyanide in 10 ml of dimethylsulfoxide. The resulting solution was heated to 140° C. and stirred for 6 hours. After the addition of a saturated aqueous solution of sodium bicarbonate, the resulting solution was extracted with chloroform. The separated chloroform layer was dried over anhydrous sodium sulfate. The solvent was then evaporated and the resulting residue was subjected to silica gel column chromatography, whereby 1.15 g of 3-(1-methyl-2-pyrrolidine)propionitrile was obtained as the oily form from the fraction eluted with chloroform-methanol-29% aqueous ammonia (100:10:1).

Mass spectrum (m/z): 138 (M$^+$)

Nuclear magnetic resonance spectrum (CDCl$_3$, TMS internal standard) δ: 1.43–1.50 (1H, m), 1.61–1.80 (3H, m), 1.93–2.00 (2H, m), 2.17–2.50 (4H, m), 2.31 (3H, s), 3.06 (1H, t)

The compounds of Reference Examples 6–7 were obtained by the same manner as described in Reference Example 5.

REFERENCE EXAMPLE 6

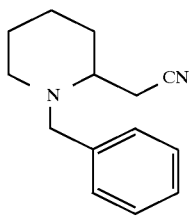

(1-Benzyl-2-piperidine)acetonitrile
Starting compound
1-Benzyl-2-chloromethylpiperidine hydrochloride
Nuclear magnetic resonance spectrum (CDCl$_3$, TMS internal standard) δ: 1.25–2.30 (6H, m), 2.50–3.00 (5H, m), 3.29 (1H, d, J=14 Hz), 3.87 (1H, d, J=14 Hz), 7.15–7.45 (5H, m)

REFERENCE EXAMPLE 7

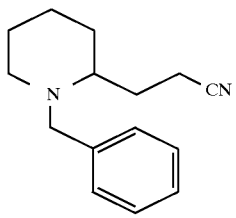

3-(1-Benzyl-2-piperidine)propionitrile
Starting compound
1-Benzyl-2-(2-chloroethyl)piperidine hydrochloride
Infrared absorption spectrum: νmax (KBr) cm$^{-1}$: 3076, 3040, 2948, 2868, 2808, 2252, 1498, 1456, 736, 700
Nuclear magnetic resonance spectrum (CDCl$_3$, TMS internal standard) δ: 1.3–2.9 (13H, m), 2.31 (1H, d, J=14 Hz), 2.89 (1H, d, J=14 Hz), 7.2–7.4 (5H, m)

REFERENCE EXAMPLE 8

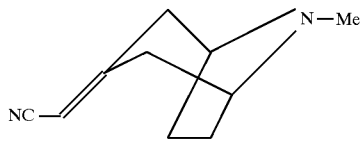

A solution of 1.95 g of diethyl cyanomethylphosphonate in 40 ml of dioxane was cooled to 10° C., followed by the addition of 0.44 g of sodium hydride (60%) in an argon gas atmosphere. A solution of 1.39 g of tropinone in 25 ml of dioxane was added dropwise to the resulting mixture at the same temperature, followed by stirring at room temperature for 1.5 hours. After the solvent was evaporated, water was added to the residue. The resulting mixture was extracted with chloroform, followed by drying over anhydrous potassium carbonate. The solvent was then evaporated, whereby 1.66 g of 3-cyanomethylene-8-methyl-8-azabicyclo[3.2.1]octane was obtained as the oily form.

Mass spectrum (m/z): 162 (M$^+$)
Infrared absorption spectrum: νmax(NaCl)cm$^{-1}$: 2220 (C≡N)
Nuclear magnetic resonance spectrum (CDCl$_3$, TMS internal standard) δ: 2.38 (3H, s), 5.17 (1H, s)

REFERENCE EXAMPLE 9

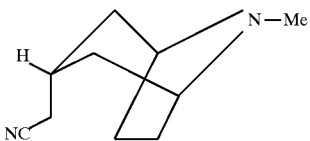

To a solution of 1.42 g of 3-cyanomethylene-8-methyl-8-azabicyclo[3.2.1]octane in 50 ml of methanol, 0.80 g of 10% palladium-carbon was added, followed by stirring at room temperature for 72 hours in a hydrogen gas stream at 1 atm. The palladium-carbon was removed by filtration. The residue obtained by evaporation of the solvent was purified by silica gel column chromatography (eluent: chloroform/methanol/29% aqueous ammonia), whereby 0.70 g of endo-8-methyl-8-azabicyclo[3.2.1]octane-3-acetonitrile was obtained as the oily form.

Mass spectrum (m/z): 164 (M$^+$)
Infrared absorption spectrum: νmax(NaCl)cm$^{-1}$: 2252 (C≡N)
Nuclear magnetic resonance spectrum (CDCl$_3$, TMS internal standard): δ: 1.40 (2H, d), 1.49–1.54 (2H, m), 2.09–2.11 (2H, m), 2.14–2.16 (1H, m), 2.20–2.24 (2H, m), 2.25 (3H, s), 2.46 (2H, m), 3.15 (2H, s)

REFERENCE EXAMPLE 10

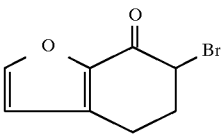

In 100 ml of diethyl ether, 1.09 g of 7-oxo-4,5,6,7-tetrahydrobenzofuran was dissolved, and 0.41 ml of bromine was added. The mixture was stirred at room temperature for one hour. The solvent was then evaporated, and the residue was subjected to silica gel column chromatography, whereby 1.13 g of 6-bromo-7-oxo-4,5,6,7-tetrahydrobenzofuran was obtained as the oil form from the fraction eluted with hexane-ethyl acetate (10:1).

Mass spectrum (m/z): 214, 216 (M$^+$)
Nuclear magnetic resonance spectrum (CDCl$_3$, TMS internal standard) δ: 2.54 (2H, m), 2.78–2.98 (2H, m), 4.62 (1H, t), 6.46 (1H, d), 7.65 (1H, d)

REFERENCE EXAMPLE 11

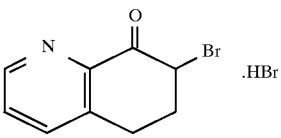

To a solution of 0.68 g of 8-oxo-5,6,7,8-tetrahydroquinoline in 25 ml of acetic acid, 2.5 ml of a 25% solution of hydrobromic acid in acetic acid was added, followed by the dropwise addition of 0.235 ml of bromine. After stirring at room temperature for 30 minutes, the solvent was evaporated. The resulting residue was washed with diethyl ether, whereby 1.5 g of 7-bromo-8-oxo-5,6,7,8-tetrahydroquinoline hydrobromide was obtained.

Mass spectrum (m/z): 225, 227 (M$^+$)

Nuclear magnetic resonance spectrum (DMSO-$d_6$, TMS internal standard) δ: 2.4–2.5 (1H, m), 2.7–2.8 (1H, m), 3.1–3.2 (2H, m), 5.23 (1H, dd)

REFERENCE EXAMPLE 12

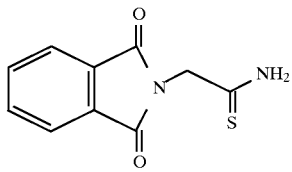

In a 20 ml 4N solution of hydrogen chloride in ethyl acetate, 3.07 g of phthalimidoacetonitrile was dissolved. To the resulting solution, 3.17 ml of O,O-diethyl dithiophosphate was added, followed by stirring at room temperature for 6 hours. The precipitate formed was collected by filtration, and washed successively with ethyl acetate and diethyl ether, whereby 2.29 g of phthalimidothioacetamide was obtained.

Mass spectrum (m/z): 220 ($M^+$)

Nuclear magnetic resonance spectrum (DMSO-$d_6$, TMS internal standard) δ: 4.46 (2H, s), 7.85–7.98 (4H, m), 9.44 (1H, br), 9.76 (1H, br)

The compounds of the following Reference Example 13–39 were obtained by the same manner as described in Reference Example 12.

REFERENCE EXAMPLE 13

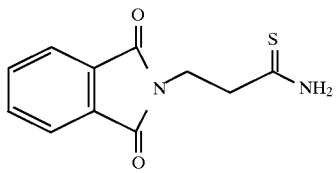

3-Phthalimidopropanethioamide
Starting compound
3-Phthalimidopropionitrile
Mass spectrum (m/z): 234 ($M^+$)
Nuclear magnetic resonance spectrum (DMSO-$d_6$, TMS internal standard) δ: 2.34 (2H, t), 3.92 (2H, t), 7.85 (4H, s), 9.37 (2H, br)

REFERENCE EXAMPLE 14

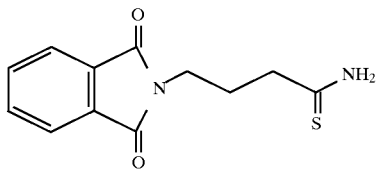

4-Phthalimidobutanethioamide
Starting compound
4-Phthalimidobutylonitrile
Mass spectrum (m/z): 248 ($M^+$)
Nuclear magnetic resonance spectrum (DMSO-$d_6$, TMS internal standard): δ: 1.97–2.06 (2H, m), 2.42–2.55 (2H, m), 3.60 (2H, t), 7.86 (4H, s), 9.20–9.40 (2H, br)

REFERENCE EXAMPLE 15

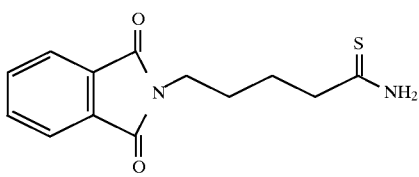

5-Phthalimidopentanethioamide
Starting compound
5-Phthalimidovaleronitrile
Mass spectrum (m/z): 262 ($M^+$)
Nuclear magnetic resonance spectrum (DMSO-$d_6$, TMS internal standard): δ: 1.62 (4H, m), 2.50 (2H, t), 3.58 (2H, t), 7.80–7.90 (4H, m), 9.30 (2H, br)

REFERENCE EXAMPLE 16

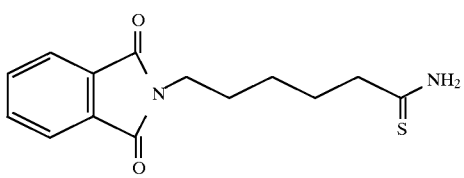

6-Phthalimidohexanethioamide
Starting compound
6-Phthalimidocapronitrile
Mass spectrum (m/z): 276 ($M^+$)
Nuclear magnetic resonance spectrum (DMSO-$d_6$, TMS internal standard) δ: 1.54–1.67 (6H, m), 2.51 (2H, t), 3.57 (2H, t), 7.85 (4H, m), 9.20 (2H, br)

REFERENCE EXAMPLE 17

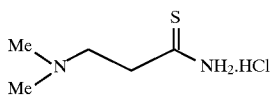

3-Dimethylaminopropanethioamide hydrochloride
Starting compound
3-Dimethylaminopropionitrile
Mass spectrum (m/z): 133 ($M^+$)

REFERENCE EXAMPLE 18

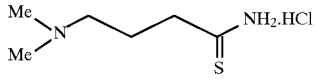

4-Dimethylaminobutanethioamide hydrochloride
Starting compound
4-Dimethylaminobutylonitrile hydrochloride
Mass spectrum (m/z): 147 ($M^++1$)

REFERENCE EXAMPLE 19

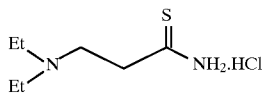

3-Diethylaminopropanethioamide hydrochloride
Starting compound
3-Diethylaminopropionitrile
Mass spectrum (m/z): 161 (M$^+$+1)
Nuclear magnetic resonance spectrum (DMSO-d$_6$, TMS internal standard): δ: 1.25 (6H, t), 3.05–3.48 (8H, m), 9.70 (2H, br)

REFERENCE EXAMPLE 20

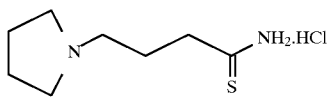

4-(1-Pyrrolidine)butanethioamide hydrochloride
Starting compound
4-(1-Pyrrolidine)butylonitrile
Nuclear magnetic resonance spectrum (DMSO-d$_6$, TMS internal standard): δ: 1.24–1.32 (2H, m), 1.84–1.96 (4H, m), 3.02–3.17 (6H, m), 3.39–3.47 (2H, m)

REFERENCE EXAMPLE 21

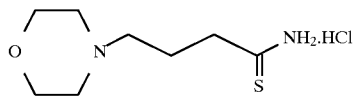

4-Morpholinobutanethioamide hydrochloride
Starting compound
4-Morpholinobutylonitrile
Mass spectrum (m/z): 189 (M$^+$+1)
Nuclear magnetic resonance spectrum (DMSO-d$_6$, TMS internal standard): δ: 1.84–2.00 (2H, m), 2.31–2.52 (6H, m), 3.56–3.76 (6H, m)

REFERENCE EXAMPLE 22

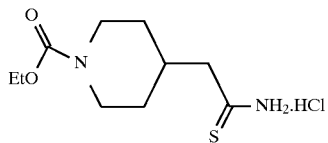

(1-Ethoxycarbonyl-4-piperidine)thioacetamide hydrochloride
Starting compound
(1-Ethoxycarbonyl-4-piperidine)acetonitrile
Melting point: 109°–111° C. diethyl ether
Mass spectrum (m/z): 231 (M$^+$+1)
Nuclear magnetic resonance spectrum (DMSO-d$_6$, TMS internal standard): δ: 1.10–1.21 (2H, m), 1.25 (3H, t), 1.79 (2H, d), 2.13–2.24 (1H, m), 2.53 (2H, d), 2.78 (2H, t), 4.09–4.20 (4H, m)

REFERENCE EXAMPLE 23

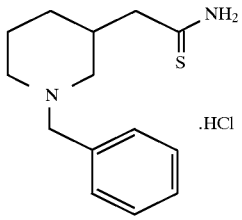

(1-Benzyl-3-piperidine)thioacetamide hydrochloride
Starting compound
(1-Benzyl-3-piperidine)acetonitrile
Mass spectrum (m/z): 249 (M$^+$+1)
Infrared absorption spectrum (KBr) cm$^{-1}$: 1458, 1422, 1218, 1182.

REFERENCE EXAMPLE 24

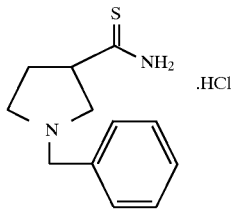

(1-Benzyl-3-pyrrolidine)carbothioamide hydrochloride
Starting compound
(1-Benzyl-3-pyrrolidine)carbonitrile
Melting point: 195°–199° C. ethyl acetate-methanol
Mass spectrum (m/z): 220 (M$^+$)
Nuclear magnetic resonance spectrum (DMSO-d$_6$, TMS internal standard) δ: 2.00–2.20 (1H, m), 2.23–2.42 (1H, m), 3.18–3.27 (1H, m), 3.39–3.72 (4H, m), 4.35–4.45 (2H, m), 7.43–7.44 (3H, m), 7.64–7.66 (2H, m)

REFERENCE EXAMPLE 25

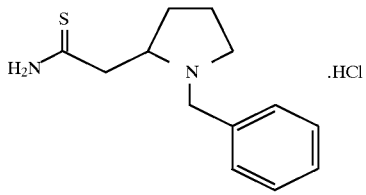

(1-Benzyl-2-pyrrolidine) thioacetamide hydrochloride
Starting compound
(1-Benzyl-2-pyrrolidine)acetonitrile
Mass spectrum (m/z): 235 (M$^+$+1)
Nuclear magnetic resonance spectrum (DMSO-d$_6$, TMS internal standard): δ: 1.6–2.4 (4H, m), 2.9–3.4 (4H, m), 3.9–4.85 (3H, m), 7.35–7.8 (5H, m)

REFERENCE EXAMPLE 26

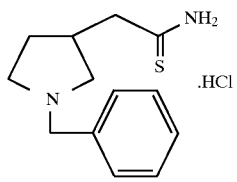

(1-Benzyl-3-pyrrolidine)thioacetamide hydrochloride
Starting compound
(1-Benzyl-3-pyrrolidine)acetonitrile
Mass spectrum (m/z): 234 (M$^+$)
Nuclear magnetic resonance spectrum (DMSO-d$_6$, TMS internal standard) δ: 1.61–1.76 (1H, m), 2.07–2.29 (1H, m), 2.60–3.45 (7H, m), 4.33–4.36 (2H, m), 7.43–7.44 (3H, m), 7.60–7.64 (2H, m)

REFERENCE EXAMPLE 27

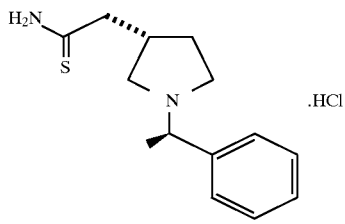

[(S)-1-[(R)-1-Phenylethyl]-3-pyrrolidine]thioacetamide hydrochloride
Starting compound
[(S)-1-[(R)-1-Phenylethyl]-3-pyrrolidine]acetonitrile
Mass spectrum (m/z): 249 (M$^+$+1)

REFERENCE EXAMPLE 28

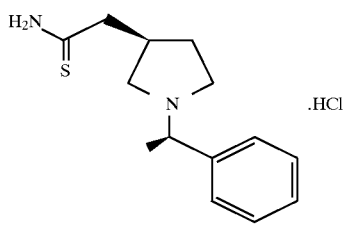

[(R)-1-[(R)-1-Phenylethyl]-3-pyrrolidine]thioacetamide hydrochloride
Starting compound
[(R)-1-[(R)-1-Phenylethyl]-3-pyrrolidine]acetonitrile
Mass spectrum (m/z): 249 (M$^+$+1)

REFERENCE EXAMPLE 29

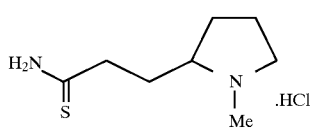

3-(1-Methyl-2-pyrrolidine)propanethioamide hydrochloride
Starting compound
3-(1-Methyl-2-pyrrolidine)propionitrile
Mass spectrum (m/z): 172 (M$^+$)

REFERENCE EXAMPLE 30

Exo-8-methyl-8-azabicyclo[3.2.1]octane-3-carbothioamide hydrochloride
Starting compound
Exo-8-methyl-8-azabicyclo[3.2.1]octane-3-carbonitrile
Melting point: 225°–230° C. (dec.) ethyl acetate-ethanol
Nuclear magnetic resonance spectrum (DMSO-d$_6$, TMS internal standard) δ: 1.62–1.82 (2H, m), 1.87–1.99 (2H, m), 2.09–2.31 (4H, m), 2.59–2.79 (4H, m), 3.85–3.88 (2H, m)

REFERENCE EXAMPLE 31

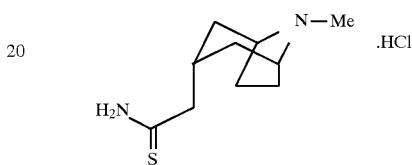

Endo-8-methyl-8-azabicyclo[3.2.1]octane-3-thioacetamide hydrochloride
Starting compound
Endo-8-methyl-8-azabicylco[3.2.1]octane-3-acetonitrile
Melting point: 230°–233° C. ethyl acetate-methanol
Mass spectrum (m/z): 198 (M$^+$)
Nuclear magnetic resonance spectrum (DMSO-d$_6$, TMS internal standard) δ: 1.44–1.66 (2H, m), 1.99–2.04 (2H, m), 2.19–2.21 (2H, m), 2.38–2.43 (2H, m), 2.46–2.48 (1H, m), 2.59–2.61 (3H, m), 2.69–2.75 (2H, m), 3.67–3.76 (2H, m)

REFERENCE EXAMPLE 32

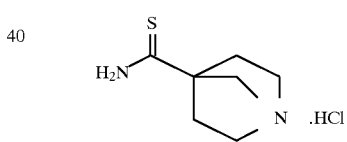

1-Azabicyclo[2.2.1]heptane-4-carbothioamide hydrochloride
Starting compound
1-Azabicyclo[2.2.1]heptane-4-carbonitrile
Mass spectrum (m/z): 157 (M$^+$+1)
Nuclear magnetic resonance spectrum (DMSO-d$_6$, TMS internal standard): δ: 2.14 (4H, m), 3.35 (4H, m), 3.50 (2H, m)

REFERENCE EXAMPLE 33

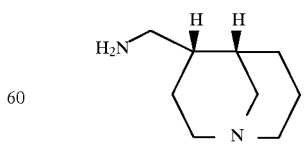

(4R*,5R*)-1-Azabicyclo[3.3.1]nonane-4-carbothioamide
Starting compound
(4R*,5R*)-1-Azabicyclo[3.3.1]nonane-4-carbonitrile
Mass spectrum (m/z): 185 (M$^+$+1)

Nuclear magnetic resonance spectrum (CDCl₃, TMS internal standard): δ: 2.66 (2H, s)

REFERENCE EXAMPLE 34

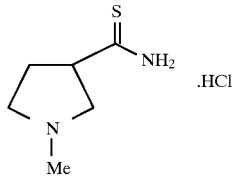

(1-Methyl-3-pyrrolidine)carbothioamide hydrochloride

Starting compound (1-Methyl-3-pyrrolidine)carbonitrile
Melting point: 119°–123° C. ethyl acetate-methanol
Mass spectrum (m/z): 145 (M⁺+1)
Nuclear magnetic resonance spectrum (DMSO-d₆, TMS internal standard): δ: 2.02–2.16 (1H, m), 2.23–2.40 (1H, m), 2.78–2.82 (3H, m), 3.13–3.86 (5H, m)

REFERENCE EXAMPLE 35

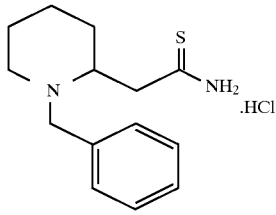

(1-Benzyl-2-piperidine)thioacetamide hydrochloride

Starting compound (1-Benzyl-2-piperidine)acetonitrile
Mass spectrum (m/z): 248 (M⁺)

REFERENCE EXAMPLE 36

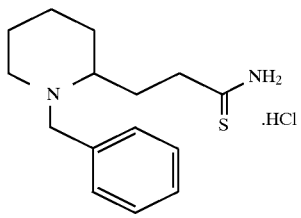

3-(1-Benzyl-2-piperidine)propanethioamide hydrochloride

Starting compound 3-(1-Benzyl-2-piperidine)propionitrile
Mass spectrum (m/z): 263 (M⁺+1)
Infrared absorption spectrum: νmax (KBr) cm⁻¹: 1636, 1458, 1424, 702

REFERENCE EXAMPLE 37

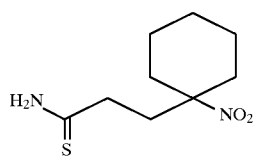

3-(1-Nitrocyclohexyl)propanethioamide
Starting compound 3-(1-Nitrocyclohexyl)propionitrile
Mass spectrum (m/z): 216 (M⁺)
Nuclear magnetic resonance spectrum (CDCl₃, TMS internal standard) δ: 1.20–2.00 (8H, m), 2.20–2.60 (6H, m)

REFERENCE EXAMPLE 38

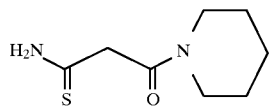

(Piperidinocarbonyl)thioacetamide
Starting compound (Piperidinocarbonyl)acetonitrile
Mass spectrum (m/z): 186 (M⁺)
Nuclear magnetic resonance spectrum (CDCl₃, TMS internal standard) δ: 4.14 (2H, s)

REFERENCE EXAMPLE 39

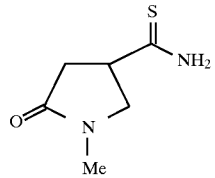

1-Methyl-2-pyrrolidinone-4-carbothioamide
Starting compound

1-Methyl-2-pyrrolidinone-4-carbonitrile
Melting point: 127°–133° C. ethyl acetate-methanol
Mass spectrum (m/z): 158 (M⁺)

REFERENCE EXAMPLE 40

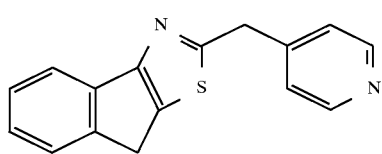

In 100 ml of isopropanol, 1.95 g of 4-pyridinethioacetamide hydrochloride and 1.8 g of 2-bromo-1-indanone was dissolved. Then, 2 g of calcium carbonate was added, followed by heating under reflux for 5 hours. After cooling, the insoluble matter was removed by filtration, and the solvent was evaporated. Ethyl acetate and 1N hydrochloric acid were added to the resulting residue. The aqueous layer was separated and neutralized with sodium bicarbonate, followed by extraction with chloroform. The chloroform layer separated was dried over anhydrous sodium sulfate. The residue obtained by evaporation of the solvent was subjected to silica gel column chromatography, whereby 1.54 g of 2-(4-pyridylmethyl)-8H-indeno[1,2-d]thiazole was obtained as the oil form from the fraction eluted with chloroform-methanol-29% aqueous ammonia (100:10:1).

Mass spectrum (m/z): 264 (M+)

Nuclear magnetic resonance spectrum (CDCl3, TMS internal standard): δ: 3.80 (2H, s), 4.43 (2H, s), 7.26–7.84 (6H, m), 8.53–8.68 (2H, m)

Compounds of Reference Examples 41–43 were obtained by the same manner as described in Reference Example 40.

REFERENCE EXAMPLE 41

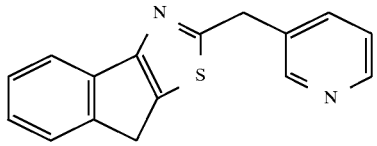

2-(3-Pyridylmethyl)-8H-indeno[1,2-d]thiazole
Starting compound
  2-bromo-1-indanone, 3-pyridinethioacetamide hydrochloride
  Melting point: 112°–113° C. ethyl acetate
  Mass spectrum (m/z): 264 (M+)
  Nuclear magnetic resonance spectrum (CDCl3, TMS internal standard): δ: 3.79 (2H, s), 4.43 (2H, s), 7.25–7.28 (2H, m), 7.39 (1H, d), 7.48 (1H, d), 7.69 (1H, d), 7.74 (1H, d), 8.54 (1H, dd), 8.65 (1H, d)

REFERENCE EXAMPLE 42

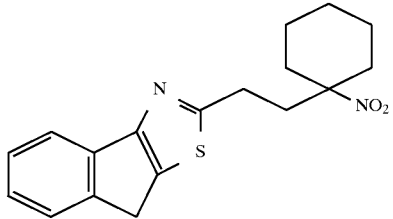

2-[2-(1-Nitrocyclohexyl)ethyl]-8H-indeno[1,2-d]thiazole
Starting compound
  2-Bromo-1-indanone, 3-(1-nitrocyclohexyl)propanethioamide
  Mass spectrum (m/z): 329 (M++1)
  Nuclear magnetic resonance spectrum (CDCl3, TMS internal standard): δ: 1.20–2.00 (8H, m), 2.30–2.70 (4H, m), 2.90–3.30 (2H, m), 3.79 (2H, s), 7.20–7.80 (4H, m)

REFERENCE EXAMPLE 43

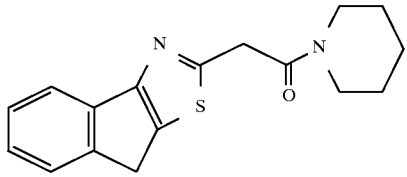

2-[(Piperidinocarbonyl)methyl]-8H-indeno[1,2-d]thiazole
Starting compound
  2-Bromo-1-indanone, (piperidinocarbonyl)thioacetamide Melting point: 127°–129° C. ethyl acetate-hexane
Mass spectrum (m/z): 298 (M+)
Nuclear magnetic resonance spectrum (CDCl3, TMS internal standard) δ: 1.50–1.70 (6H, m), 3.57 (2H, t, J=5.5 Hz), 3.61 (2H, t, J=5.5 Hz), 3.83 (2H, s), 4.25 (2H, s), 7.25 (1H, t, J=7.0 Hz), 7.37 (1H, t, J=7.0 Hz), 7.49 (1H, d, J=7.0 Hz), 7.76 (1H, d, J=7.0 Hz)

REFERENCE EXAMPLE 44

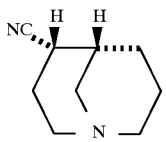

To a solution of 2.00 g of 1-azabicyclo[3.3.1]nonan-4-one in 100 ml of dimethoxyethane, 3.65 g of p-toluenesulfonylmethylisocyanide and 1.13 g of ethanol were added, followed by cooling to 5° C. Then, 4.00 g of potassium tert-butoxide was added while keeping the internal temperature below 10° C. The mixture was stirred at room temperature for 30 minutes, followed by further stirring at 40° C. for 30 minutes. The precipitate thus formed was removed by filtration. The residue obtained by evaporation of the solvent was purified by an alumina column chromatography (eluent: chloroform:hexane=1:1). The resulting crude product was then purified by silica gel column chromatography (eluent: chloroform:methanol= 20:1), whereby 1.01 g of (4R*,5R*)-1-azabicyclo[3.3.1]nonane-4-carbonitrile was obtained.

Mass spectrum (m/z): 150 (M+)

Nuclear magnetic resonance spectrum (CDCl3, TMS internal standard) δ: 1.4–1.6 (1H, m), 1.7–2.0 (4H, m), 2.1–2.4 (2H, m), 2.85 (1H, d, J=14 Hz), 3.0–3.2 (6H, m)

REFERENCE EXAMPLE 45

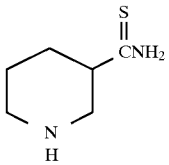

In 30 ml of a saturated ammonia-methanol solution, 6.4 g (58 mmol) of 3-piperidinecarbonitrile was dissolved, followed by introduction of hydrogen sulfide gas until saturation while maintaining the temperature at 10°–15° C. While keeping the sealed condition, the resulting solution was stirred at room temperature for 2 days. The reaction mixture was evaporated to dryness under reduced pressure. The residue was recrystallized from methanol-isopropanol, and then from water, whereby 0.5 g of (3-piperidine)carbothioamide was obtained in the form of crystals.

Melting point: 223°–226° C. water

Mass spectrum (m/z): 144 (M+)

REFERENCE EXAMPLE 46

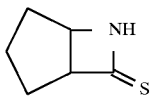

In 60 ml of tetrahydrofuran, 2.8 g of 6-azabicyclo[3.2.0] heptan-7-one was dissolved. Then, 10.2 g of the Lawesson's Reagent was added, followed by heating under reflux for 3 hours. The solvent was then evaporated and the resulting residue was subjected to silica gel column chromatography, whereby 0.78 g of 6-azabicyclo[3.2.0]heptane-7-thione was obtained as the crystal form from the fraction eluted with hexane-ethyl acetate (4:1).

Melting point: 67°–70° C. hexane-ethyl acetate

Mass spectrum (m/z): 127 (M$^+$)

Nuclear magnetic resonance spectrum (CDCl$_3$, TMS internal standard): δ: 1.37–1.54 (2H, m), 1.74–1.94 (3H, m), 2.06 (1H, dd), 3.48 (1H, d), 4.55 (1H, t), 7.80 (1H, br)

The compound of Reference Example 47 was obtained by the same manner as described in Reference Example 46.

REFERENCE EXAMPLE 47

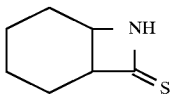

7-Azabicyclo[4.2.0]octane-8-thione
Starting compound
7-Azabicyclo[4.2.0]octan-8-one
Mass spectrum (m/z): 141 (M$^+$)
Nuclear magnetic resonance spectrum (CDCl$_3$, TMS internal standard): δ: 1.43–2.04 (8H, m), 3.16–3.20 (1H, m), 3.37 (1H, dd)

REFERENCE EXAMPLE 48

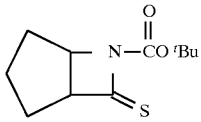

In 50 ml of methylene chloride, 0.82 g of 6-azabicyclo [3.2.0]heptane-7-thione was dissolved. Then, 0.90 ml of triethylamine, 0.79 g of dimethylaminopyridine, and 2.81 g of di-tert-butyldicarbonate were added successively, followed by stirring at room temperature for 10 minutes. The solvent was evaporated and the resulting residue was subjected to silica gel column chromatography, whereby 1.48 g of 6-tert-butoxycarbonyl-6-azabicyclo[3.2.0]heptane-7-thione was obtained as the crystal form from the fraction eluted with hexane-ethyl acetate (2:1).

Melting point: 86°–88° C. hexane-ethyl acetate

Mass spectrum (m/z): 227 (M$^+$)

Nuclear magnetic resonance spectrum (CDCl$_3$, TMS internal standard): δ: 1.41–1.58 (2H, m), 1.54 (9H, s), 1.64–1.72 (1H, m), 1.84–1.90 (1H, m), 2.08 (1H, dd), 2.22 (1H, dd), 3.31 (1H, dd), 4.78 (1H, t)

The compound of Reference Example 49 was obtained by the same manner as described in Reference Example 48.

REFERENCE EXAMPLE 49

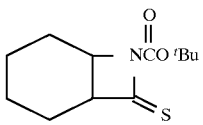

7-tert-Butoxycarbonyl-7-azabicyclo[4.2.0]octane-8-thione
Starting compound
7-Azabicyclo[4.2.0]octane-8-thione
Mass spectrum (m/z): 241 (M$^+$)
Nuclear magnetic resonance spectrum (CDCl$_3$, TMS internal standard): δ: 1.26–2.10 (8H, m), 1.55(9H, s), 3.03–3.07 (1H, m), 4.60 (1H, dd)

REFERENCE EXAMPLE 50

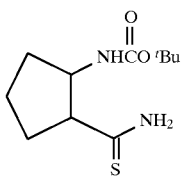

In 42 ml of 29% aqueous ammonia and 60 ml of methanol, 1.48 g of 6-tert-butoxycarbonyl-6-azabicyclo [3.2.0]heptane-7-thione was dissolved, followed by stirring at room temperature for 30 minutes. The solvent was azeotropically evaporated using benzene-ethanol, whereby 1.39 g of 2-(tert-butoxycarbonylamino) cyclopentanecarbothioamide was obtained as the crystal form.

Melting point: 162°–164° C. ethanol

Mass spectrum (m/z): 245 (M$^+$+1)

Nuclear magnetic resonance spectrum (CDCl$_3$, TMS internal standard): δ: 1.44 (9H, s), 1.47–2.39 (6H, m), 2.38 (1H, br), 3.27–3.33 (1H, m), 4.11–4.19 (1H, m)

The compound of Reference Example 51 was obtained by the same manner as described in Reference Example 50.

REFERENCE EXAMPLE 51

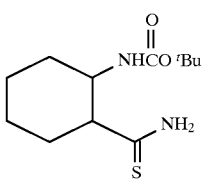

2-(tert-Butoxycarbonylamino) cyclohexanecarbothioamide
Starting compound
7-tert-Butoxycarbonyl-7-azabicyclo[4.2.0]octane-8-thione
Melting point: 178°–180° C. hexane-ethyl acetate
Mass spectrum (m/z): 258 (M$^+$)
Nuclear magnetic resonance spectrum (CDCl$_3$, TMS internal standard): δ: 1.23–2.14 (8H, m), 1.43 (9H, s), 2.77 (1H, br), 4.23 (1H, br)

Example 1

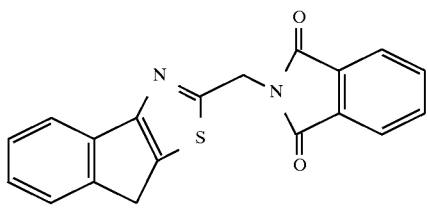

In 100 ml of isopropanol, 1.64 g of 2-bromo-1-indanone was dissolved. Then, 2.0 g of phthalimidothioacetamide was added, followed by heating under reflux for 6 hours. The precipitate thus formed was collected by filtration and then distributed between chloroform and a saturated aqueous solution of sodium bicarbonate. The organic layer was separated, washed successively with water and a saturated aqueous solution of sodium chloride, and then dried over anhydrous sodium sulfate. The solvent was then evaporated, whereby 1.3 g of 2-phthalimidomethyl-8H-indeno[1,2-d]thiazole was obtained.

Mass spectrum (m/z): 332 (M+)

Nuclear magnetic resonance spectrum (CDCl$_3$, TMS internal standard): δ: 3.79 (2H, s), 5.29 (2H, s), 7.20–7.51 (4H, m), 7.70–7.98 (4H, m)

The following compounds of Examples 2–7 were obtained by the same manner as described in Example 1.

Example 2

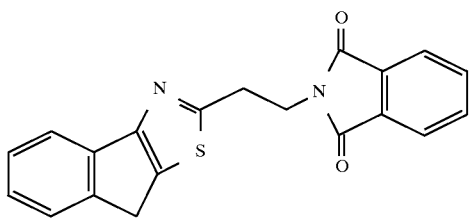

2-(2-Phthalimidoethyl)-8H-indeno[1,2-d]thiazole
Starting compound
2-Bromo-1-indanone, 3-phthalimidopropanethioamide
Mass spectrum (m/z): 346 (M+)
Nuclear magnetic resonance spectrum (CDCl$_3$, TMS internal standard): δ: 3.49 (2H, t), 3.78 (2H, s), 4.18 (2H, t), 7.19–7.90 (8H, m)

Example 3

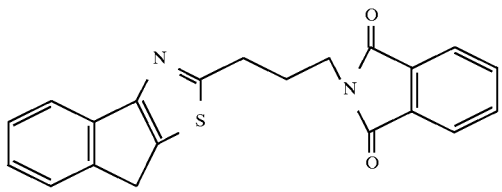

2-(3-Phthalimidopropyl)-8H-indeno[1,2-d]thiazole
Starting compound
2-Bromo-1-indanone, 4-phthalimidobutanethioamide
Mass spectrum (m/z): 360 (M+)
Nuclear magnetic resonance spectrum (CDCl$_3$, TMS internal standard): δ: 2.21–2.45 (2H, m), 3.19 (2H, t), 3.78 (2H, s), 3.87 (2H, t), 7.19–7.51 (4H, m), 7.60–7.87 (4H, m)

Example 4

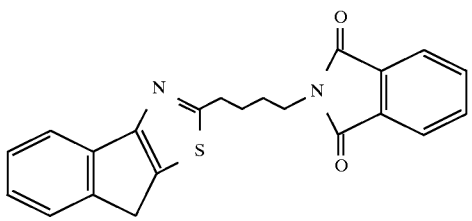

2-(4-Phthalimidobutyl)-8H-indeno[1,2-d]thiazole
Starting compound
2-Bromo-1-indanone, 5-phthalimidopentanethioamide
Mass spectrum (m/z): 374 (M+)
Nuclear magnetic resonance spectrum (CDCl$_3$, TMS internal standard): δ; 1.74–1.83 (4H, m), 3.05–3.28 (2H, m), 3.70–3.77 (2H, m), 3.78 (2H, s), 7.69–7.80 (8H, m)

Example 5

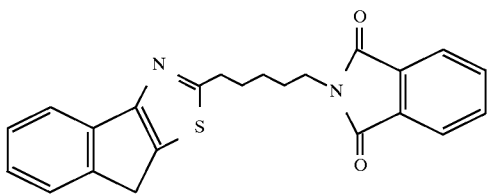

2-(5-Phthalimidopentyl)-8H-indeno[1,2-d]thiazole
Starting compound
2-Bromo-1-indanone, 6-phthalimidohexanethioamide
Mass spectrum (m/z): 388 (M+)
Nuclear magnetic resonance spectrum (CDCl$_3$, TMS internal standard): δ: 1.41–1.95 (6H, m), 3.02 (2H, t), 3.70 (2H, t), 3.77 (2H, s), 7.64–7.90 (8H, m)

Example 6

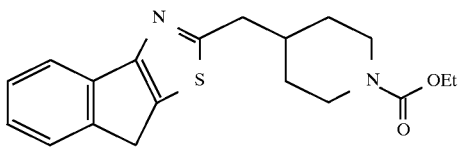

2-[(1-Ethoxycarbonyl-4-piperidyl)methyl]-8H-indeno[1,2-d]thiazole
Starting compound
2-Bromo-1-indanone, (1-ethoxycarbonyl-4-piperidine)thioacetamide
Mass spectrum (m/z): 342 (M+)
Nuclear magnetic resonance spectrum (DMSO-d$_6$, TMS internal standard): δ: 1.11–1.21 (5H, m), 1.69 (2H, d), 1.94–2.01 (1H, m), 3.01 (2H, d), 3.09 (2H, s), 3.94–4.04 (4H, m), 7.25 (1H, t), 7.36 (1H, t), 7.56 (1H, d), 7.63 (1H, d)

Example 7

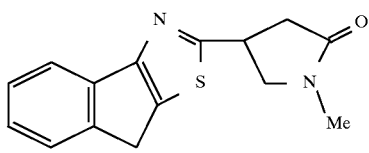

2-(1-Methyl-2-oxo-4-pyrrolidinyl)-8H-indeno[1,2-d]thiazole

Starting compound

2-Bromo-1-indanone, 1-methyl-2-pyrrolidinone-4-carbothioamide

Melting point: 114°–116° C.

Mass spectrum (m/z): 270 (M⁺)

Nuclear magnetic resonance spectrum (DMSO-$d_6$, TMS internal standard): δ: 2.64 (1H, dd), 2.79 (3H, s), 2.85 (1H, dd), 3.88 (1H, dd), 3.94 (2H, s), 4.09–4.15 (1H, m), 7.28 (1H, t), 7.38 (1H, t), 7.59 (1H, d), 7.66 (1H, d)

Example 8

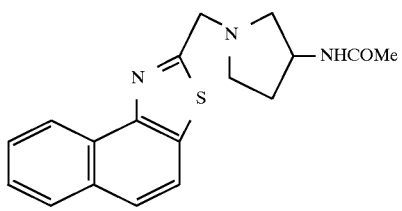

To a solution of 0.14 g of 2-bromomethylnaphtho[1,2-d]thiazole and 0.10 g of 3-acetamidopyrrolidine in 7 ml of ethanol was added 0.14 g of potassium carbonate, followed by heating under reflux for 1 hour. The solvent was then evaporated, water was added to the resulting residue, followed by extraction with chloroform. The extract was dried over anhydrous magnesium sulfate. The solvent was evaporated, and ether was added to the resulting residue to cause crystallization, whereby 0.13 g of 2-[(3-acetamide-1-pyrrolidinyl)methyl]naphtho[1,2-d]thiazole was obtained.

Mass spectrum (m/z): 326 (M⁺+1)

Example 9

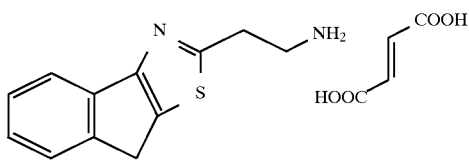

In 20 ml of methanol, 1.79 g of 2-(2-phthalimidoethyl)-8H-indeno[1,2-d]thiazole was dissolved. Then, 40 ml of a 40% solution of methylamine in methanol was added, followed by stirring at room temperature for 14 hours. The solvent was then evaporated, and chloroform and 1N hydrochloric acid were added to the resulting residue. The aqueous layer was separated and then neutralized with a 1N aqueous solution of sodium hydroxide, followed by extraction with chloroform. The chloroform layer separated was washed successively with water and a saturated aqueous solution of sodium chloride, followed by drying over anhydrous sodium sulfate. The residue obtained by evaporation of the solvent was dissolved in methanol, and fumaric acid was added thereto. The crystals formed were collected by filtration and then washed successively with methanol and diethyl ether, followed by recrystallization from methanol, whereby 572 mg of 2-(2-aminoethyl)-8H-indeno[1,2-d]thiazole fumarate was obtained.

Melting point: 208°–210° C. methanol

| Elemental Analysis for $C_{12}H_{12}N_2S.C_4H_4O_4$ | | | | |
|---|---|---|---|---|
| | C(%) | H(%) | N(%) | S(%) |
| Calcd.: | 57.82 | 4.85 | 8.48 | 9.65 |
| Found: | 57.48 | 4.91 | 8.38 | 9.62 |

Mass spectrum (m/z): 216 (M⁺)

Nuclear magnetic resonance spectrum (DMSO-$d_6$, TMS internal standard): δ: 3.23 (2H, t), 3.36 (2H, t), 3.92 (2H, s), 6.45 (2H, s), 7.27 (1H, t), 7.37 (1H, t), 7.57 (1H, d), 7.66 (1H, d)

The compounds of the following Examples 10–13 were obtained by the same manner as described in Example 9.

Example 10

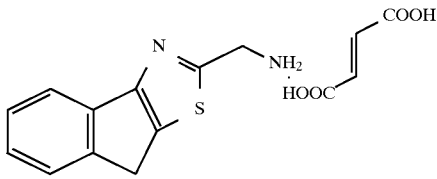

2-Aminomethyl-8H-indeno[1,2-d]thiazole fumarate

Starting compound

2-Phthalimidomethyl-8H-indeno[1,2-d]thiazole

Melting point: 184°–186° C. methanol

| Elemental analysis for $C_{11}H_{10}N_2S.C_4H_4O_4.0.1H_2O$ | | | | |
|---|---|---|---|---|
| | C(%) | H(%) | N(%) | S(%) |
| Calcd.: | 56.27 | 4.47 | 8.75 | 10.02 |
| Found: | 56.12 | 4.45 | 8.62 | 10.12 |

Mass spectrum (m/z): 202 (M⁺)

Nuclear magnetic resonance spectrum (DMSO-$d_6$, TMS internal standard): δ: 3.93 (2H, s), 4.28 (2H, s), 6.55 (2H, s), 7.26 (1H, t), 7.37 (1H, t), 7.57 (1H, d), 7.63 (1H, d)

Example 11

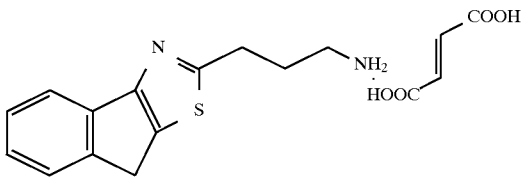

2-(3-Aminopropyl)-8H-indeno[1,2-d]thiazole fumarate

Starting compound 2-(3-Phthalimidopropyl)-8H-indeno[1,2-d]thiazole

Melting point: 178°–180° C. methanol

| Elemental analysis for C₁₃H₁₄N₂S.C₄H₄O₄ | | | | |
|---|---|---|---|---|
| | C(%) | H(%) | N(%) | S(%) |
| Calcd.: | 58.94 | 5.24 | 8.09 | 9.26 |
| Found: | 58.73 | 5.17 | 8.05 | 9.20 |

Mass spectrum (m/z): 230 (M⁺)

Nuclear magnetic resonance spectrum (DMSO-d₆, TMS internal standard): δ: 2.03–2.11 (2H, m), 2.90 (2H, t), 3.17 (2H, t), 3.91 (2H, s), 6.42 (2H, s), 7.26 (1H, t), 7.37 (1H, t), 7.56 (1H, d), 7.63 (1H, d)

Example 12

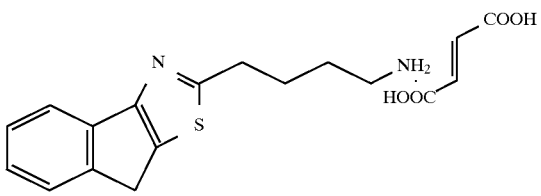

2-(4-Aminobutyl)-8H-indeno[1,2-d]thiazole fumarate
Starting compound
2-(4-Phthalimidobutyl)-8H-indeno[1,2-d]thiazole
Melting point: 183°–186° C. methanol

| Elemental analysis for C₁₄H₁₆N₂S.C₄H₄O₄ | | | | |
|---|---|---|---|---|
| | C(%) | H(%) | N(%) | S(%) |
| Calcd.: | 59.68 | 5.62 | 7.73 | 8.85 |
| Found: | 59.50 | 5.73 | 7.62 | 8.87 |

Mass spectrum (m/z): 244 (M⁺)

Nuclear magnetic resonance spectrum (DMSO-d₆, TMS internal standard): δ: 1.62–1.70 (2H, m), 1.80–1.87 (2H, m), 2.82 (2H, t), 3.10 (2H, t), 3.90 (2H, s), 6.41 (2H, s), 7.25 (1H, t), 7.36 (1H, t), 7.56 (1H, d), 7.62 (1H, d)

Example 13

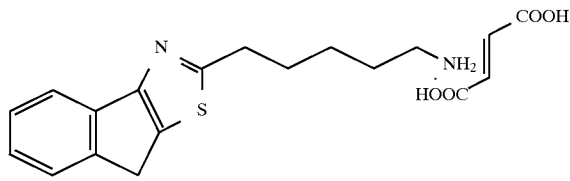

2-(5-Aminopentyl)-8H-indeno[1,2-d]thiazole fumarate
Starting compound
2-(5-Phthalimidopentyl)-8H-indeno[1,2-d]thiazole
Melting point: 184°–186° C. methanol

| Elemental analysis for C₁₅H₁₈N₂S.C₄H₄O₄ | | | | |
|---|---|---|---|---|
| | C(%) | H(%) | N(%) | S(%) |
| Calcd.: | 60.65 | 5.95 | 7.45 | 8.52 |
| Found: | 60.44 | 5.81 | 7.33 | 8.54 |

Mass spectrum (m/z): 258 (M⁺)

Nuclear magnetic resonance spectrum (DMSO-d₆, TMS internal standard): δ: 1.43–1.44 (2H, m), 1.58–1.62 (2H, m), 1.58–1.82 (2H, m), 2.78 (2H, t), 3.07 (2H, t), 3.90 (2H, s), 6.44 (2H, s), 7.25 (1H, t), 7.36 (1H, t), 7.56 (1H, d), 7.62 (1H, d)

Example 14

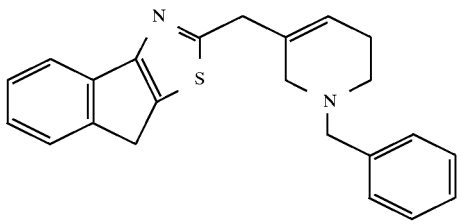

In 5 ml of xylene, 300 mg of 2-(3-pyridylmethyl)-8H-indeno[1,2-d]thiazole was dissolved. Then, 148 μl of benzyl bromide was added, followed by heating under reflux for 3 days. The solvent was evaporated and the resulting residue was dissolved in 4 ml of methanol and 1 ml of water. Then, 60 mg of sodium borohydride was added, followed by stirring at room temperature for 30 minutes. To the residue obtained by evaporation of the solvent, ethyl acetate and 1N hydrochloric acid were added. The aqueous layer was separated and neutralized with sodium bicarbonate, followed by extraction with chloroform. The chloroform layer separated was dried over anhydrous sodium sulfate. The residue obtained by evaporation of the solvent was subjected to silica gel column chromatography, whereby 107 mg of 2-[(1-benzyl- 1,2,3,6-tetrahydro-5-pyridyl)methyl]-8H-indeno[1,2-d]thiazole was obtained as the oil form from the fraction eluted with hexane-ethyl acetate (3:1).

Mass spectrum (m/z): 358 (M⁺)

Nuclear magnetic resonance spectrum (CDCl₃, TMS internal standard) δ: 2.23 (2H, br), 2.54 (2H, t), 3.01–3.03 (2H, m), 3.58 (2H, s), 3.74 (2H, s), 3.80 (2H, s), 5.71 (1H, m), 7.21–7.80 (9H, m)

The following compound of Example 15 was obtained by the same manner as described in Example 14.

Example 15

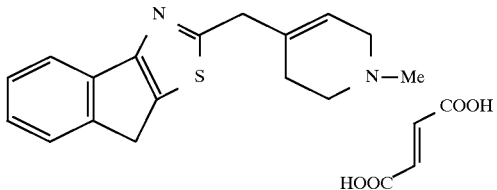

2-[(1-Methyl-1,2,3,6-tetrahydro-4-pyridyl)methyl]-8H-indeno[1,2-d]thiazole fumarate Starting compound 2-(4-Pyridylmethyl)-8H-indeno[1,2-d]thiazole, methyl iodide
Melting point: 162°–164° C. methanol-diethyl ether

| Elemental analysis for C₁₇H₁₈N₂S.C₄H₄O₄.0.4H₂O | | | | |
|---|---|---|---|---|
| | C(%) | H(%) | N(%) | S(%) |
| Calcd.: | 62.17 | 5.66 | 6.91 | 7.90 |
| Found: | 62.09 | 5.61 | 6.90 | 8.20 |

Mass spectrum (m/z): 283 (M⁺+1) Nuclear magnetic resonance spectrum (DMSO-d₆, TMS internal standard): δ: 2.20 (2H, br), 2.42 (3H, s), 2.73 (2H, t), 3.16 (2H, br), 3.80 (2H, s), 3.91 (2H, s), 5.64 (1H, s), 6.57 (1H, s), 7.25 (1H, t), 7.36 (1H, t), 7.56 (1H, d), 7.63 (1H, d)

Example 16

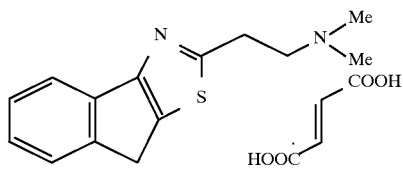

In 10 ml of isopropanol, 630 mg of 2-bromo-1-indanone was dissolved. Then, 555 mg of 3-dimethylaminopropanethioamide hydrochloride was added, followed by heating under reflux for 4 hours. The precipitate formed was collected by filtration and distributed between chloroform and a saturated aqueous solution of sodium bicarbonate. The organic layer was separated, washed successively with water and a saturated aqueous solution of sodium chloride, and then dried over anhydrous sodium sulfate. The solvent was evaporated. The resulting residue was dissolved in methanol, and fumaric acid was added thereto. The crystals formed were collected by filtration, washed successively with methanol and diethyl ether and recrystallized from methanol, whereby 226 mg of 2-(2-dimethylaminoethyl)-8H-indeno[1,2-d]thiazole fumarate was obtained.

Melting point: 142°–144° C. methanol

Mass spectrum (m/z): 245 (M⁺+1)

Nuclear magnetic resonance spectrum (DMSO-d₆, TMS internal standard): δ: 2.35 (6H, s), 2.86 (2H, t), 3.23 (2H, t), 3.90 (2H, s), 6.59 (2H, s), 7.25 (1H, t), 7.36 (1H, t), 7.55 (1H, d), 7.62 (1H, d)

The compounds of the following Examples 17–45 were obtained by the same manner as described in Example 16.

Example 17

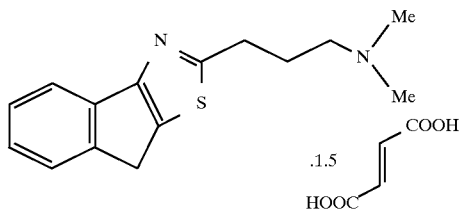

2-(3-Dimethylaminopropyl)-8H-indeno[1,2-d]thiazole sesquifumarate

Starting compound

2-Bromo-1-indanone, 4-dimethylaminobutanethioamide hydrochloride

Melting point: 123°–125° C. methanol

| Elemental analysis for C₁₅H₁₈N₂S.1.5C₄H₄O₄ | | | | |
|---|---|---|---|---|
| | C(%) | H(%) | N(%) | S(%) |
| Calcd.: | 57.84 | 5.64 | 6.42 | 7.35 |
| Found: | 57.71 | 5.55 | 6.41 | 7.59 |

Mass spectrum (m/z): 258 (M⁺)

Nuclear magnetic resonance spectrum (DMSO-d₆, TMS internal standard): δ: 2.10 (2H, m), 2.59 (6H, s), 2.91 (2H, t), 3.13 (2H, t), 3.91 (2H, s), 6.56 (2H, s), 7.14 (1H, t), 7.28 (1H, t), 7.34 (1H, d), 7.46 (1H, d)

Example 18

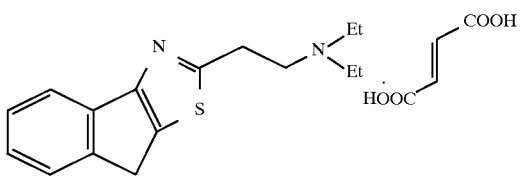

2-(2-Diethylaminoethyl)-8H-indeno[1,2-d]thiazole fumarate

Starting compound

2-Bromo-1-indanone, 3-diethylaminopropanethioamide hydrochloride

Melting point: 115°–117° C. methanol

| Elemental analysis for C₁₆H₂₀N₂S.C₄H₄O₄ | | | | |
|---|---|---|---|---|
| | C(%) | H(%) | N(%) | S(%) |
| Calcd.: | 61.83 | 6.23 | 7.21 | 8.25 |
| Found: | 61.57 | 6.22 | 7.14 | 8.35 |

Mass spectrum (m/z): 272 (M⁺)

Nuclear magnetic resonance spectrum (DMSO-d₆, TMS internal standard): δ: 1.08 (6H, t), 2.81 (4H, q), 3.12 (2H, t), 3.33 (2H, t), 3.90 (2H, s), 6.57 (2H, s), 7.26 (1H, t), 7.37 (1H, t), 7.55 (1H, d), 7.63 (1H, d)

Example 19

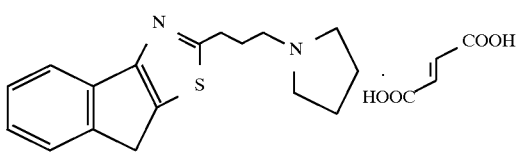

2-[3-(1-Pyrrolidinyl)propyl]-8H-indeno[1,2-d]thiazole fumarate

Starting compound

2-Bromo-1-indanone, 4-(1-pyrrolidine)butanethioamide hydrochloride

Melting point: 165°–167° C. methanol

Elemental analysis for $C_{17}H_{20}N_2S.C_4H_4O_4$

|  | C(%) | H(%) | N(%) | S(%) |
|---|---|---|---|---|
| Calcd.: | 62.98 | 6.04 | 6.99 | 8.01 |
| Found: | 62.88 | 6.08 | 7.04 | 8.16 |

Mass spectrum (m/z): 284 (M⁺)

Nuclear magnetic resonance spectrum (DMSO-$d_6$, TMS internal standard): δ: 1.81–1.84 (6H, m), 2.90–2.95 (8H, m), 3.13 (2H, t), 3.90 (2H, s), 6.51 (2H, s), 7.26 (1H, t), 7.37 (1H, t), 7.56 (1H, d), 7.63 (1H, d)

Example 20

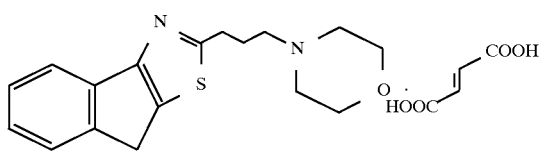

2-(3-Morpholinopropyl)-8H-indeno[1,2-d]thiazole fumarate

Starting compound

2-Bromo-1-indanone, 4-morpholinobutanethioamide hydrochloride

Melting point: 163°–166° C. methanol

Elemental analysis for $C_{17}H_{20}N_2OS.C_4H_4O_4$

|  | C(%) | H(%) | N(%) | S(%) |
|---|---|---|---|---|
| Calcd.: | 58.53 | 5.99 | 6.50 | 7.44 |
| Found: | 58.66 | 5.53 | 6.04 | 7.38 |

Mass spectrum (m/z): 300 (M⁺)

Nuclear magnetic resonance spectrum (DMSO-$d_6$, TMS internal standard): δ: 1.92–1.99 (2H, m), 2.42–2.49 (6H, m), 3.10 (2H, t), 3.59 (4H, t), 3.90 (2H, s), 6.62 (2H, s), 7.25 (1H, t), 7.36 (1H, t), 7.56 (1H, d), 7.62 (1H, d)

Example 21

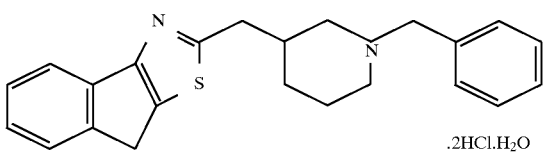

.2HCl.H₂O

2-[(1-Benzyl-3-piperidyl)methyl]-8H-indeno[1,2-d]thiazole dihydrochloride monohydrate Starting compound 2-Bromo-1-indanone, (1-benzyl-3-piperidine)thioacetamide hydrochloride Melting point: 139° C. (dec.) ethyl acetate Elemental analysis for $C_{23}H_{24}N_2S.2HCl.H_2O$

|  | C(%) | H(%) | N(%) | S(%) | Cl(%) |
|---|---|---|---|---|---|
| Calcd.: | 61.19 | 6.25 | 6.21 | 7.10 | 15.71 |
| Found: | 61.19 | 5.96 | 6.19 | 7.10 | 16.03 |

Mass spectrum (m/z): 361 (M⁺+1)

Nuclear magnetic resonance spectrum (DMSO-$d_6$, TMS internal standard): δ: 1.18–1.25 (1H, m), 1.78–1.96 (3H, m), 2.50–2.60 (1H, m), 2.72–2.82 (2H, m), 3.00–3.08 (2H, m), 3.27 (1H, d), 3.42 (1H, d), 3.90 (2H, s), 4.26 (2H, d), 7.25–7.29 (1H, m), 7.37–7.44 (4H, m), 7.56–7.66 (4H, m), 7.77 (1H, br), 11.27 (1H, br)

Example 22

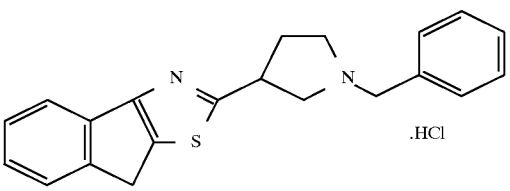

2-(1-Benzyl-3-pyrrolidinyl)-8H-indeno[1,2-d]thiazole hydrochloride

Starting compound (1-Benzyl-3-pyrrolidine)carbothioamide hydrochloride, 2-bromo-1-indanone Melting point: 179°–180° C. methanol Elemental analysis for $C_{21}H_{20}N_2S.HCl.0.45H_2O$

|  | C(%) | H(%) | N(%) | S(%) | Cl(%) |
|---|---|---|---|---|---|
| Calcd.: | 66.90 | 5.85 | 7.43 | 8.50 | 9.40 |
| Found: | 66.61 | 5.88 | 7.41 | 8.62 | 9.69 |

Mass spectrum (m/z): 322 (M⁺)

Nuclear magnetic resonance spectrum (DMSO-$d_6$, TMS internal standard): δ: 2.21–2.43 (1H, m), 2.51–2.67 (1H, m), 3.28–3.32 (1H, m), 3.47–3.54 (2H, m), 3.67–3.85 (1H, m), 3.94 (2H, d), 4.01–4.33 (1H, m), 4.49 (2H, dd), 7.25–7.30 (1H, m), 7.35–7.41 (1H, m), 7.46–7.48 (3H, m), 7.56–7.69 (4H, m)

Example 23

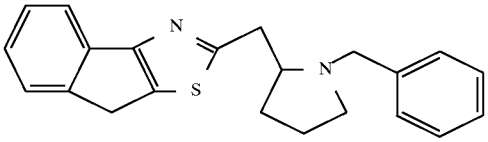

2-[(1-Benzyl-2-pyrrolidinyl)methyl]-8H-indeno[1,2-d]thiazole

Starting compound (1-Benzyl-2-pyrrolidine)thioacetamide hydrochloride, 2-bromo-1-indanone Mass spectrum (m/z): 347 (M⁺+1)

Nuclear magnetic resonance spectrum (CDCl₃, TMS internal standard): δ: 1.50–2.40 (5H, m), 2.80–3.12 (2H, m), 3.18–3.60 (3H, m), 3.78 (2H, s), 4.13 (1H, d, J=13 Hz), 7.19–7.83(9H, m)

Example 24

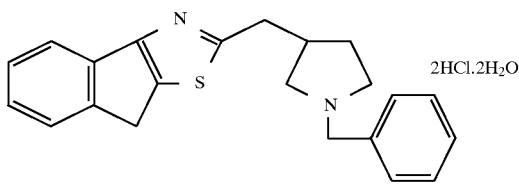

2-[(1-Benzyl-3-pyrrolidinyl)methyl]-8H-indeno[1,2-d]thiazole dihydrochloride dihydrate Starting compound (1-Benzyl-3-pyrrolidine)carbothioamide hydrochloride, 2-bromo-1-indanone Melting point: 118°–121° C. ethyl acetate-methanol

| Elemental analysis for $C_{22}H_{23}N_2S.2HCl.2.2H_2O$ | | | | |
|---|---|---|---|---|
| | C(%) | H(%) | N(%) | S(%) | Cl(%) |
| Calcd.: | 57.56 | 6.24 | 6.10 | 6.99 | 15.45 |
| Found: | 57.62 | 5.82 | 6.16 | 6.99 | 15.44 |

Mass spectrum (m/z): 346 (M$^+$)

Nuclear magnetic resonance spectrum (DMSO-d$_6$, TMS internal standard): δ: 1.72–1.93 (1H, m), 2.10–2.29 (1H, m), 2.78–3.57 (7H, m), 3.91 (2H, s), 4.35–4.38 (2H, m), 7.26 (1H, t), 7.37 (1H, t), 7.53–7.63 (7H, m)

Example 25

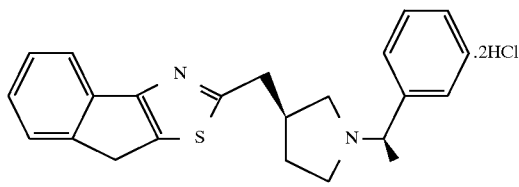

2-[[(S)-1-[(R)-1-phenylethyl]-3-pyrrolidinyl]methyl]-8H-indeno[1,2-d]thiazole dihydrochloride Starting compound

[(S)-1-[(R)-1-phenylethyl]-3-pyrrolidine]thioacetamide hydrochloride, 2-bromo-1-indanone Melting point: 132°–135° C. ethanol-ethyl acetate $[\alpha]_D^{20}$+18.21° (c=1.01, methanol)

Mass spectrum (m/z): 361 (M$^+$+1)

Nuclear magnetic resonance spectrum (DMSO-d$_6$, TMS internal standard): δ: 1.61–1.67 (3H, m), 1.75–2.30 (2H, m), 2.80–3.06 (3H, m), 3.14–3.36 (3H, m), 3.78–4.05 (3H, m), 4.47–4.52 (1H, m), 7.23–7.29 (1H, m), 7.34–7.46 (4H, m), 7.53–7.74 (4H, m), 9.14 (1H, br), 11.66 (1H, br)

Example 26

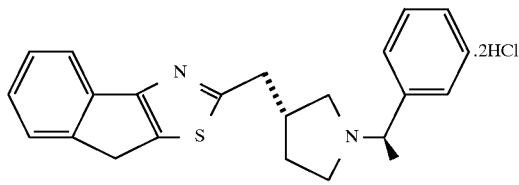

2-[[(R)-1-[(R)-1-phenylethyl]-3-pyrrolidinyl]methyl]8H-indeno[1,2-d]thiazole dihydrochloride Starting compound

[(R)-1-[(R)-1-Phenylethyl]-3-pyrrolidine]thioacetamide hydrochloride, 2-bromo-1-indanone Melting point: 139°–142° C. ethanol-ethyl acetate $[\alpha]_D^{20}$+11.21° (c=1.07, methanol)

Mass spectrum (m/z): 361 (M$^+$+1)

Nuclear magnetic resonance spectrum (DMSO-d$_6$, TMS internal standard): δ: 1.64–1.92 (4H, m), 2.13–2.24 (1H, m), 2.75–3.08 (3H, m), 3.15–3.78 (4H, m), 3.86–3.92 (2H, m), 4.50–4.58 (1H, m), 7.23–7.73(9H, m), 10.13 (1H, br), 11.50 (1H, br)

Example 27

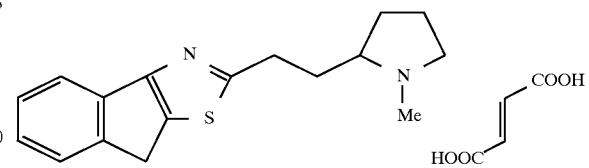

2-[2-(1-Methyl-2-pyrrolidinyl)ethyl]-8H-indeno[1,2-d]thiazole fumarate

Starting compound

2-Bromo-1-indanone, 3-(1-methyl-2-pyrrolidine)propanethioamide hydrochloride

Melting point: 138°–139° C. acetone

| Elemental analysis for $C_{17}H_{20}N_2S.C_4H_4O_4.0.4H_2O$ | | | | |
|---|---|---|---|---|
| | C(%) | H(%) | N(%) | S(%) |
| Calcd.: | 61.87 | 6.13 | 6.87 | 7.87 |
| Found: | 61.84 | 6.08 | 6.82 | 7.84 |

Mass spectrum (m/z): 284 (M$^+$)

Nuclear magnetic resonance spectrum (DMSO-d$_6$, TMS internal standard): δ: 1.62–1.71 (1H, m), 1.81–1.89 (2H, m), 1.91–1.98 (1H, m), 2.11–2.19 (1H, m), 2.30–2.36 (1H, m), 2.53 (3H, s), 2.65–2.69 (1H, m), 2.87 (1H, br), 3.09–3.24 (2H, m), 3.34–3.37 (1H, m), 3.93 (2H, s), 6.57 (2H, s), 7.28 (1H, dd), 7.39 (1H, t), 7.58 (1H, d), 7.66 (1H, d)

Example 28

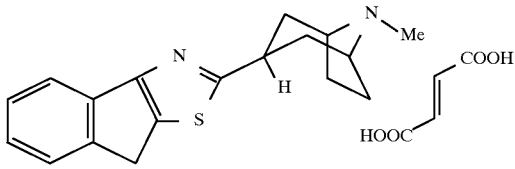

Exo-3-(8H-indeno[1,2-d]thiazol-2-yl)-8-methyl-8-azabicyclo[3.2.1]octane fumarate Starting compound Exo-8-methyl-8-azabicyclo[3.2.1]octane-3-carbothioamide hydrochloride Melting point: 179°–180° C. acetonitrile Mass spectrum (m/z): 296 (M$^+$)

Nuclear magnetic resonance spectrum (DMSO-d$_6$, TMS internal standard): δ: 2.1–2.4 (8H, m), 2.70 (3H, s), 3.71 (1H, quintet), 3.93 (2H, s), 3.97 (2H, s), 6.64 (2H, s), 7.27 (1H, t), 7.37 (1H, t), 7.57 (1H, d), 7.61 (1H, d)

Example 29

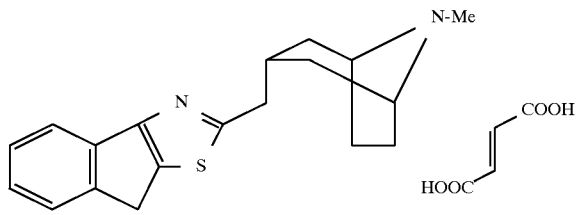

Endo-3-[(8H-indeno[1,2-d]thiazol-2-yl)methyl]-8-methyl-8-azabicyclo[3.2.1]octane fumarate
Starting compound
Endo-8-methyl-8-azabicyclo[3.2.1]octane-3-thioacetamide hydrochloride
Melting point: 211°–213° C. (dec.) acetonitrile-methanol Elemental analysis for $C_{19}H_{22}N_2S.C_4H_4O_4$

|  | C(%) | H(%) | N(%) | S(%) |
|---|---|---|---|---|
| Calcd.: | 64.77 | 6.14 | 6.57 | 7.52 |
| Found: | 64.82 | 6.09 | 6.53 | 7.69 |

Mass spectrum (m/z): 310 (M$^+$)
Nuclear magnetic resonance spectrum (DMSO-$d_6$, TMS internal standard): δ: 1.61 (2H, d), 1.98 (2H, dd), 2.18 (2H, m), 2.23 (2H, m), 2.31 (1H, m), 2.45 (3H, s), 3.29 (2H, d), 3.56 (2H, s), 3.91 (2H, s), 6.48 (2H, s), 7.26 (1H, t), 7.36 (1H, t), 7.56 (1H, d), 7.64 (1H, d)

Example 30

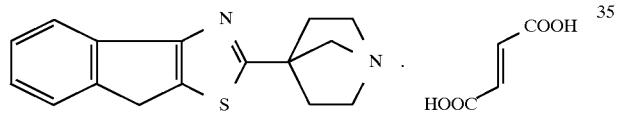

4-(8H-Indeno[1,2-d]thiazol-2-yl)-1-azabicyclo[2.2.1]heptane fumarate
Starting compound
2-Bromo-1-indanone, 1-azabicyclo[2.2.1]heptane-4-carbothioamide hydrochloride
Melting point: 160°–162° C. ethanol
Mass spectrum (m/z): 269 (M$^+$)
Nuclear magnetic resonance spectrum (DMSO-$d_6$, TMS internal standard): δ: 1.94 (2H, m), 2.27 (2H, m), 2.90–3.10 (4H, m), 3.27 (2H, m), 3.94 (2H, s), 6.59 (2H, s), 7.27 (1H, t, J=7.5 Hz), 7.37 (1H, t, J=7.5 Hz), 7.58 (1H, d, J=7.5 Hz), 7.65 (1H, d, J=7.5 Hz)

Example 31

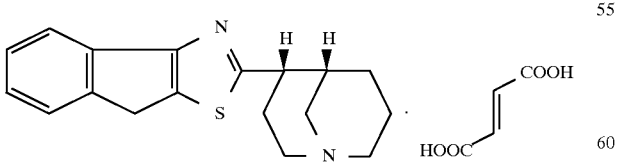

(4R*,5R*)-4-(8H-Indeno[1,2-d]thiazol-2-yl)-1-azabicyclo[3.3.1]nonane fumarate
Starting compound
2-bromo-1-indanone, (4R*,5R*)-1-azabicyclo[3.3.1]nonane-4-carbothioamide Melting point: 195°–196° C. ethanol Elemental analysis for $C_{18}H_{20}N_2S.C_4H_4O_4.0.25H_2O$

|  | C(%) | H(%) | N(%) | S(%) |
|---|---|---|---|---|
| Calcd.: | 63.37 | 5.92 | 6.72 | 7.69 |
| Found: | 63.54 | 5.89 | 6.80 | 7.56 |

Mass spectrum (m/z): 296 (M$^+$)
Nuclear magnetic resonance spectrum (DMSO-$d_6$, TMS internal standard): δ: 1.40–1.80 (3H, m), 2.00–2.40 (2H, m), 2.55–2.70 (1H, m), 3.21 (3H, m), 3.30–3.45 (2H, m), 3.77 (1H, m), 3.94 (2H, s), 6.51 (2H, s), 7.26 (1H, t, J=7.0 Hz), 7.37 (1H, t, J=7.0 Hz), 7.57 (1H, d, J=7.0 Hz), 7.64 (1H, d, J=7.0 Hz)

Example 32

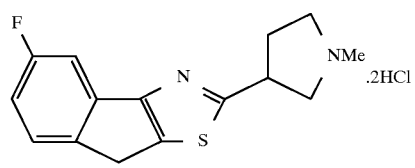

5-Fluoro-2-(1-methyl-3-pyrrolidinyl)-8H-indeno[1,2-d]thiazole dihydrochloride
Starting compound
(1-Methyl-3-pyrrolidine)carbothioamide hydrochloride, 2-bromo-6-fluoro-1-indanone
Melting point: 178°–182° C. methanol-ethyl acetate Elemental analysis for $C_{15}H_{15}N_2SF.2HCl.0.5H_2O$

|  | C(%) | H(%) | N(%) | S(%) | Cl(%) | F(%) |
|---|---|---|---|---|---|---|
| Calcd.: | 50.57 | 5.09 | 7.86 | 9.00 | 19.90 | 5.33 |
| Found: | 50.92 | 5.01 | 7.90 | 8.99 | 19.73 | 5.40 |

Mass spectrum (m/z): 275 (M$^+$+1)
Nuclear magnetic resonance spectrum (DMSO-$d_6$, TMS internal standard): δ: 2.21–2.43 (1H, m), 2.52–2.68 (1H, m), 2.88–2.92 (3H, m), 3.18–3.31 (1H, m), 3.37–3.74 (2H, m), 3.79–4.02 (3H, m), 4.08–4.36 (1H, m), 7.06–7.12 (1H, m), 7.39–7.44 (1H, m), 7.56–7.61 (1H, m), 10.51 (1H, br), 11.80 (1H, br)

Example 33

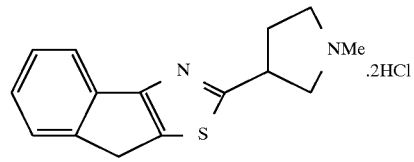

2-(1-Methyl-3-pyrrolidinyl)-4,5-dihydronaphtho[1,2-d]thiazole dihydrochloride
Starting compound
(1-Methyl-3-pyrrolidine)carbothioamide hydrochloride, 2-bromo-1-tetralone
Melting point: 182°–183° C. methanol-ethyl acetate

| Elemental analysis for $C_{16}H_{18}N_2S.2.1HCl$ | | | | |
|---|---|---|---|---|
| | C(%) | H(%) | N(%) | S(%) | Cl(%) |
| Calcd.: | 55.39 | 5.84 | 8.07 | 9.29 | 21.46 |
| Found: | 55.31 | 5.81 | 8.13 | 9.34 | 21.12 |

Mass spectrum (m/z): 271 (M⁺+1)
Nuclear magnetic resonance spectrum (DMSO-$d_6$, TMS internal standard): δ: 2.16–2.36 (1H, m), 2.45–2.63 (1H, m), 2.86–2.91 (3H, m), 3.01 (4H, s), 3.15–3.29 (1H, m), 3.34–3.71 (2H, m), 3.77–4.24 (2H, m), 7.20–7.31 (3H, m), 7.78–7.81 (1H, m), 11.08 (1H, br), 11.71 (1H, br)

Example 34

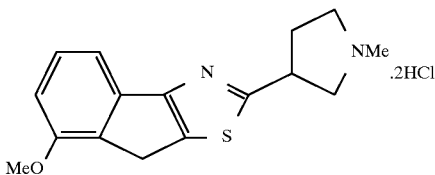

6-Methoxy-2-(1-methyl-3-pyrrolidinyl)-4,5-dihydronaphtho[1,2-d]thiazole dihydrochloride
Starting compound
  (1-Methyl-3-pyrrolidine)carbothioamide hydrochloride, 2-bromo-5-methoxy-1-tetralone
Melting point: 118°–120° C. methanol-ethyl acetate
Mass spectrum (m/z): 301 (M⁺+1)
Nuclear magnetic resonance spectrum (DMSO-$d_6$, TMS internal standard): δ: 2.14–2.36 (1H, m), 2.44–2.63 (1H, m), 2.83–3.02 (7H, m), 3.14–3.28 (1H, m), 3.33–3.73 (2H, m), 3.77–4.24 (5H, m), 6.93–6.96 (1H, m), 7.24–7.29 (1H, m), 7.44–7.46 (1H, m), 9.03 (1H, br), 11.67 (1H, br)

Example 35

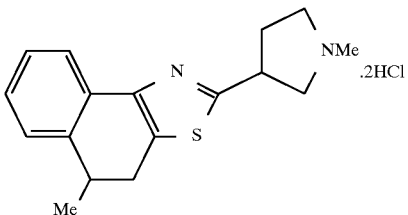

5-Methyl-2-(1-methyl-3-pyrrolidinyl)-4,5-dihydronaphtho[1,2-d]thiazole dihydrochloride
Starting compound
  (1-Methyl-3-pyrrolidine)carbothioamide hydrochloride, 2-bromo-4-methyl-1-tetralone
Melting point: 122°–124° C. methanol-ethyl acetate

| Elemental analysis for $C_{17}H_{20}N_2S.2.1HCl$ | | | | |
|---|---|---|---|---|
| | C(%) | H(%) | N(%) | S(%) | Cl(%) |
| Calcd.: | 56.56 | 6.17 | 7.76 | 8.88 | 20.62 |
| Found: | 56.54 | 6.21 | 7.78 | 8.80 | 20.22 |

Mass spectrum (m/z): 285 (M⁺+1)
Nuclear magnetic resonance spectrum (DMSO-$d_6$, TMS internal standard): δ: 1.22 (3H, d, J=5.4 Hz), 2.15–2.38 (1H, m), 2.45–2.65 (1H, m), 2.82–2.92 (4H, m), 3.12–3.28 (3H, m), 3.34–3.73 (2H, m), 3.77–4.26 (2H, m), 7.24–7.32 (3H, m), 7.82 (1H, d, J=7.3 Hz), 10.37 (1H, br), 11.67 (1H, br)

Example 36

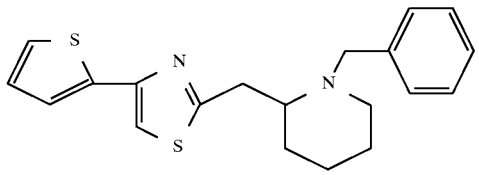

1-Benzyl-2-[[4-(2-thienyl)-2-thiazolyl]methyl]piperidine
Starting compound
  2-(Bromoacetyl)thiophene, (1-benzyl-2-piperidine)thioacetamide hydrochloride
Mass spectrum (m/z): 354 (M⁺)
Nuclear magnetic resonance spectrum (CDCl₃, TMS internal standard): δ: 1.20–1.95 (6H, m), 2.00–2.40 (1H, m), 2.65–3.10 (2H, m), 3.35 (2H, dd, J=5.7 Hz), 3.46 (1H, d, J=13 Hz), 4.04 (1H, d, J=13 Hz), 7.03 (1H, dd, J=4.5 Hz), 7.18–7.55 (7H, m), 7.23 (1H, s)

Example 37

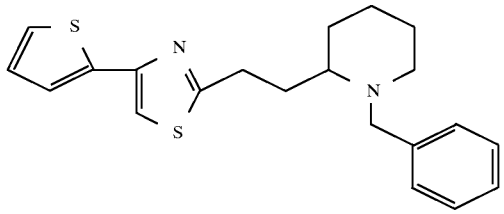

1-Benzyl-2-[2-[4-(2-thienyl)-2-thiazolyl]ethyl]piperidine
Starting compound
  2-(Bromoacetyl)thiophene, 3-(1-benzyl-2-piperidine)propanethioamide hydrochloride
Nuclear magnetic resonance spectrum (CDCl₃, TMS internal standard): δ: 1.3–1.8 (6H, m), 2.0–2.3 (3H, m), 2.3–2.6 (1H, m), 2.7–2.9 (1H, m), 3.0–3.2 (2H, m), 3.31 (2H, d, J=14 Hz), 4.02 (1H, d, J=14 Hz), 7.0–7.4 (9H, m)

Example 38

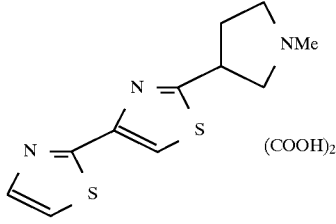

2-(1-Methyl-3-pyrrolidinyl)-4-(2-thiazolyl)thiazole oxalate
Starting compound
  2-(bromoacetyl)thiazole, (1-methyl-3-pyrrolidine)carbothioamide hydrochloride
Melting point: 148°–149° C. ethyl acetate-methanol
Mass spectrum (m/z): 252 (M⁺+1)
Nuclear magnetic resonance spectrum (DMSO-$d_6$, TMS internal standard): δ: 2.21–2.31 (1H, m), 2.50–2.61 (1H, m), 2.84 (3H, s), 3.37 (2H, t), 3.48 (1H, dd), 3.74 (1H, dd), 4.04–4.16 (1H, m), 7.79 (1H, d), 7.92 (1H, d), 8.21 (1H, s)

Example 39

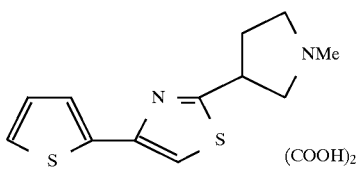

2-(1-Methyl-3-pyrrolidinyl)-4-(2-thienyl)thiazole oxalate

Starting compound 2-(Bromoacetyl)thiophene, (1-methyl-3-pyrrolidine) carbothioamide hydrochloride Melting point: 144° C. acetone Elemental analysis for $C_{12}H_{14}N_2S_2 \cdot C_2H_2O_4$

|  | C (%) | H (%) | N (%) | S (%) |
|---|---|---|---|---|
| Calcd.: | 49.40 | 4.74 | 8.23 | 18.84 |
| Found: | 49.35 | 4.75 | 8.15 | 18.77 |

Mass spectrum (m/z): 251 ($M^+$+1)

Nuclear magnetic resonance spectrum (DMSO-$d_6$, TMS internal standard): δ: 2.19–2.28 (1H, m), 2.49–2.58 (1H, m), 2.85 (3H, s), 3.36 (2H, t), 3.45 (1H, dd), 3.73 (1H, dd), 4.03–4.11 (1H, m), 7.12 (1H, dd), 7.53 (1H, dd), 7.57 (1H, dd), 7.91 (1H, s)

Example 40

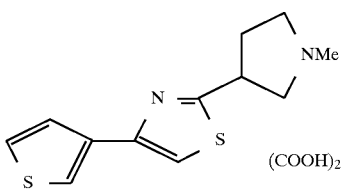

2-(1-Methyl-3-pyrrolidinyl)-4-(3-thienyl)thiazole oxalate

Starting compound 3-(Bromoacetyl)thiophene, (1-methyl-3-pyrrolidine) carbothioamide hydrochloride Melting point: 171° C. acetone Elemental analysis for $C_{12}H_{14}N_2S_2 \cdot C_2H_2O_4$

|  | C (%) | H (%) | N (%) | S (%) |
|---|---|---|---|---|
| Calcd.: | 49.40 | 4.74 | 8.23 | 18.84 |
| Found: | 49.22 | 4.69 | 8.24 | 18.58 |

Mass spectrum (m/z): 251 ($M^+$+1)

Nuclear magnetic resonance spectrum (DMSO-$d_6$, TMS internal standard): δ: 2.19–2.28 (1H, m), 2.50–2.58 (1H, m), 2.85 (3H, s), 3.36 (2H, t), 3.49 (1H, dd), 3.71 (1H, dd), 4.04–4.12 (1H, m), 7.59–7.63 (2H, m), 7.89–7.92 (2H, m)

Example 41

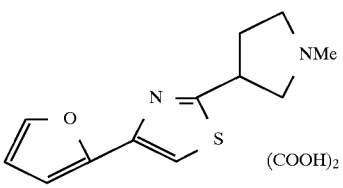

4-(2-Furyl)-2-(1-methyl-3-pyrrolidinyl)thiazole oxalate

Starting compound 2-(Bromoacetyl)furan, (1-methyl-3-pyrrolidine) carbothioamide hydrochloride Melting point: 144° C. acetone Elemental analysis for $C_{12}H_{14}N_2OS \cdot C_2H_2O_4$

|  | C (%) | H (%) | N (%) | S (%) |
|---|---|---|---|---|
| Calcd.: | 51.84 | 4.97 | 8.64 | 9.89 |
| Found: | 51.60 | 4.99 | 8.62 | 9.84 |

Mass spectrum (m/z): 235 ($M^+$+1)

Nuclear magnetic resonance spectrum (DMSO-$d_6$, TMS internal standard): δ: 2.19–2.28 (1H, m), 2.50–2.58 (1H, m), 2.83 (3H, s), 3.35 (2H, t), 3.45 (1H, dd), 3.71 (1H, dd), 4.03–4.12 (1H, m), 6.60 (1H, dd), 6.81 (1H, d), 7.75 (1H, d), 7.77 (1H, s)

Example 42

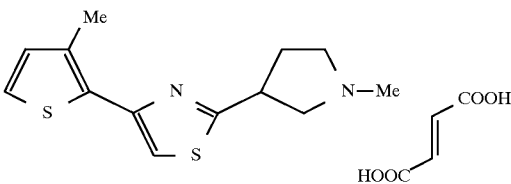

2-(1-Methyl-3-pyrrolidinyl)-4-(3-methyl-2-thienyl) thiazole fumarate

Starting compound (1-Methyl-3-pyrrolidine)carbothioamide hydrochloride, 2-bromoacetyl-3-methylthiazole Melting point: 127°–129° C. acetonitrile-methanol Elemental analysis for $C_{13}H_{16}N_2S \cdot C_4H_4O_4$

|  | C (%) | H (%) | N (%) | S (%) |
|---|---|---|---|---|
| Calcd.: | 53.66 | 5.30 | 7.36 | 16.86 |
| Found: | 53.61 | 5.23 | 7.31 | 16.88 |

Mass spectrum (m/z): 264 ($M^+$)

Nuclear magnetic resonance spectrum (DMSO-$d_6$, TMS internal standard): δ: 2.03–2.11 (1H, m), 2.37–2.46 (4H, m), 2.49 (3H, s), 2.78–2.84 (1H, m), 2.89–2.97 (2H, m), 3.15–3.19 (1H, m), 6.57 (2H, s), 6.96 (1H, d), 7.40 (1H, d), 7.59 (1H, s)

Example 43

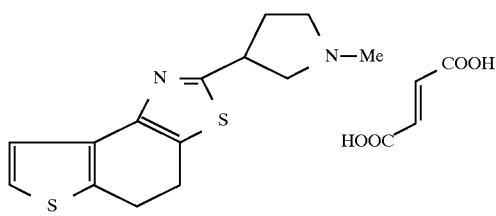

2-(1-Methyl-3-pyrrolidinyl)-4,5-dihydrothieno[3,2-e]benzothiazole fumarate

Starting compound (1-Methyl-3-pyrrolidine)carbothioamide hydrochloride, 5-bromo-4,5,6,7-tetrahydrobenzo[b]thiophen-4-one
Melting point: 165°–169° C. methanol Elemental analysis for $C_{14}H_{16}N_2S_2 \cdot C_4H_4O_4$

|        | C (%) | H (%) | N (%) | S (%) |
|--------|-------|-------|-------|-------|
| Calcd.: | 55.08 | 5.14  | 7.14  | 16.34 |
| Found:  | 55.10 | 5.08  | 7.08  | 16.38 |

Mass spectrum (m/z): 276 (M⁺)

Nuclear magnetic resonance spectrum (DMSO-$d_6$, TMS internal standard): δ: 2.00–2.08 (1H, m), 2.33–2.42 (1H, m), 2.45 (3H, s), 2.75 (1H, q), 2.83–2.89 (2H, m), 3.08–3.11 (5H, m), 3.78–3.85 (1H, m), 6.58 (2H, s), 7.27 (1H, d), 7.38 (1H, d)

Example 44

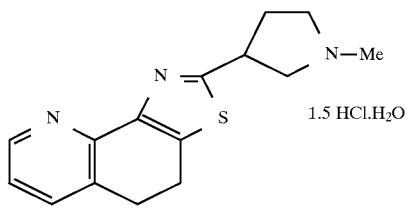

2-(1-Methyl-3-pyrrolidinyl)-4,5-dihydrothiazolo[5,4-h]quinoline sesquihydrochloride monohydrate
Melting point: 176°–179° C. (dec.) ethyl acetate-methanol Elemental analysis for $C_{15}H_{17}N_3S \cdot 1.55HCl \cdot H_2O$

|        | C (%) | H (%) | N (%) | S (%) | Cl (%) |
|--------|-------|-------|-------|-------|--------|
| Calcd.: | 52.08 | 5.99  | 12.15 | 9.27  | 15.89  |
| Found:  | 51.82 | 5.91  | 12.11 | 9.06  | 15.93  |

Mass spectrum (m/z): 271 (M⁺)

Nuclear magnetic resonance spectrum (DMSO-$d_6$, TMS internal standard): δ: 2.13–2.35 (1H, m), 2.55–2.70 (1H, m), 2.93 (3H, s), 3.17 (2H, s), 3.22–4.28 (7H, m), 7.47–7.61 (1H, m), 8.00–8.18 (1H, m), 8.49–8.54 (1H, m)

Example 45

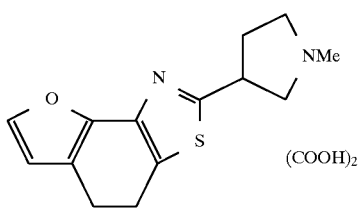

2-(1-Methyl-3-pyrrolidinyl)-4,5-dihydrofuro[2,3-e]benzothiazole oxalate

Starting compound

6-Bromo-7-oxo-4,5,6,7-tetrahydrobenzofuran, (1-methyl-3-pyrrolidine)carbothioamide hydrochloride
Melting point: 165°–168° C. ethyl acetate-methanol
Mass spectrum (m/z): 260 (M⁺)

Nuclear magnetic resonance spectrum (DMSO-$d_6$, TMS internal standard): δ: 2.19–2.22 (1H, m), 2.50 (1H, m), 2.80 (3H, s), 2.83 (2H, t), 3.07 (2H, t), 3.31 (2H, m), 3.42 (1H, m), 3.61 (1H, m), 4.00 (1H, m), 6.52 (1H, d), 7.59 (1H, d)

Example 46

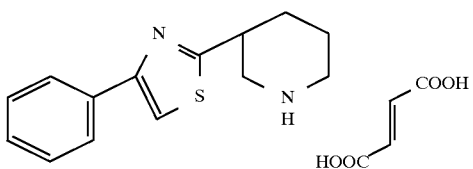

4-Phenyl-2-(3-piperidyl)thiazole fumarate

Starting compound
2-Bromoacetophenone, 3-piperidinecarbothioamide
Melting point: 145°–148° C. ethanol-acetonitrile Elemental analysis for $C_{14}H_{16}N_2S \cdot C_4H_4O_4$

|        | C (%) | H (%) | N (%) | S (%) |
|--------|-------|-------|-------|-------|
| Calcd.: | 59.98 | 5.59  | 7.77  | 8.90  |
| Found:  | 59.63 | 5.54  | 7.70  | 8.98  |

Mass spectrum (m/z): 244 (M⁺)

Nuclear magnetic resonance spectrum (DMSO-$d_6$, TMS internal standard): δ: 1.70–1.85 (3H, m), 2.15–2.25 (1H, m), 2.75–2.85 (1H, m), 3.02 (1H, dd), 3.18 (1H, d), 3.40–3.45 (1H, m), 3.53 (1H, d), 6.48 (2H, s), 7.34 (1H, dd), 7.44 (2H, dd), 7.96 (2H, d), 8.04 (1H, s)

Example 47

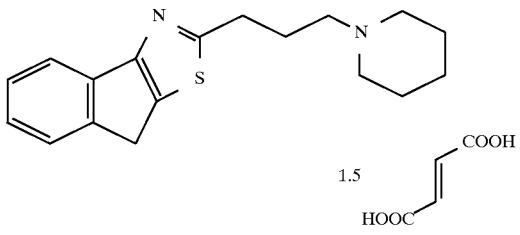

In 10 ml of 4N solution of hydrogen chloride in ethyl acetate, 1.11 g of 4-piperidinobutylonitrile was dissolved. Then, 1.22 ml of O,O-diethyl dithiophosphate was added to the resulting solution, followed by stirring at room temperature for 20 hours. The precipitate formed was collected by filtration and washed successively with ethyl acetate and diethyl ether, whereby 1.02 g of 4-piperidinobutanethioamide hydrochloride was obtained. Then, 0.95 g of 2-bromo-1-indanone was added, and the resulting mixture was dissolved in 10 ml of isopropanol, followed by heating under reflux for 7 hours. The precipitate formed was collected by filtration and then distributed between chloroform and a saturated aqueous solution of sodium bicarbonate. The organic layer was separated, washed successively with water and a saturated aqueous solution of sodium chloride and then dried over anhydrous sodium sulfate. The solvent was evaporated, and the resulting residue was dissolved in methanol. Fumaric acid was added to the resulting solution. The crystals formed were collected by filtration and washed successively with methanol and diethyl ether, followed by recrystallization from methanol, whereby 510 mg of 2-(3-piperidinopropyl)-8H-indeno[1,2-d]thiazole sesquifumarate was obtained.

Melting point: 133°–135° C. methanol

Elemental analysis for $C_{18}H_{22}N_2S.1.5C_4H_4O_4$

|  | C (%) | H (%) | N (%) | S (%) |
|---|---|---|---|---|
| Calcd.: | 59.86 | 6.07 | 5.82 | 6.66 |
| Found: | 59.86 | 5.80 | 6.08 | 6.68 |

Mass spectrum (m/z): 398 ($M^+$)

Nuclear magnetic resonance spectrum (DMSO-$d_6$, TMS internal standard): δ: 1.45–1.47 (2H, m), 1.60–1.66 (4H, m), 2.04–2.12 (2H, m), 2.77–2.81 (6H, m), 3.12 (2H, t), 3.91 (2H, s), 6.57 (1H, s), 7.25 (1H, t), 7.36 (1H, t), 7.56 (1H, d), 7.63 (1H, d)

The compounds of the following Examples 48–51 were obtained by the same manner as described in Example 47.

Example 48

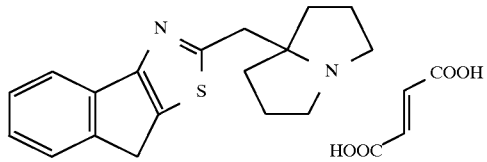

5-[(8H-Indeno[1,2-d]thiazol-2-yl)methyl]-1-azabicyclo[3.3.0]octane fumarate
Starting compound
1-Azabicyclo[3.3.0]octan-5-acetonitrile
Melting point: 201°–202° C. methanol Elemental analysis for $C_{18}H_{20}N_2S.C_4H_4O_4$

|  | C (%) | H (%) | N (%) | S (%) |
|---|---|---|---|---|
| Calcd.: | 64.06 | 5.86 | 6.79 | 7.77 |
| Found: | 63.79 | 5.89 | 6.74 | 7.79 |

Mass spectrum (m/z): 297 ($M^+$+1)

Nuclear magnetic resonance spectrum (DMSO-$d_6$, TMS internal standard): δ: 1.79–1.85 (2H, m), 2.00–2.03 (4H, m), 2.31–2.36 (2H, m), 2.87–2.92 (2H, m), 3.52 (2H, s), 3.57–3.62 (2H, m), 3.84 (2H, s), 6.69 (2H, s), 7.24 (1H, t), 7.35 (1H, t), 7.51 (1H, d), 7.69 (1H, d)

Example 49

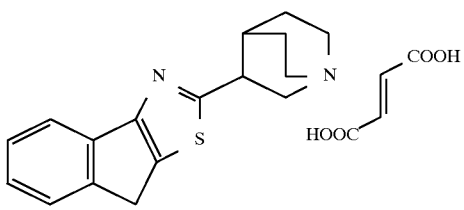

2-(3-Quinuclidinyl)-8H-indeno[1,2,-d]thiazole fumarate

Starting compound

3-Quinuclidinecarbonitrile
Melting point: 199°–202° C. methanol

Elemental analysis for $C_{17}H_{18}N_2S.C_4H_4O_4$

|  | C (%) | H (%) | N (%) | S (%) |
|---|---|---|---|---|
| Calcd.: | 63.30 | 5.56 | 7.03 | 8.05 |
| Found: | 63.50 | 5.67 | 6.95 | 7.95 |

Mass spectrum (m/z): 283 ($M^+$+1)

Nuclear magnetic resonance spectrum (DMSO-$d_6$, TMS internal standard): δ: 1.62–1.99 (4H, m), 2.29–2.30 (1H, m), 3.02–3.17 (4H, m), 3.53–3.75 (3H, m), 3.94 (2H, s), 6.52 (2H, s), 7.27 (1H, t), 7.35 (1H, t), 7.51 (1H, d), 7.69 (1H, d)

Example 50

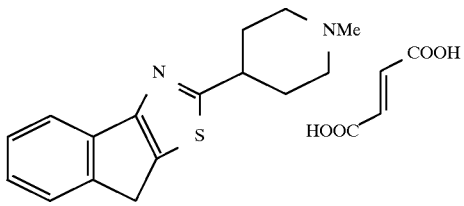

2-(1-Methyl-4-piperidyl)-8H-indeno[1,2-d]thiazole fumarate

Starting compound (1-Methyl-4-piperidine)carbonitrile
Melting point: 189°–191° C. acetonitrile-methanol Elemental analysis for $C_{16}H_{18}N_2S.C_4H_4O_4.0.2H_2O$

|  | C (%) | H (%) | N (%) | S (%) |
|---|---|---|---|---|
| Calcd.: | 61.58 | 5.79 | 7.18 | 8.22 |
| Found: | 61.68 | 5.75 | 7.11 | 8.41 |

Mass spectrum (m/z): 270 ($M^+$)

Nuclear magnetic resonance spectrum (DMSO-$d_6$, TMS internal standard): δ: 1.96 (2H, q), 2.20 (2H, d), 2.52 (3H, s), 2.64 (2H, t), 3.19–3.27 (3H, m), 3.92 (2H, s), 6.58 (2H, s), 7.26 (1H, t), 7.37 (1H, t), 7.57 (1H, d), 7.64 (1H, d)

Example 51

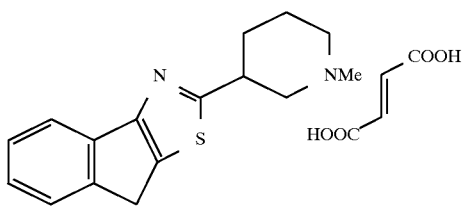

2-(1-Methyl-3-piperidyl)-8H-indeno[1,2-d]thiazole fumarate

Starting compound (1-Methyl-3-piperidine)carbonitrile
Melting point: 170°–172° C. acetonitrile-isopropanol Elemental analysis for $C_{16}H_{18}N_2S \cdot C_4H_4O_4 \cdot 0.3H_2O$

|  | C (%) | H (%) | N (%) | S (%) |
|---|---|---|---|---|
| Calcd.: | 61.30 | 5.81 | 7.15 | 8.18 |
| Found: | 61.03 | 5.72 | 7.18 | 7.91 |

Mass spectrum (m/z): 270 (M⁺)

Nuclear magnetic resonance spectrum (DMSO-$d_6$, TMS internal standard): δ: 1.55–1.73 (2H, m), 1.76–1.81 (1H, m), 2.07–2.10 (1H, m), 2.22 (1H, t), 2.35 (1H, s), 2.43 (1H, t), 2.84 (1H, d), 3.20 (1H, d), 3.35–3.41 (1H, m), 3.91 (2H, s), 6.59 (2H, s), 7.25 (1H, t), 7.36 (1H, t), 7.56 (1H, d), 7.63 (1H, d)

Example 52

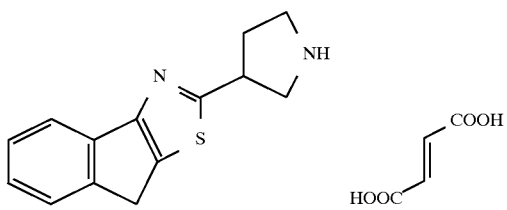

To a solution of 0.86 g of 2-(1-benzyl-3-pyrrolidinyl)-8H-indeno[1,2-d]thiazole in 5 ml of dichloroethane was added 5 ml of 1-chloroethyl chloroformate, followed by heating under reflux for 2 hours. After cooling, the solvent was evaporated and 10 ml of methanol was added to the resulting residue, followed by heating under reflux for 2 hours. After the completion of the reaction, ethyl acetate was added to the reaction mixture, followed by extraction with 1N hydrochloric acid. The extract was neutralized with sodium bicarbonate, followed by the extraction with chloroform. The extract was dried over anhydrous magnesium sulfate and the solvent was evaporated, whereby 0.18 g of 2-(3-pyrrolidinyl)-8H-indeno[1,2-d]thiazole was obtained. The resulting product was dissolved in methanol. Fumaric acid was added to the resulting solution to cause crystallization, and the crystals were recrystallized from acetonitrile-methanol to obtain a fumarate.

Melting point: 185°–188° C. acetonitrile-methanol

Elemental analysis for $C_{14}H_{14}N_2S \cdot C_4H_4O_4 \cdot 0.1H_2O$

|  | C (%) | H (%) | N (%) | S (%) |
|---|---|---|---|---|
| Calcd.: | 60.02 | 5.09 | 7.78 | 8.90 |
| Found: | 59.82 | 5.14 | 7.72 | 8.90 |

Mass spectrum (m/z): 242 (M⁺)

Nuclear magnetic resonance spectrum (DMSO-$d_6$, TMS internal standard): δ: 2.11–2.20 (1H, m), 2.40–2.48 (1H, m), 3.18–3.25 (1H, m), 3.29–3.36 (2H, m), 3.63 (1H, dd), 3.89–3.99 (3H, m), 6.47 (2H, s), 7.27 (1H, t), 7.37 (1H, t), 7.57 (1H, d), 7.65 (1H, d)

The compounds of the following Examples 53–60 were obtained by the same manner as described in Example 52.

Example 53

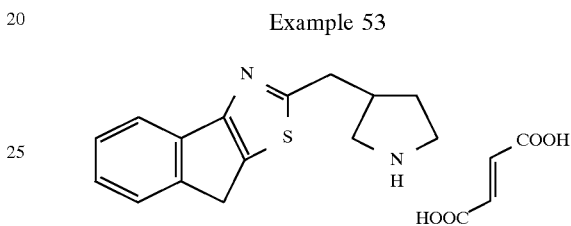

2-(3-Pyrrolidinylmethyl)-8H-indeno[1,2-d]thiazole fumarate

Starting compound

2-[(1-benzyl-3-pyrrolidinyl)methyl]-8H-indeno[1,2-d]thiazole
Melting point: 183°–185° C. acetonitrile-methanol Elemental analysis for $C_{15}H_{16}N_2S \cdot C_4H_4O_4 \cdot 0.3H_2O$

|  | C (%) | H (%) | N (%) | S (%) |
|---|---|---|---|---|
| Calcd.: | 60.40 | 5.50 | 7.41 | 8.49 |
| Found: | 60.35 | 5.32 | 7.58 | 8.43 |

Mass spectrum (m/z): 256 (M⁺)

Nuclear magnetic resonance spectrum (DMSO-$d_6$, TMS internal standard): δ: 1.63–1.72 (1H, d), 2.04–2.12 (1H, m), 2.68–2.76 (1H, m), 2.91 (1H, dd), 3.08–3.35 (5H, m), 3.92 (2H, s), 6.43 (2H, s), 7.26 (1H, t), 7.34 (1H, t), 7.57 (1H, d), 7.64 (1H, d)

Example 54

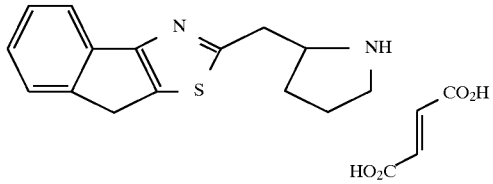

2-(2-Pyrrolidinylmethyl)-8H-indeno[1,2-d]thiazole fumarate

Starting compound

2-[(1-Benzyl-2-pyrrolidinyl)methyl]-8H-indeno[1,2-d]thiazole

Melting point: 148° C. (dec.) acetonitrile

Elemental analysis for $C_{15}H_{16}N_2S \cdot C_4H_4O_4 \cdot H_2O$

|  | C (%) | H (%) | N (%) | S (%) |
|---|---|---|---|---|
| Calcd.: | 58.45 | 5.68 | 7.17 | 8.21 |
| Found: | 58.30 | 5.26 | 7.01 | 7.91 |

Mass spectrum (m/z): 257 ($M^+$+1)
Nuclear magnetic resonance spectrum (DMSO-$d_6$, TMS internal standard): δ: 1.64–1.74 (1H, m), 1.80–1.97 (2H, m), 2.04–2.13 (1H, m), 3.09–3.27 (2H, m), 3.40–3.59 (2H, m), 3.85–3.92 (3H, m), 6.48 (2H, s), 7.24–7.28 (1H, m), 7.35–7.39 (m, 1H), 7.57 (1H, d, J=7.8 Hz), 7.66 (1H, d, J=7.3 Hz)

Example 55

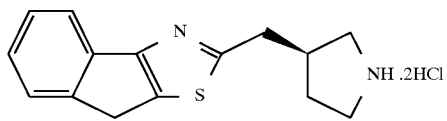

(S)-2-(3-Pyrrolidinylmethyl)-8H-indeno[1,2-d]thiazole dihydrochloride
Starting compound
2-[[(S)-1-[(R)-1-phenylethyl]-3-pyrrolidinyl]methyl]-8H-indeno[1,2-d]thiazole
Melting point: 152° C. (dec.) ethanol-ethyl acetate
$[\alpha]_D^{25}$+5.95° (c=0.89, methanol)

Elemental analysis for $C_{15}H_{16}N_2S \cdot 2HCl \cdot 0.2H_2O$

|  | C (%) | H (%) | N (%) | S (%) | Cl (%) |
|---|---|---|---|---|---|
| Calcd.: | 54.12 | 5.57 | 8.42 | 9.63 | 21.30 |
| Found: | 54.11 | 5.34 | 8.37 | 9.44 | 21.00 |

Mass spectrum (m/z): 257 ($M^+$+1)
Nuclear magnetic resonance spectrum (DMSO-$d_6$, TMS internal standard): δ: 1.65–1.75 (1H, m), 2.06–2.15 (1H, m), 2.71–2.79 (1H, m), 2.90–2.98 (1H, m), 3.10–3.39 (5H, m), 3.92 (2H, s), 7.24–7.28 (1H, m), 7.37 (1H, t, J=7.3 Hz), 7.57 (1H, d, J=7.3 Hz), 7.65 (1H, d, J=7.8 Hz), 8.86 (1H, br), 9.46 (2H, br)

The resulting compound was analyzed by the same manner as described later in Example 61. The result showed 99% enantiomeric excess.

Example 56

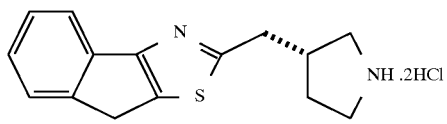

(R)-2-(3-Pyrrolidinylmethyl)-8H-indeno[1,2-d]thiazole dihydrochloride
Starting compound
2-[[(R)-1-[(R)-1-phenylethyl]-3-pyrrolidinyl]methyl]-8H-indeno[1,2-d]thiazole
Melting point: 149° C. (dec.) methanol-ethyl acetate
$[\alpha]_D^{25}$−4.71° (c=0.89, methanol)

Elemental analysis for $C_{15}H_{16}N_2S \cdot 2HCl$

|  | C (%) | H (%) | N (%) | S (%) | Cl (%) |
|---|---|---|---|---|---|
| Calcd.: | 54.71 | 5.51 | 8.51 | 9.74 | 21.53 |
| Found: | 54.40 | 5.52 | 8.47 | 9.68 | 21.63 |

Mass spectrum (m/z): 257 ($M^+$+1)
Nuclear magnetic resonance spectrum (DMSO-$d_6$, TMS internal standard): δ: 1.66–1.76 (1H, m), 2.06–2.15 (1H, m), 2.72–2.80 (1H, m), 2.91–2.99 (1H, m), 3.09–3.19 (1H, m), 3.21–3.38 (4H, m), 3.92 (1H, s), 7.25–7.29 (1H, m), 7.38 (1H, t, J=7.3), 7.57 (1H, d, J=7.8), 7.67 (1H, d, J=7.3), 9.69 (2H, br), 11.03 (1H, br)

The resulting compound was analyzed by the same manner as described later in Example 61. The analytical results showed 98% enantiomeric excess.

Example 57

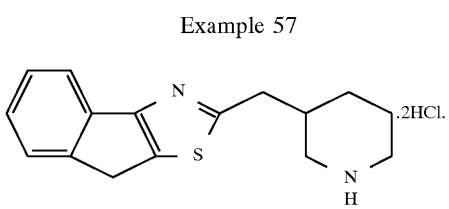

2-(3-Piperidylmethyl)-8H-indeno[1,2-d]thiazole dihydrochloride
Starting compound
2-[(1-Benzyl-3-piperidyl)methyl]-8H-indeno[1,2-d]thiazole
Melting point: 163° C. (dec.) methanol-ethyl acetate Elemental analysis for $C_{16}H_{18}N_2S \cdot 2HCl \cdot 0.5H_2O$

|  | C (%) | H (%) | N (%) | S (%) | Cl (%) |
|---|---|---|---|---|---|
| Calcd.: | 54.54 | 6.01 | 7.95 | 9.10 | 20.12 |
| Found: | 54.25 | 5.78 | 7.88 | 9.05 | 20.03 |

Mass spectrum (m/z): 271 ($M^+$+1)
Nuclear magnetic resonance spectrum (DMSO-$d_6$, TMS internal standard): δ: 1.25–1.34 (1H, m), 1.63–1.83 (3H, m), 2.27–2.36 (1H, m), 2.66–2.79 (2H, m), 3.02–3.27 (4H, m), 3.92 (2H, s), 7.26 (1H, dd, J=6.3, 7.3 Hz), 7.37 (1H, t, J=7.3 Hz), 7.50–7.70 (3H, m), 9.10–9.50 (2H, m)

Example 58

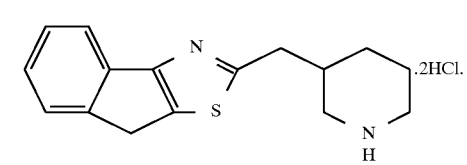

2-[(1,2,3,6-tetrahydro-5-pyridyl)methyl]-8H-indeno[1,2-d]thiazole fumarate
Starting compound
2-(3-Pyridylmethyl)-8H-indeno[1,2-d]thiazole
Melting point: 168° C. methanol-diethyl ether Elemental analysis for $C_{16}H_{16}N_2S \cdot C_4H_4O_4 \cdot 0.1H_2O$

|  | C (%) | H (%) | N (%) | S (%) |
|---|---|---|---|---|
| Calcd.: | 62.19 | 5.27 | 7.25 | 8.30 |
| Found: | 61.24 | 5.15 | 7.11 | 8.49 |

Mass spectrum (m/z): 268 (M$^+$)

Nuclear magnetic resonance spectrum (DMSO-d$_6$, TMS internal standard): δ: 2.20 (2H, br), 2.98 (2H, t), 3.46 (2H, s), 3.81 (2H, s), 3.91 (2H, s), 5.82 (1H, br), 6.45 (2H, s), 7.26 (1H, t), 7.37 (1H, t), 7.56 (1H, d), 7.64 (1H, d)

Example 59

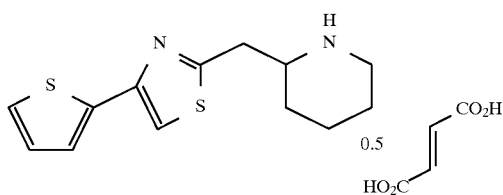

2-[[4-(2-Thienyl)-2-thiazolyl]methyl]piperidine hemifumarate

Starting compound

1-Benzyl-2-[[4-(2-thienyl)-2-thiazolyl]methyl]piperidine
Melting point: 181°–183° C. methanol-ethyl acetate Elemental analysis for $C_{13}H_{16}N_2S_2 \cdot 0.5C_4H_4O_4$

|  | C (%) | H (%) | N (%) | S (%) |
|---|---|---|---|---|
| Calcd.: | 55.87 | 5.63 | 8.69 | 19.89 |
| Found: | 55.83 | 5.61 | 8.60 | 19.83 |

Mass spectrum (m/z): 264 (M$^+$)

Nuclear magnetic resonance spectrum (CDCl$_3$, TMS internal standard)(in the form of a free compound) δ: 1.00–1.95 (6H, m), 2.11 (1H, s), 2.43–2.77 (1H, m), 2.85–3.25 (4H, m), 7.01 (1H, dd, J=4.5 Hz), 7.17 (1H, s), 7.23 (1H, dd, J=1.5 Hz), 7.41 (1H, dd, J=1.4 Hz)

Example 60

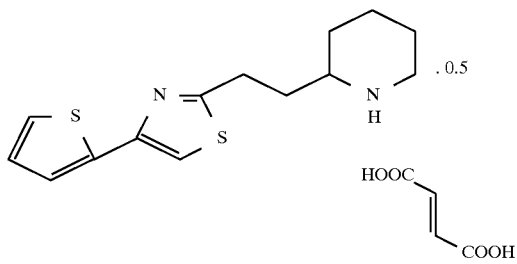

2-[2-[4-(2-Thienyl)-2-thiazolyl]ethyl]piperidine hemifumarate:

Starting compound

1-Benzyl-2-[2-[4-(2-thienyl)-2-thiazolyl]ethyl]piperidine
Melting point: 176°–180° C. ethanol
Mass spectrum (m/z): 279 (M$^+$+1)

Nuclear magnetic resonance spectrum (DMSO-d$_6$, TMS internal standard): δ: 1.3–1.5 (3H, m), 1.62 (1H, m), 1.8–2.0 (4H, m), 2.69 (1H, dd, J=9, 12 Hz), 2.84 (1H, m), 3.1 (3H, m), 6.41 (1H, s), 7.10 (1H, dd, J=3, 5 Hz), 7.50 (1H, dd, J=1, 5 Hz), 7.54 (1H, dd, J=1, 3 Hz), 7.80 (1H, s)

Example 61

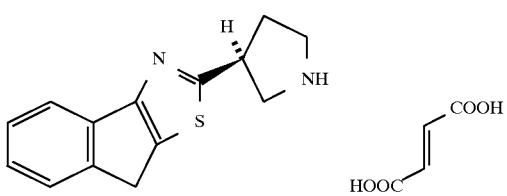

To a solution of 0.78 g of 2-(3-pyrrolidinyl)-8H-indeno[1,2-d]thiazole in methanol was added 1.09 g of (–)-O,O'-dibenzoyltartaric acid monohydrate, and then water was added. The crystals precipitated were collected by filtration and recrystallized three times from methanol-water, whereby 0.45 g of 2-(3-pyrrolidinyl)-8H-indeno[1,2-d]thiazole (–)-dibenzoyltartrate monohydrate was obtained. The absolute configuration of this compound was assigned as S by X-ray diffraction studies.

Then, saturated sodium bicarbonate was added to this salt, followed by extraction with chloroform. The extract was dried over anhydrous magnesium sulfate. The residue obtained by evaporation of the solvent was dissolved in methanol. To the resulting solution, fumaric acid was added for crystallization, and the crystals were recrystallized from methanol-acetonitrile, whereby (S)-2-(3-pyrrolidinyl)-8H-indeno[1,2-d]thiazole fumarate was obtained. This product was analyzed by the high-performance liquid chromatography as "CHIRALCEL OD" (Daicel Chemical Ind., Ltd.) eluted with ethanol/hexane/diethylamine. The result showed 98% enantiomeric excess.

Melting point: 190°–191° C. acetonitrile-methanol

Elemental analysis for $C_{14}H_{14}N_2S \cdot C_4H_4O_4$

|  | C (%) | H (%) | N (%) | S (%) |
|---|---|---|---|---|
| Calcd.: | 60.32 | 5.06 | 7.82 | 8.95 |
| Found: | 60.25 | 5.01 | 7.63 | 8.93 |

Mass spectrum (m/z): 242 (M$^+$)

Nuclear magnetic resonance spectrum (DMSO-d$_6$, TMS internal standard): δ: 2.12–2.19 (1H, m), 2.38–2.47 (1H, m), 3.17–3.23 (1H, m), 3.27–3.34 (2H, m), 3.61 (1H, dd), 3.90–3.97 (3H, m), 6.47 (2H, s), 7.27 (1H, t), 7.37 (1H, t), 7.57 (1H, d), 7.64 (1H, d)

Example 62

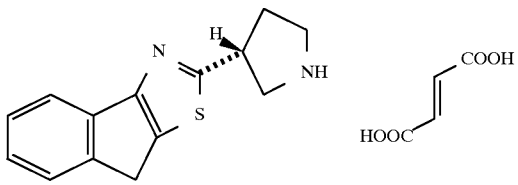

The mother liquid obtained after crystallization in Example 61 was neutralized with calcium carbonate, followed by extraction with chloroform. The extract was dried over anhydrous magnesium sulfate, and the solvent was evaporated. Then, 0.727 g of (+)-O,O'-dibenzoyltartaric acid monohydrate was added to a methanol solution of the resulting residue (0.52 g). Water was added and the crystals precipitated were recrystallized four times from methanol-water, whereby 0.43 g of 2-(3-pyrrolidinyl)-8H-indeno[1,2-d]thiazole (+)-dibenzoyltartrate monohydrate was obtained. The absolute configuration of this compound was assigned as R by X-ray diffraction studies.

This salt was treated as in Example 61, whereby (R)-2-(3-pyrrolidinyl)-8H-indeno[1,2-d]thiazole fumarate was obtained. This compound was analyzed by the same manner as described above in Example 61. The result showed 99% enantiomeric excess.

Melting point: 191°–192° C. acetonitrile-methanol

| Elemental analysis for $C_{14}H_{14}N_2S.C_4H_4O_4$ | | | | |
|---|---|---|---|---|
| | C(%) | H(%) | N(%) | S(%) |
| Calcd.: | 60.32 | 5.06 | 7.82 | 8.95 |
| Found: | 60.14 | 4.93 | 7.85 | 8.76 |

Mass spectrum (m/z): 242 ($M^+$)

Nuclear magnetic resonance spectrum (DMSO-$d_6$, TMS internal standard): δ: 2.10–2.17 (1H, m), 2.37–2.45 (1H, m), 3.14–3.20 (1H, m), 3.24–3.30 (2H, m), 3.57 (1H, dd), 3.87–3.93 (3H, m), 6.47 (2H, s), 7.27 (1H, t), 7.37 (1H, t), 7.57 (1H, d), 7.64 (1H, d)

Example 63

In 100 ml of 4N solution of hydrogen chloride in ethyl acetate, 5.10 g of a diastereomer mixture of (5S)-1-azabicyclo[3.3.0]octane-3-carbonitrile was dissolved. Then, 7 g of O,O-diethyl dithiophosphate was added, followed by stirring at room temperature for 16 hours. After the solvent was evaporated, the residue was washed with ethyl acetate, followed by drying under reduce pressure, whereby (5S)-1-azabicyclo[3.3.0]octane-3-carbothioamide was obtained. The resulting product was dissolved in 150 ml of isopropanol, 6.3 g of 2-bromo-1-indanone and 3.7 g of calcium carbonate were added, and the mixture was heated under reflux for 5 hours. After cooling, the insoluble matter was removed by filtration and the solvent was evaporated. To the resulting residue, ethyl acetate and 1N hydrochloric acid were added. The aqueous layer was separated, and neutralized with sodium bicarbonate, followed by extraction with chloroform. The extract was dried over anhydrous sodium sulfate. The solvent was evaporated, and the resulting residue was subjected to preparative medium-pressure column chromatography, whereby 0.32 g of a (3R,5S) form compound (Example 63A) and 0.18 g of a (3S,5S) form compound (Example 63B) of 3-(8H-indeno[1,2-d]thiazol-2-yl)-1-azabicyclo[3.3.0]octane was obtained from the fraction eluted with chloroform-methanol-aqueous ammonia (200:10:1).

The (3R,5S) form compound (Example 63A) was dissolved in methanol. Fumaric acid was added to and dissolved in the resulting solution, followed by evaporation of the solvent. The residue was crystallized from acetone to form a corresponding fumarate. The (3S,5S) form compound (Example 63B) was crystallized from petroleum ether.

The (3R,5S) form compound was analyzed by the same manner as described above in Example 61. The result showed 96% enantiomeric excess.

As the (3S,5S) form compound was analyzed similarly, it showed 99% enantiomeric excess.

Example 63A

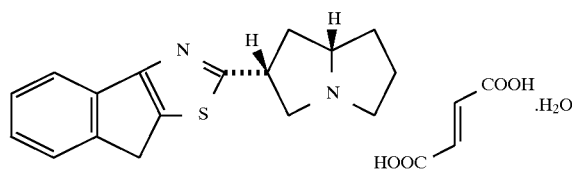

Melting point: 155°–156° C. acetone $[\alpha]_D^{25}$ −8.00 (c=0.50, methanol)

| Elemental analysis for $C_{17}H_{18}N_2S.C_4H_4O_4.H_2O$ | | | | |
|---|---|---|---|---|
| | C(%) | H(%) | N(%) | S(%) |
| Calcd.: | 60.56 | 5.81 | 6.73 | 7.70 |
| Found: | 60.63 | 5.74 | 6.88 | 7.65 |

Mass spectrum (m/z): 283 ($M^+$+1)

Nuclear magnetic resonance spectrum (DMSO-$d_6$, TMS internal standard): δ: 1.81–2.15 (6H, m), 2.66–2.73 (1H, m), 3.11–3.29 (3H, m), 3.93 (2H, s), 3.96–4.05 (1H, m), 4.13–4.20 (1H, m), 6.52 (2H, s), 7.27 (1H, dt), 7.38 (1H, t), 7.57 (1H, d), 7.64 (1H, d)

Example 63B

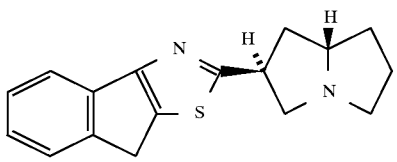

Melting point: 79°–81° C. petroleum ether $[\alpha]_D^{25}$ −8.39° (c=0.50, chloroform)

| Elemental analysis for $C_{17}H_{18}N_2S.0.1H_2O$ | | | | |
|---|---|---|---|---|
| | C(%) | H(%) | N(%) | S(%) |
| Calcd.: | 71.84 | 6.45 | 9.86 | 11.28 |
| Found: | 71.94 | 6.64 | 9.81 | 10.90 |

Mass spectrum (m/z): 282 ($M^+$)

Nuclear magnetic resonance spectrum (CDCl$_3$, TMS internal standard): 1.42–1.51 (1H, m), 1.73–1.92 (2H, m), 2.05–2.15 (2H, m), 2.32–2.39 (1H, m), 2.59–2.64 (1H, m), 3.16–3.22 (3H, m), 3.66–3.88 (4H, m), 7.28 (1H, dt), 7.36 (1H, t), 7.48 (1H, d), 7.76 (1H, d)

The compounds of the following Examples 64–69 were obtained by the same manner as described in Example 63.

Example 64

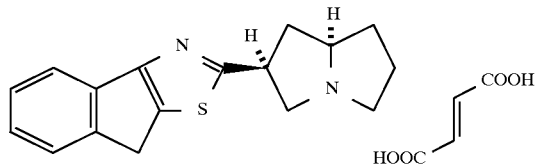

(3S,5R)-3-(8H-indeno[1,2-d]thiazol-2-yl)-1-azabicyclo [3.3.0]octane fumarate

Starting compound (5R)-1-azabicyclo[3.3.0]octane-3-carbonitrile, 2-bromo-1-indanone Melting point: 157°–158° C. acetone $[\alpha]_D^{25}$+6.79 (c=0.50, methanol)

| Elemental analysis for $C_{17}H_{18}N_2S.C_4H_4O_4.0.5H_2O$ | | | | |
|---|---|---|---|---|
| | C(%) | H(%) | N(%) | S(%) |
| Calcd.: | 61.90 | 5.69 | 6.87 | 7.87 |
| Found: | 62.07 | 5.52 | 6.71 | 7.72 |

Mass spectrum (m/z): 283 (M⁺)

Nuclear magnetic resonance spectrum (DMSO-$d_6$, TMS internal standard): δ: 1.80–1.84 (1H, m), 1.89–2.12 (5H, m), 2.65–2.70 (1H, m), 3.08–3.24 (3H, m), 3.91–4.01 (1H, m), 4.10 (1H, br), 6.52 (2H, s), 7.26 (1H, dd), 7.37 (1H, t), 7.57 (1H, d), 7.64 (1H, d)

The product was analyzed by the same manner as described in Example 61. The result showed 99% enantiomeric excess.

Example 65

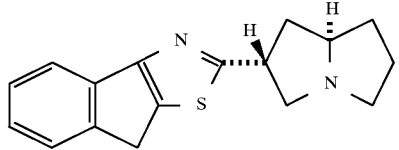

(3R,5R)-3-(8H-Indeno[1,2-d]thiazol-2-yl)-1-azabicyclo[3.3.0]octane

Starting compound (5R)-1-Azabicyclo[3.3.0]octane-3-carbonitrile, 2-bromo-1-indanone.

Melting point: 80°–81° C. petroleum ether $[\alpha]_D^{25}$+8.00 (c=0.50, chloroform)

| Elemental analysis for $C_{17}H_{18}N_2S$ | | | | |
|---|---|---|---|---|
| | C(%) | H(%) | N(%) | S(%) |
| Calcd.: | 72.30 | 6.42 | 9.92 | 11.35 |
| Found: | 72.42 | 6.47 | 9.96 | 11.25 |

Mass spectrum (m/z): 282 (M⁺)

Nuclear magnetic resonance spectrum (CDCl₃, TMS internal standard): δ: 1.43–1.50 (1H, m), 1.73–1.82 (1H, m), 1.85–1.91 (1H, m), 2.06–2.14 (2H, m), 2.32–2.83 (1H, m), 2.59–2.64 (1H, m), 3.17–3.26 (3H, m), 3.75–3.88 (2H, m), 3.79 (2H, s), 7.23 (1H, dd), 7.36 (1H, t), 7.48 (1H, d), 7.76 (1H, d)

The product was analyzed by the same manner as described in Example 61. The result showed 99% enantiomeric excess.

Example 66

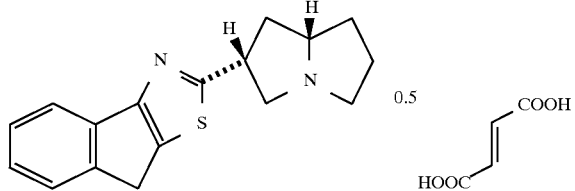

(3R*,5S*)-3-(8H-indeno[1,2-d]thiazol-2-yl)-1-azabicyclo[3.3.0]octane hemifumarate Starting compound 1-Azabicyclo[3.3.0]octane-3-carbonitrile, 2-bromo-1-indanone Melting point: 123°–127° C. acetone Mass spectrum (m/z): 283 (M⁺+1)

Nuclear magnetic resonance spectrum (DMSO-$d_6$, TMS internal standard): δ: 1.68–2.04 (5H, m), 2.55–2.62 (1H, m), 2.88–3.09 (3H, m), 3.70–4.01 (5H, m), 6.47 (1H, s), 7.26 (1H, t), 7.37 (1H, t), 7.57 (1H, d), 7.64 (1H, d)

Example 67

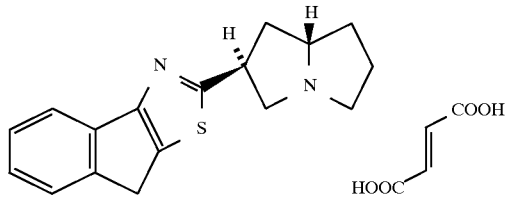

(3R*,5R*)-3-(8H-indeno[1,2-d]thiazol-2-yl)-1-azabicyclo[3.3.0]octane fumarate

Starting compound

1-Azabicyclo[3.3.0]octane-3-carbonitrile, 2-bromo-1-indanone

Melting point: 142°–144° C. acetone

Mass spectrum (m/z): 283 (M⁺+1)

Nuclear magnetic resonance spectrum (DMSO-$d_6$, TMS internal standard): δ: 1.64–1.76 (2H, m), 1.93–1.99 (1H, m), 2.06–2.13 (1H, m), 2.18–2.24 (1H, m), 2.31–2.38 (1H, m), 2.87–2.94 (1H, m), 3.28–3.42 (3H, m), 3.92 (2H, s), 3.98–4.02 (1H, m), 4.04–4.12 (1H, m), 6.49 (2H, s), 7.26 (1H, t), 7.37 (1H, t), 7.57 (1H, d), 7.64 (1H, d)

Example 68

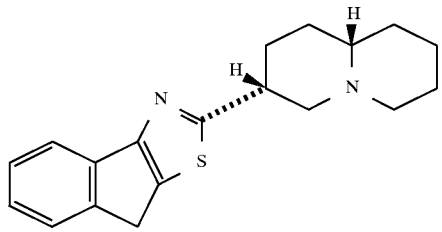

(3R*,6S*)-3-(8H-indeno[1,2-d]thiazol-2-yl)-1-azabicyclo[4.4.0]decane

Starting compound

1-Azabicyclo[4.4.0]decane-3-carbonitrile, 2-bromo-1-indanone

Melting point: 110°–113° C. hexane

Mass spectrum (m/z): 310 (M⁺)

Nuclear magnetic resonance spectrum (CDCl₃, TMS internal standard): δ: 1.23–1.36 (2H, m), 1.44–1.75 (6H, m), 1.81–1.88 (2H, m), 2.02–2.11 (2H, m), 2.46 (1H, dd), 2.80 (1H, d), 3.01 (1H, d), 3.61 (1H, s), 3.78 (2H, d), 7.19–7.22 (1H, m), 7.35 (1H, t), 7.47 (1H, d), 7.76 (1H, d)

Example 69

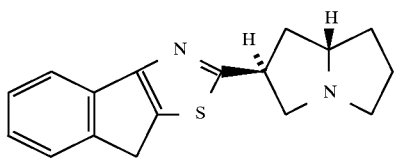

(3R*,6R*)-3-(8H-indeno[1,2-d]thiazol-2-yl)-1-azabicyclo[4.4.0]decane

Starting compound

1-Azabicyclo[4.4.0]decane-3-carbonitrile, 2-bromo-1-indanone

Melting point: 117° C. petroleum ether

| Elemental analysis for C₁₉H₂₂N₂S | | | |
|---|---|---|---|
| | C(%) | H(%) | N(%) | S(%) |
| Calcd.: | 73.51 | 7.14 | 9.02 | 10.33 |
| Found: | 73.63 | 7.26 | 9.05 | 10.07 |

Mass spectrum (m/z): 311 (M⁺+1)

Nuclear magnetic resonance spectrum (CDCl₃, TMS internal standard): δ: 1.28 (2H, m), 1.48 (1H, m), 1.61–1.83 (7H, m), 2.08–2.13 (1H, m), 2.24–2.60 (1H, m), 2.34 (1H, t), 2.88 (1H, d), 3.23 (1H, d), 3.40–3.45 (1H, m), 3.79 (2H, s), 7.22 (1H, t), 7.36 (1H, t), 7.47 (1H, d), 7.78 (1H, d)

Example 70

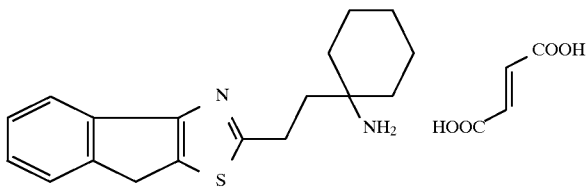

To a solution of 910 mg of 2-[2-(1-nitrocyclohexyl)ethyl]-8H-indeno[1,2-d]thiazole in 10 ml of methanol were added 390 mg of iron(II) sulfate heptahydrate, 290 mg of iron reduced, 30 ml of water, and 1.5 g of concentrated sulfuric acid successively, followed by heating under reflux for 2 hours. The reaction mixture was poured into 1N hydrochloric acid, followed by extraction with ethyl acetate to remove unreacted starting materials. The aqueous layer was then neutralized, followed by extraction with ethyl acetate. The organic layer was washed with water and a saturated aqueous solution of sodium chloride and then dried over anhydrous magnesium sulfate. The solvent was evaporated under reduced pressure, whereby 120 mg of yellow 2-[2-(1-aminocyclohexyl)ethyl]-8H-indeno[1,2-d]thiazole was obtained as a free base. Fumaric acid was added to the resulting compound in ethanol to cause crystallization, and the crystals were recrystallized to give a fumarate.

Melting point: 162°–164° C. ethanol

| Elemental analysis for C₁₈H₂₂N₂S.C₄H₄O₄.0.75H₂O | | | |
|---|---|---|---|
| | C(%) | H(%) | N(%) | S(%) |
| Calcd.: | 61.73 | 6.48 | 6.54 | 7.49 |
| Found: | 62.06 | 6.83 | 6.42 | 7.15 |

Mass spectrum (m/z): 299 (M⁺+1)

Nuclear magnetic resonance spectrum (DMSO-d₆, TMS internal standard): δ: 1.20–1.80 (10H, m), 2.11 (2H, t, J=8.5 Hz), 3.19 (2H, t, J=8.5 Hz), 3.91 (2H, s), 6.47 (2H, s), 7.26 (1H, t, J=7.5 Hz), 7.37 (1H, t, J=7.5 Hz), 7.56 (1H, d, J=7.5 Hz), 7.62 (1H, d, J=7.5 Hz)

Example 71

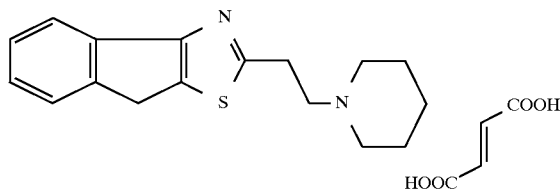

A solution of 500 mg of 2-[(piperidinocarbonyl)methyl]-8H-indeno[1,2-d]thiazole in 10 ml of tetrahydrofuran was added to a suspension of 160 mg of lithium aluminum hydride in 10 ml of tetrahydrofuran at 0° C., followed by heating under reflux for 1.5 hours. The reaction mixture was cooled to 0° C. again, and sodium sulfate decahydrate was added. The resulting mixture was stirred at room temperature for 30 minutes. After the insoluble matter was removed by filtration, the solvent was evaporated. The resulting oily substance was purified by silica gel column chromatography (eluent: chloroform:methanol=10:1), whereby 120 mg of 2-(2-piperidinoethyl)-8H-indeno[1,2-d]thiazole was obtained. Fumaric acid was added to the product in ethanol to cause crystallization, and the crystals were recrystallized to give a fumarate.

Melting point: 133°–135° C. ethanol

| Elemental analysis for C₁₇H₂₀N₂S.C₄H₄O₄.0.5H₂O | | | |
|---|---|---|---|
| | C(%) | H(%) | N(%) | S(%) |
| Calcd.: | 61.59 | 6.15 | 6.84 | 7.83 |
| Found: | 61.61 | 6.00 | 6.76 | 7.93 |

Mass spectrum (m/z): 284 (M⁺)

Nuclear magnetic resonance spectrum (DMSO-d₆, TMS internal standard): δ: 1.35–1.70 (6H, m), 2.55–2.70 (4H, br), 2.88 (2H, t, J=7.0 Hz), 3.31 (2H, t, J=7.0 Hz), 3.90 (2H, s), 6.60 (2H, s), 7.25 (1H, t, J=7.5 Hz), 7.36 (1H, t, J=7.5 Hz), 7.55 (1H, d, J=7.5 Hz), 7.62 (1H, d, J=7.5 Hz)

Example 72

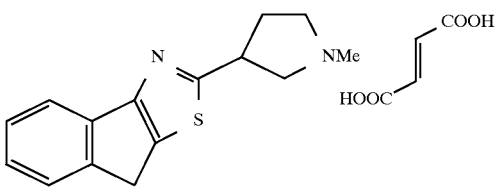

To a solution of 0.11 g of 2-(1-methyl-2-oxo-4-pyrrolidinyl)-8H-indeno[1,2-d]thiazole in 4 ml of tetrahydrofuran, a 1.6 ml of a 1M solution of a borane-tetrahydrofuran complex in tetrahydrofuran was added, followed by heating under reflux for 2 hours. After cooling, a mixed solution of 10 ml of concentrated hydrochloric acid and 10 ml of methanol was added to the reaction mixture, followed by heating under reflux for 1.5 hours. The solvent was evaporated, and ethyl acetate and water were added to the resulting residue, followed by extraction with 1N hydrochloric acid. The aqueous layer was neutralized with sodium bicarbonate, followed by extraction with chloroform and drying over anhydrous magnesium sulfate. The solvent was evaporated, and the resulting residue was subjected to silica gel column chromatography, whereby 0.04 g of 2-(1-methyl-3-pyrrolidinyl)-8H-indeno[1,2-d]thiazole was obtained from the fraction eluted with chloroform-methanol-29% aqueous ammonia (300:10:1). The product was dissolved in methanol. Fumaric acid was added to the resulting solution, followed by crystallization from acetone to give a fumarate.

Melting point: 129°–131° C. acetone

| Elemental analysis for $C_{15}H_{16}N_2S.C_4H_4O_4.0.1H_2O$ | | | | |
|---|---|---|---|---|
| | C(%) | H(%) | N(%) | S(%) |
| Calcd.: | 60.98 | 5.44 | 7.49 | 8.57 |
| Found: | 60.80 | 5.35 | 7.48 | 8.30 |

Mass spectrum (m/z): 256 (M$^+$)

Nuclear magnetic resonance spectrum (DMSO-d$_6$, TMS internal standard): δ: 2.09–2.13 (1H, m), 2.38–2.47 (4H, m), 2.74 (1H, q), 2.84–2.92 (2H, m), 3.10 (1H, t), 3.87–3.93 (3H, m), 6.59 (2H, s), 7.25 (1H, t), 7.36 (1H, t), 7.56 (1H, d), 7.63 (1H, d)

Example 73

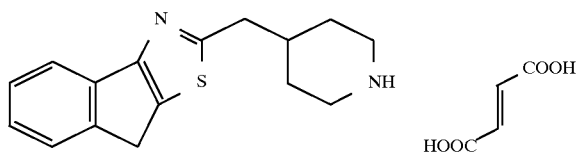

To 0.25 g of 2-[(1-ethoxycarbonyl-4-piperidyl)methyl]-8H-indeno[1,2-d]thiazole was added 10 ml of a 25% solution of hydrogen bromide in acetic acid, followed by heating under reflux for one hour. After cooling, water was added, and the mixture was alkalized with a 1N aqueous solution of sodium hydroxide and potassium carbonate, followed by extraction with chloroform. The extract was dried over anhydrous potassium carbonate. The solvent was then evaporated, whereby 0.23 g of 2-(4-piperidylmethyl)-8H-indeno[1,2-d]thiazole was obtained. The resulting product was dissolved in methanol, fumaric acid was added thereto, followed by crystallization from acetonitrile. The crystals were recrystallized from acetonitrile-methanol to give a fumarate.

Melting point: 188°–189° C. acetonitrile-methanol

| Elemental analysis for $C_{16}H_{18}N_2S.C_4H_4O_4.0.3H_2O$ | | | | |
|---|---|---|---|---|
| | C(%) | H(%) | N(%) | S(%) |
| Calcd.: | 61.30 | 5.81 | 7.15 | 8.18 |
| Found: | 61.25 | 5.69 | 7.11 | 8.14 |

Mass spectrum (m/z): 270 (M$^+$)

Nuclear magnetic resonance spectrum (DMSO-d$_6$, TMS internal standard): δ: 1.40–1.47 (2H, m), 1.82 (2H, d), 2.02–2.05 (1H, m), 2.81 (2H, t), 3.04 (2H, d), 3.21 (2H, d), 3.91 (2H, s), 6.43 (2H, s), 7.25 (1H, t), 7.36 (1H, t), 7.56 (1H, d), 7.63 (1H, d)

Example 74

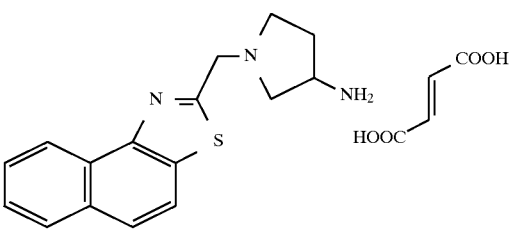

To a solution of 0.11 g of 2-[(3-acetamide-1-pyrrolidinyl)methyl]naphtho[1,2-d]thiazole in 5 ml of ethanol was added 5 ml of 6N hydrochloric acid, followed by heating under reflux for 1.5 hours. After cooling, ethyl acetate was added to the reaction mixture, followed by extraction with 1N hydrochloric acid. The aqueous layer was neutralized with sodium bicarbonate, followed by extraction with chloroform. The extract was dried over anhydrous magnesium sulfate, and the solvent was then evaporated, whereby 0.05 g of 2-[(3-amino-1-pyrrolidinyl)methyl]naphtho[1,2-d]thiazole was obtained. The resulting product was dissolved in methanol, and fumaric acid was added thereto. The resulting mixture was crystallized from ethyl acetate, and the crystals were recrystallized from acetonitrile-methanol to give a fumarate.

Melting point: 188°–189° C. acetonitrile-methanol

| Elemental analysis for $C_{16}H_{17}N_3S.C_4H_4O_4.0.4H_2O$ | | | | |
|---|---|---|---|---|
| | C(%) | H(%) | N(%) | S(%) |
| Calcd.: | 59.46 | 5.36 | 10.40 | 7.94 |
| Found: | 59.29 | 5.33 | 10.42 | 8.12 |

Mass spectrum (m/z): 282 (M$^+$–1)

Nuclear magnetic resonance spectrum (DMSO-d$_6$, TMS internal standard): δ: 1.72–1.80 (1H, m), 2.14–2.33 (1H, m), 2.69–2.76 (2H, m), 2.89–3.01 (2H, m), 3.68–3.73 (1H, m), 4.23 (2H, dd) 6.43 (2H, s), 7.62 (1H, t), 7.70 (1H, t), 7.93 (1H, d), 8.08 (1H, d), 8.13 (1H, d), 8.64 (1H, d)

Example 75

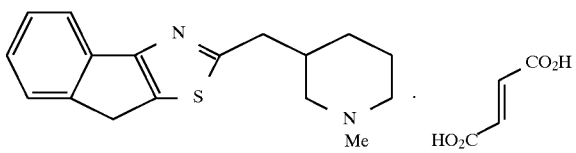

In 0.13 ml of formic acid and 0.3 ml of a 35% aqueous formaldehyde solution, 94 mg of 2-(3-piperidylmethyl)-8H-indeno[1,2-d]thiazole was dissolved, followed by heating at 90° C. for 14 hours. The reaction mixture was diluted with water and chloroform, followed by the addition of potassium carbonate to adjust the pH of the aqueous layer to about 8. An organic layer was separated, and the resulting aqueous layer was extracted twice with chloroform. The organic layers were combined and washed with a saturated aqueous solution of sodium chloride. After drying over anhydrous sodium sulfate, the solvent was evaporated under reduced pressure. The resulting residue was purified by silica gel column chromatography (eluent: chloroform-methanol), whereby 99 mg of a brawn oily substance was obtained. The substance was dissolved in 1 ml of acetonitrile, and 40 mg of fumaric acid was added thereto. The resulting mixture was stirred at room temperature for 30 minutes and the crystals formed were collected by filtration, whereby 90 mg of 2-[(1-methyl-3-piperidyl)methyl]-8H-indeno[1,2-d]thiazole fumarate was obtained.

Melting point: 153° C. (dec.) acetonitrile

| Elemental analysis for $C_{17}H_{20}N_2S.C_4H_4O_4.0.5H_2O$ | | | | |
|---|---|---|---|---|
| | C(%) | H(%) | N(%) | S(%) |
| Calcd.: | 61.59 | 6.15 | 6.84 | 7.83 |
| Found: | 61.40 | 5.83 | 6.65 | 8.06 |

Mass spectrum (m/z): 285 ($M^+$+1)

Nuclear magnetic resonance spectrum (DMSO-$d_6$, TMS internal standard): δ: 1.08–1.20 (1H, m), 1.58–1.80 (3H, m), 2.19–2.30 (1H, m), 2.32–2.53 (5H, m), 3.03–3.15 (4H, m), 3.91 (2H, s), 6.55 (2H, s), 7.23–7.29 (1H, m), 7.36 (1H, t, J=7.3 Hz), 7.56 (1H, d, J=7.3 Hz), 7.65 (1H, d, J=7.3 Hz)

The compounds of the following Examples 76–79 were obtained by the same manner as described in Example 75.

Example 76

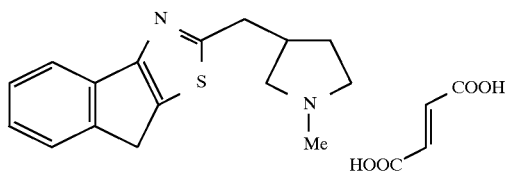

2-[(1-Methyl-3-pyrrolidinyl)methyl]-8H-indeno[1,2-d]thiazole fumarate
Starting compound
2-(3-Pyrrolidinylmethyl)-8H-indeno[1,2-d]thiazole
Melting point: 142°–143° C. acetone-acetonitrile

| Elemental analysis for $C_{16}H_{18}N_2S.C_4H_4O_4$ | | | | |
|---|---|---|---|---|
| | C(%) | H(%) | N(%) | S(%) |
| Calcd.: | 62.16 | 5.74 | 7.25 | 8.30 |
| Found: | 62.11 | 5.69 | 7.22 | 8.31 |

Mass spectrum (m/z): 271 ($M^+$+1)

Nuclear magnetic resonance spectrum (DMSO-$d_6$, TMS internal standard): δ: 1.65–1.74 (1H, m), 2.06–2.14 (1H, m), 2.56 (3H, s), 2.74–2.82 (2H, m), 2.91–3.03 (2H, m), 3.09–3.15 (1H, m), 3.19–3.23 (2H, m), 3.91 (2H, s), 6.52 (2H, s), 7.24 (1H, t), 7.37 (1H, t), 7.56 (1H, d), 7.64 (1H, d)

Example 77

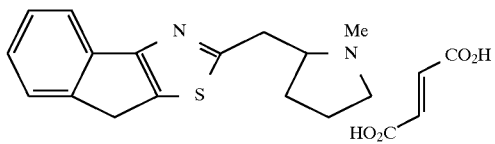

2-[(1-Methyl-2-pyrrolidyl)methyl]-8H-indeno[1,2-d]thiazole fumarate
Starting compound
2-(2-Pyrrolidinylmethyl)-8H-indeno[1,2-d]thiazole
Melting point: 172° C. (dec.) acetonitrile

| Elemental analysis for $C_{16}H_{18}N_2S.C_4H_4O_4.0.2H_2O$ | | | | |
|---|---|---|---|---|
| | C(%) | H(%) | N(%) | S(%) |
| Calcd.: | 61.58 | 5.79 | 7.18 | 8.22 |
| Found: | 61.59 | 5.69 | 7.25 | 8.17 |

Mass spectrum (m/z): 271 ($M^+$+1)

Nuclear magnetic resonance spectrum (DMSO-$d_6$, TMS internal standard): δ: 1.59–1.77 (3H, m), 1.92–1.99 (1H, m), 2.44–2.54 (4H, m), 2.97–3.05 (1H, m), 3.15–3.24 (2H, m), 3.48–3.53 (1H, m), 3.91 (2H, s), 6.58 (2H, s), 7.23–7.27 (1H, m), 7.34–7.38 (1H, m), 7.56 (1H, d, J=7.3 Hz), 7.64 (1H, d, J=7.3 Hz)

Example 78

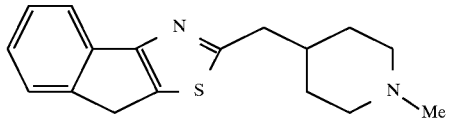

2-[(1-Methyl-4-piperidyl)methyl]-8H-indeno[1,2-d]thiazole
Starting compound
2-(4-Piperidylmethyl)-8H-indeno[1,2-d]thiazole
Melting point: 81°–84° C. diethyl ether-hexane
Mass spectrum (m/z): 284 ($M^+$)
Nuclear magnetic resonance spectrum (CDCl$_3$, TMS internal standard): δ: 1.43 (2H, dq), 1.78 (2H, d), 1.84 (1H, m), 1.94 (2H, t), 2.26 (3H, s), 2.85 (2H, d), 3.02 (2H, d), 3.80 (2H, s), 7.23 (1H, t), 7.37 (1H, t), 7.49 (1H, d), 7.77 (1H, d)

Example 79

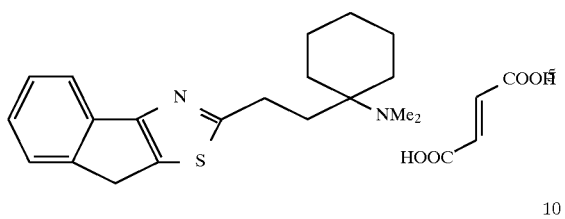

2-[2-(1-Dimethylaminocyclohexyl)ethyl]-8H-indeno[1,2-d]thiazole fumarate

Starting compound

2-[2-(1-Aminocyclohexyl)ethyl]-8H-indeno[1,2-d]thiazole

Melting point: 196° C. (dec.) ethanol

| Elemental analysis for $C_{20}H_{26}N_2S.C_4H_4O_4$ | | | | |
|---|---|---|---|---|
| | C(%) | H(%) | N(%) | S(%) |
| Calcd.: | 65.13 | 6.83 | 6.33 | 7.25 |
| Found: | 64.97 | 6.81 | 6.17 | 7.19 |

Mass spectrum (m/z): 327 (M$^+$+1)

Nuclear magnetic resonance spectrum (DMSO-d$_6$, TMS internal standard): δ: 1.30–1.70 (10H, m), 1.94 (2H, m), 2.30 (6H, s), 3.04 (2H, m), 3.90 (2H, s), 6.59 (2H, s), 7.25 (1H, t, J=8.0 Hz), 7.36 (1H, t, J=8.0 Hz), 7.55 (1H, d, J=8.0 Hz), 7.63 (1H, d, J=8.0 Hz)

Example 80

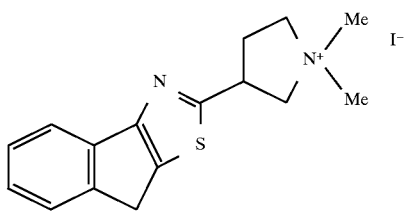

In 2 ml of methyl iodide, 30 mg of 2-(1-methyl-3-pyrrolidinyl)-8H-indeno[1,2-d]thiazole was dissolved, followed by stirring at room temperature for 18 hours. The solvent was evaporated under reduced pressure. The resulting oily substance was crystallized from diethyl ether-chloroform-methanol, whereby 43 mg of 1,1-dimethyl-3-(8H-indeno[1,2-d]thiazol-2-yl)pyrrolidinium iodide was obtained.

Melting point: 195°–197° C. diethyl ether-chloroform-methanol

Mass spectrum (m/z): 271 (M$^+$)

Nuclear magnetic resonance spectrum (DMSO-d$_6$, TMS internal standard): δ: 2.50–2.57 (1H, m), 2.74–2.83 (1H, m), 3.23 (3H, s), 3.30 (3H, s), 3.69–3.81 (2H, m), 3.89 (1H, dd), 3.96 (2H, s), 4.10 (1H, dd), 4.39–4.48 (1H, m), 7.27–7.31 (1H, t) 7.39 (1H, t), 7.59 (1H, d), 7.64 (1H, d)

Example 81

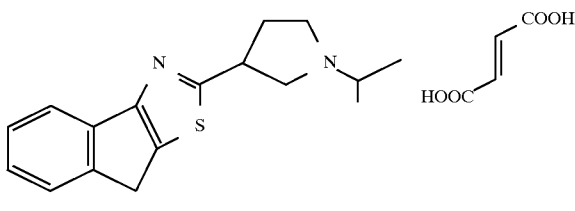

To a solution of 75 mg of 2-(3-pyrrolidinyl)-8H-indeno[1,2-d]thiazole in 1.4 ml of methylene chloride, were added 0.18 ml of acetic acid, 0.045 ml of acetone, and 147 mg of sodium triacetoxyborohydride, followed by stirring at room temperature for 2 hours. Water and a saturated aqueous solution of sodium bicarbonate were added to the reaction mixture. The resulting mixture was extracted with chloroform, followed by drying over anhydrous magnesium sulfate. The solvent was then evaporated and the resulting residue was purified by silica gel column chromatography (eluent: chloroform:methanol:29% ammonium=300:10:1), whereby 30 mg of 2-(1-isopropyl-3-pyrrolidinyl)-8H-indeno[1,2-d]thiazole was obtained. The resulting product was dissolved in methanol. Fumaric acid was added to cause crystallization, and crystals were recrystallized from acetonitrile-methanol to give a fumarate.

Melting point: 141°–143° C. acetonitrile-methanol

| Elemental analysis for $C_{17}H_{20}N_2S.C_4H_4O_4.0.4H_2O$ | | | | |
|---|---|---|---|---|
| | C(%) | H(%) | N(%) | S(%) |
| Calcd.: | 61.87 | 6.13 | 6.87 | 7.87 |
| Found: | 61.79 | 6.08 | 6.86 | 7.90 |

Mass spectrum (m/z): 285 (M$^+$+1)

Nuclear magnetic resonance spectrum (DMSO-d$_6$, TMS internal standard): δ: 1.10–1.13 (6H, m), 2.03–2.12 (1H, m), 2.34–2.43 (1H, m), 2.67–2.70 (1H, m), 2.79–2.85 (1H, m), 2.89–2.97 (2H, m), 3.16–3.21 (1H, m), 3.82–3.91 (3H, m), 6.58 (2H, s), 7.25 (1H, t), 7.36 (1H, t), 7.57 (1H, d), 7.62 (1H, d), 13.00 (1H, br)

Example 82

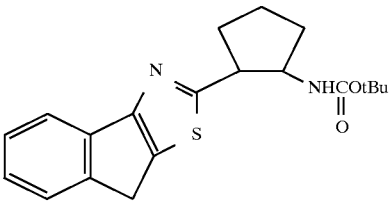

In 50 ml of isopropanol, 0.63 g of 2-(tert-butoxycarbonylamino)cyclopentanecarbothioamide and 0.54 g of 2-bromo-1-indanone were dissolved. Then, 0.26 g of calcium carbonate was added, followed by heating under reflux for 3 hours. After cooling, the insoluble matter was removed by filtration, and the solvent was evaporated. The resulting residue was subjected to silica gel column chromatography eluted with chloroform-methanol-29% aqueous ammonia (100:10:1). The resulting crystals were recrystallized from diethyl ether, whereby 0.11 g of 2-[2-(tert-butoxycarbonylamino)cyclopentyl]-8H-indeno[1,2-d]thiazole was obtained.

Melting point: 155°–158° C. diethyl ether

Elemental analysis for $C_{20}H_{24}N_2O_2S$

| | C(%) | H(%) | N(%) | S(%) |
|---|---|---|---|---|
| Calcd.: | 67.39 | 6.79 | 7.86 | 8.99 |
| Found: | 67.61 | 6.86 | 7.81 | 9.05 |

Mass spectrum (m/z): 357 (M$^+$+1)

Nuclear magnetic resonance spectrum (CDCl$_3$, TMS internal standard): δ: 1.36 (9H, s), 1.56–1.65 (1H, m), 1.81–1.94 (2H, m), 2.03–2.10 (1H, m), 2.26–2.36 (2H, m), 3.36 (1H, br), 3.80 (2H, s), 4.08–4.16 (1H, m), 7.21–7.26 (1H, m), 7.36 (1H, t), 7.48 (1H, d), 7.75 (1H, d)

The compound of the following Example 83 was obtained by the same manner as described in Example 82.

Example 83

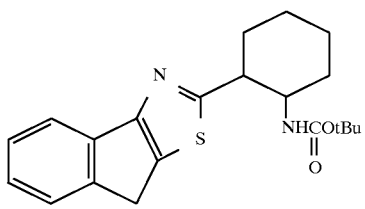

2-[2-(tert-Butoxycarbonylamino)cyclohexyl]-8H-indeno[1,2-d]thiazole
Starting compound
2-(tert-Butoxycarbonylamino)cyclohexanecarbothioamide
Mass spectrum (m/z): 371 (M$^+$+1)
Nuclear magnetic resonance spectrum (CDCl$_3$, TMS internal standard): δ: 1.25–2.00 (17H, m), 3.57 (1H, br), 4.10 (1H, m), 7.22–7.24 (1H, m), 7.38 (1H, t), 7.49 (1H, d), 7.76 (1H, d)

Example 84

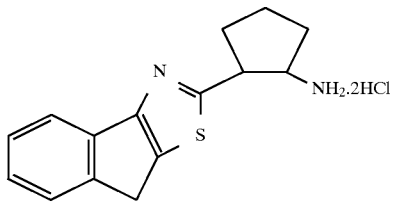

In 6 ml of ethyl acetate, 155 mg of 2-[2-(tert-butoxycarbonylamino)cyclopentyl]-8H-indeno[1,2-d]thiazole was dissolved. Then, 15 ml of a 4N solution of hydrogen chloride in ethyl acetate was added, followed by stirring at room temperature for one hour. The crystals precipitated were collected by filtration, and the crystals were recrystallized from ethyl acetate-methanol, whereby 39 mg of 2-(2-aminocyclopentyl)-8H-indeno[1,2-d]thiazole dihydrochloride was obtained.

Melting point: 143°–146° C. ethyl acetate-methanol

Elemental analysis for $C_{15}H_{16}N_2S \cdot 2HCl \cdot 0.3H_2O$

| | C(%) | H(%) | N(%) | S(%) | Cl(%) |
|---|---|---|---|---|---|
| Calcd.: | 53.83 | 5.60 | 8.37 | 9.58 | 21.18 |
| Found: | 54.19 | 5.53 | 8.48 | 9.41 | 20.87 |

Mass spectrum (m/z): 257 (M$^+$+1)

Nuclear magnetic resonance spectrum (DMSO-d$_6$, TMS internal standard): δ: 1.78–1.99 (3H, m), 2.09–2.24 (3H, m), 3.81–3.88 (2H, m), 3.94 (2H, s), 7.26–7.30 (1H, m), 7.39 (1H, t), 7.59 (1H, d), 7.70 (1H, s)

The compound of the following Example 85 was obtained by the same manner as described Example 84.

Example 85

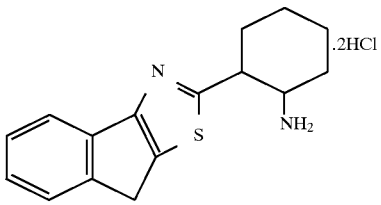

2-(2-Aminocyclohexyl)-8H-indeno[1,2-d]thiazole dihydrochloride
Starting compound
2-[2-(tert-Butoxycarbonylamino)cyclohexyl]-8H-indeno[1,2-d]thiazole
Melting point: 256° C. (dec.) ethyl acetate-methanol
Mass spectrum (m/z): 271 (M$^+$+1)
Nuclear magnetic resonance spectrum (DMSO-d$_6$, TMS internal standard): δ: 1.52–2.10 (8H, m), 3.68–3.71 (2H, m), 3.95 (2H, s), 7.28 (1H, t), 7.39 (1H, t), 7.59 (1H, d), 7.74 (1H, d)

In addition to the above-exemplified compounds, the compounds which will be described below can be synthesized, without particular experiments, in accordance with any one of the above-described preparation processes and processes described in Examples and modified processes thereof, and processes known to those skilled in the art and modified processes thereof (Table 5. Examples B-1 to B-100)

Incidentally, when Ring A is asymmetrical, a bond at the position to combine with L$^1$ is shown in the upper part and a bond at the position to combine L$^2$ is shown in the lower part. When L$^1$ and L$^2$ are asymmetrical, a bond at the position to combine with Ring A is shown in the left hand and the bond at the position to combine with a thiazole ring is shown in the right hand.

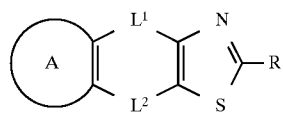
| Example Number | Ring A | L₁ | L₂ | R |
|---|---|---|---|---|
| B-1 | benzene | — | —CH₂— | pyrrolizidine-yl |
| B-2 | benzene | — | —CH₂— | —CH₂-pyrrolizidinyl |
| B-3 | benzene | — | —CH₂— | —CH₂-pyrrolizidinyl |
| B-4 | benzene | — | —CH₂— | pyrrolizidinyl-CH₂— |
| B-5 | benzene | — | —CH₂— | —(CH₂)₂-(1-azabicyclic) |
| B-6 | benzene | — | —CH₂— | —(CH₂)₃-(1-azabicyclic) |
| B-7 | benzene | — | —(CH₂)₂— | —CH₂-(1-azabicyclic) |
| B-8 | benzene | —CH₂— | — | —CH₂-(1-azabicyclic) |
| B-9 | benzene | —(CH₂)₂— | — | —CH₂-(1-azabicyclic) |
| B-10 | benzene | — | —CH₂— | —CH₂-(1-azabicyclic) |

-continued

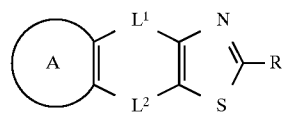

| Example Number | Ring A | L₁ | L₂ | R | |
|---|---|---|---|---|---|
| B-11 | (phenyl) | — | —CH₂— | —CH₂—(quinolizidine) | |
| B-12 | (phenyl) | — | —CH₂— | —CH(CH₃)—(pyrrolidine-NH) | |
| B-13 | (phenyl) | — | —CH₂— | —(CH₂)₂—(pyrrolidine-NH) | |
| B-14 | (phenyl) | — | —CH₂— | —(CH₂)₃—(pyrrolidine-NH) | |
| B-15 | (phenyl) | — | —CH₂— | (pyrrolidine-NH) | |
| B-16 | (phenyl) | —CH₂— | — | (pyrrolidine-NH) | |
| B-17 | (phenyl) | —(CH₂)₂— | — | (pyrrolidine-NH) | |
| B-18 | (phenyl) | — | —CH₂— | —CH₂—(quinuclidine) | |
| B-19 | (phenyl) | — | —CH₂— | (quinuclidine) | |
| B-20 | (phenyl) | — | —CH₂— | —CH₂—(quinuclidine) | |
| B-21 | (phenyl) | — | —CH₂— | (quinuclidine) | |
| B-22 | (phenyl) | — | —CH₂— | —CH₂—(quinuclidine) | |

-continued

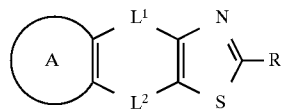

| Example Number | Ring A | L₁ | L₂ | R |
|---|---|---|---|---|
| B-23 | (benzene) | — | —CH₂— | (bicyclic with NH) |
| B-24 | (benzene) | — | —CH₂— | —CH₂—(bicyclic with NH) |
| B-25 | (benzene) | — | —CH₂— | (bicyclic N—Me) |
| B-26 | (benzene) | — | —CH₂— | —CH₂—(bicyclic N—Me) |
| B-27 | (benzene) | — | —CH₂— | (bicyclic N) |
| B-28 | (benzene) | — | —CH₂— | (bicyclic N) |
| B-29 | (benzene) | — | —CH₂— | (indolizidine N) |
| B-30 | (benzene) | — | —CH₂— | (quinolizidine N) |
| B-31 | (benzene) | — | —CH₂— | (quinuclidine N) |
| B-32 | (benzene) | — | —CH₂— | (bicyclic with NH) |
| B-33 | (benzene) | — | —(CH₂)₂— | (piperidine NH) |
| B-34 | (benzene) | — | —(CH₂)₃— | (pyrrolidine NH) |

-continued

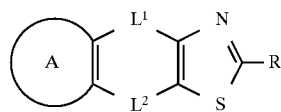

| Example Number | Ring A | L₁ | L₂ | R |
|---|---|---|---|---|
| B-35 | [benzene] | — | —(CH₂)₂— | [−CH₂−(piperidine-fused bicyclic with N)] |
| B-36 | [benzene] | — | —(CH₂)₃— | [−CH₂−(piperidine-fused bicyclic with N)] |
| B-37 | [benzene] | — | —CH₂— | [bicyclic amine] |
| B-38 | [benzene] | — | —CH₂— | [bicyclic amine] |
| B-39 | [benzene] | — | —CH₂— | [quinolizidine] |
| B-40 | [benzene] | — | —CH₂— | —CH₂−[pyrrolizidine] |
| B-41 | [benzene] | — | —CH₂— | [pyrrolizidine] |
| B-42 | [benzene] | — | —CH₂— | —CH₂−[quinolizidine] |
| B-43 | [benzene] | — | —CH₂— | —CH₂−[quinuclidine] |
| B-44 | [benzene] | — | —CH₂— | —CH₂−[quinuclidine] |
| B-45 | [benzene] | — | —CH₂— | —CH₂−[azabicyclic] |

-continued

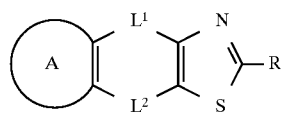

| Example Number | Ring A | L₁ | L₂ | R |
|---|---|---|---|---|
| B-46 | phenyl | — | —CH₂— | —CH₂-(quinuclidinyl) |
| B-47 | phenyl | — | —CH₂— | —CH₂-(azabicyclic NH) |
| B-48 | phenyl | — | —CH₂— | —CH₂-(quinuclidinyl) |
| B-49 | phenyl | — | —CH₂— | (pyrrolizidinyl) |
| B-50 | phenyl | — | —CH₂— | —CH₂-(pyrrolizidinyl) |
| B-51 | phenyl | — | —CH₂— | (azabicyclic NH) |
| B-52 | phenyl | — | —CH₂— | (azabicyclic NH) |
| B-53 | phenyl | — | —CH₂— | (octahydrocyclopenta[c]pyrrolyl NH) |
| B-54 | phenyl | — | —CH₂— | —CH₂-(octahydrocyclopenta[c]pyrrolyl NH) |
| B-55 | phenyl | — | —CH₂— | (octahydroisoindolyl NH) |
| B-56 | phenyl | — | —CH₂— | —CH₂-(dihydropyrrolyl NH) |

-continued

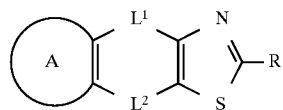

| Example Number | Ring A | L₁ | L₂ | R |
|---|---|---|---|---|
| B-57 | (phenyl) | — | —CH₂— | —(CH₂)₃—N⁺Me₃ I⁻ |
| B-58 | (phenyl) | — | —CH₂— | —(CH₂)₃—N⁺(Me)(pyrrolidine) I⁻ |
| B-59 | (phenyl) | — | —(CH₂)₂— | ethyl-pyrrolidine (NH) |
| B-60 | (phenyl) | — | —(CH₂)₂— | azabicyclic N |
| B-61 | (phenyl) | — | —(CH₂)₃— | pyrrolizidine |
| B-62 | (phenyl) | — | —(CH₂)₃— | cyclopentyl-N⁺Me₂ I⁻ |
| B-63 | (phenyl) | —CH₂— | — | pyrrolizidine |
| B-64 | (phenyl) | — | —CH₂— | bicyclic N⁺-Me with ethyl I⁻ |
| B-65 | (phenyl) | — | —CH₂— | cyclohexyl with propyl, N⁺Me₃ I⁻ |
| B-66 | (phenyl) | —CH₂— | — | —(CH₂)₃—N(Me)₂ |
| B-67 | (phenyl) | —CH₂— | — | —(CH₂)₃—N(pyrrolidine) |

-continued

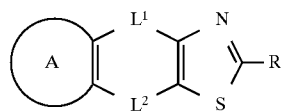

| Example Number | Ring A | L₁ | L₂ | R |
|---|---|---|---|---|
| B-68 | (benzene, 1,2-disubst.) | —CH₂— | — | —(CH₂)₂—C₆H₁₀—NH₂ (1-aminocyclohexyl) |
| B-69 | (benzene, 1,2-disubst.) | — | —CH(Me)— | cyclopentyl-CH₂-NMe₂⁺ I⁻ |
| B-70 | (benzene, 1,2-disubst.) | — | —CH(Me)— | —(CH₂)₂—C₆H₁₀—NH₂ (1-aminocyclohexyl) |
| B-71 | furan (2,3-disubst., O at 1) | — | —(CH₂)₂— | (3R)-pyrrolidin-3-yl-ethyl (NH) |
| B-72 | furan (2,3-disubst., O at 1) | — | —(CH₂)₂— | —(CH₂)₃—N(pyrrolidine) |
| B-73 | furan (2,3-disubst., O at 3) | — | —(CH₂)₂— | azabicyclic amine |
| B-74 | thiophene (2,3-disubst.) | — | —(CH₂)₂— | pyrrolizidine (stereo H,H) |
| B-75 | thiophene (2,3-disubst.) | — | —(CH₂)₂— | —(CH₂)₂—C₆H₁₀—NH₂ (1-aminocyclohexyl) |
| B-76 | thiophene (2,3-disubst.) | — | —CH₂— | cyclopentyl-CH₂-NMe₂⁺ I⁻ |
| B-77 | pyridine (2,3-disubst.) | — | —(CH₂)₂— | —CH₂—(1-azabicyclic spiro) |
| B-78 | pyridine (2,3-disubst.) | — | —CH₂— | —(CH₂)₃—N(Me)(Me) |
| B-79 | 4-fluoro-benzene (1,2-disubst.) | — | —CH₂— | (3R)-pyrrolidin-3-yl-ethyl (NH) |

-continued

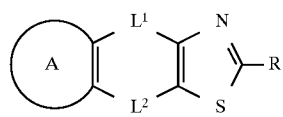

| Example Number | Ring A | L₁ | L₂ | R |
|---|---|---|---|---|
| B-80 | F-phenyl | — | —CH₂— | azetidinyl-CH₂- |
| B-81 | F-phenyl | — | —CH₂— | —(CH₂)₂-C(NH₂)(cyclohexyl) |
| B-82 | MeO-phenyl | — | —CH₂— | —CH₂-(pyrrolizidinyl) |
| B-83 | MeO-phenyl | — | —(CH₂)₂— | —(CH₂)₃-N(pyrrolidinyl) |
| B-84 | 2,3-diMeO phenyl (OMe) | — | —(CH₂)₂— | methyl-indolizidinyl |
| B-85 | 2,3-diMeO phenyl (OMe) | — | —(CH₂)₂— | —(CH₂)₃—N(Me)(iPr-like: CHMe₂) |
| B-86 | thiophene | — |  | azetidinyl |
| B-87 | 3-Me-thiophene | — |  | —(CH₂)₃-N(pyrrolidinyl) |
| B-88 | thiophene | — |  | —(CH₂)₂-C(NH₂)(cyclohexyl) |
| B-89 | thiazole | — |  | methyl-indolizidinyl |
| B-90 | thiazole | — |  | cyclopentyl-NMe₂⁺ I⁻ |

-continued

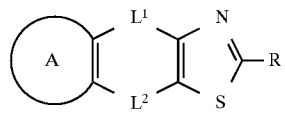

| Example Number | Ring A | L₁ | L₂ | R |
|---|---|---|---|---|
| B-91 | (furan) | — | | —CH₂—(pyrrolizidine) |
| B-92 | (furan) | — | | —(CH₂)₃—N(Me)(Me) |
| B-93 | (pyridine) | — | | (pyrrolizidine, stereo) |
| B-94 | (pyridine) | — | | —(CH₂)₂—(1-aminocyclohexyl) |
| B-95 | (pyridine) | — | | —(CH₂)₃—N(pyrrolidine) |
| B-96 | (benzene) | — | | —(CH₂)₃—N(Me)(Me) |
| B-97 | (benzene) | — | —CH₂— | (3-aminocyclopentyl) |
| B-98 | (benzene) | — | —CH₂— | —CH₂—(3-aminocyclopentyl) |
| B-99 | (benzene) | — | —CH₂— | —CH₂—(azetidinyl NH) |
| B-100 | (benzene) | — | —CH₂— | (azetidinyl NH) |

We claim:

1. A thiazole derivative represented by the following formula (IIc):

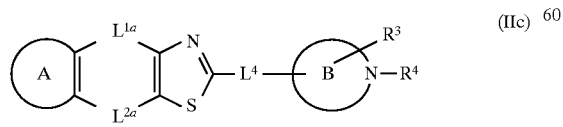

wherein Ring A, L¹ᵃ, L²ᵃ, L⁴, Ring B, R³ and R⁴ have the following meaning:

Ring A: the following ring which may be substituted by one or more substituents selected from the group consisting of a halogen atom, a lower alkyl group and a lower alkoxyl group,:
1) a benzene ring, or
2) a 5-membered or 6-membered unsaturated heterocyclic ring having one or two hetero atoms selected from the group consisting of a nitrogen atom, an oxygen atom and a sulfur atom, L¹ᵃL²ᵃ: one of L¹ᵃ and L²ᵃ represents a single bond and the other one represents an alkylene group having 1 to 4 carbon atoms or an alkenylene group having 2 to 5 carbon atoms, $L^4$: a single bond or a lower alkylene group of 1–5 carbon atoms, $R^3$: a hydrogen atom, a lower alkyl group, an oxo group or a protected or unprotected amino group, $R^4$: non-existent or a hydrogen atom, a lower alkyl group, an aralkyl group or an amino-protecting group, and Ring B: the following monocyclic or bicyclic ring which may contain an oxygen atom:
  1) a nitrogen-containing saturated heterocyclic ring having 4 to 16 ring-forming atoms, or
  2) a nitrogen-containing heterocyclic ring having one unsaturated bond and 4 to 16 ring-forming atoms.

2. A pharmaceutical composition comprised of a therapeutically effective amount of the thiazole derivative of claim 1 and a pharmaceutically acceptable carrier.

3. A compound according to claim 1 wherein $L^{1a}$ is a single bond and $R^4$ represents a hydrogen atom or a lower alkyl, aralkyl, lower alkoxy carbonyl, aralkyloxy-carbonyl, aryloxycarbonyl or acyl group.

4. A compound selected from the group consisting of:

(3R*,5S*)-3-(8H-indeno[1,2-d]thiazole-2-yl)-1-azabicyclo[3,3,0]octane, 2-(3-pyrrolidinylmethyl)-8H-indeno[1,2-d]thiazole, 4-(8H-ideno[1,2-d]thiazole-2-yl)-1-azabicyclo[2,2,1]heptane, (3R,5S)-3-(8H-indeno[1,2-d]thiazole-2-yl-1-azabicyclo[3,3,0]octane, (3S,5R)-3-(8H-indeno[1,2-d]thiazole-2yl)-1-azabicyclo[3,3,0]octane and 5-(8H-indeno[1,2-d]thiazole-2-yl)-1-azabicyclo[3,3,0]octane, and pharmaceutically acceptable salts thereof.

5. The thiazole derivative of claim 1 wherein $L^4$ is a single bond and Ring B is a bicyclic ring.

6. A compound according to claim 3, wherein Ring B is a 1-azabicyclo[3.3.0]octane ring or 1-azabicyclo[2.2.1]heptane ring.

* * * * *